(12) United States Patent
Bowdish et al.

(10) Patent No.: US 7,396,917 B2
(45) Date of Patent: Jul. 8, 2008

(54) RATIONALLY DESIGNED ANTIBODIES

(75) Inventors: Katherine S. Bowdish, Del Mar, CA (US); Shana Frederickson, Solana Beach, CA (US); Mark Renshaw, San Diego, CA (US)

(73) Assignee: Alexion Pharmaceuticals, Inc., Cheshire, CT (US)

(*) Notice: Subject to any disclaimer, the term of this patent is extended or adjusted under 35 U.S.C. 154(b) by 413 days.

(21) Appl. No.: 10/307,724

(22) Filed: Dec. 2, 2002

(65) Prior Publication Data

US 2003/0232972 A1 Dec. 18, 2003

Related U.S. Application Data

(63) Continuation-in-part of application No. 10/006,593, filed on Dec. 5, 2001.

(60) Provisional application No. 60/294,068, filed on May 29, 2001, provisional application No. 60/288,889, filed on May 4, 2001, provisional application No. 60/251,448, filed on Dec. 5, 2000.

(51) Int. Cl.
*C07K 16/00* (2006.01)

(52) U.S. Cl. ............... 530/389.1; 530/387.1; 530/387.3; 530/387.5; 530/388.15; 530/388.24; 530/389.2

(58) Field of Classification Search ............... 530/300, 530/389.1, 389.3, 388.22, 388.85, 387.1, 530/387.3, 387.5, 388.15, 388.24, 389.2; 424/130.1, 133.1; 514/2
See application file for complete search history.

(56) References Cited

U.S. PATENT DOCUMENTS

| | | | |
|---|---|---|---|
| 4,642,334 A | 2/1987 | Moore et al. | |
| 4,783,330 A | 11/1988 | Furie et al. | |
| 4,816,397 A | 3/1989 | Boss et al. | |
| 5,116,964 A | 5/1992 | Capon et al. | |
| 5,219,996 A | 6/1993 | Bodmer et al. | |
| 5,223,409 A | 6/1993 | Ladner et al. | |
| 5,260,417 A | 11/1993 | Grant et al. | |
| 5,428,130 A | 6/1995 | Capon et al. | |
| 5,571,698 A | 11/1996 | Ladner et al. | |
| 5,593,666 A | 1/1997 | McDonald | |
| 5,698,435 A | 12/1997 | Robinson et al. | |
| 5,750,373 A | 5/1998 | Garrard et al. | |
| 5,773,569 A | 6/1998 | Wrighton et al. | |
| 5,837,500 A | 11/1998 | Ladner et al. | |
| 5,869,451 A * | 2/1999 | Dower et al. | 514/13 |
| 5,874,253 A | 2/1999 | Tsujimoto et al. | |
| 5,876,961 A | 3/1999 | Crowe et al. | |
| 5,885,574 A | 3/1999 | Elliott | |
| 5,919,758 A | 7/1999 | Sytkowski | |
| 5,932,546 A | 8/1999 | Barrett et al. | |
| 5,965,405 A | 10/1999 | Winter et al. | |
| 5,969,108 A | 10/1999 | McCafferty et al. | |
| 6,008,023 A | 12/1999 | Opper et al. | |
| 6,040,136 A | 3/2000 | Garrard et al. | |
| 6,162,902 A | 12/2000 | Mischak et al. | |
| 6,172,197 B1 | 1/2001 | McCafferty et al. | |
| 6,342,220 B1 | 1/2002 | Adams et al. | |
| 6,660,843 B1 * | 12/2003 | Feige et al. | 530/391.7 |
| 6,677,124 B2 | 1/2004 | Tsuji et al. | |
| 6,737,249 B1 | 5/2004 | Adams et al. | |
| 6,936,440 B1 | 8/2005 | Cunningham et al. | |
| 7,081,523 B2 | 7/2006 | Elliott | |
| 2003/0162710 A1 | 8/2003 | Sudoh et al. | |

FOREIGN PATENT DOCUMENTS

| | | | |
|---|---|---|---|
| EP | 1642910 A | | 4/2006 |
| WO | WO 94/18221 | * | 8/1994 |
| WO | WO-9511317 | | 4/1995 |
| WO | WO-9529690 | | 11/1995 |
| WO | WO-9640189 | | 12/1996 |
| WO | WO-9640750 | | 12/1996 |
| WO | WO-9910494 | | 3/1999 |
| WO | WO-9925378 | | 5/1999 |
| WO | WO-0024782 | | 5/2000 |
| WO | WO-0061637 | | 10/2000 |
| WO | WO-02/46238 A | | 6/2002 |
| WO | WO-02078612 | | 10/2002 |

OTHER PUBLICATIONS

Barbas et al (b) (PNAS 92:2529-2533, 1995).*
Kini et al (FEBS Letters 375:15-17, 1995).*
Colman et al (Research in Immunology 1994, 145:33-36).*
Rudikoff et al (Proc. Natl. Acad. Sci. USA 1982 vol. 79 p. 1979).*
Ibragimova and Eade (Biophysical Journal, Oct. 1999, vol. 77, pp. 2191-2198).*
Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," Journal of Cell Biology, 111:2129-2138 (1990).
Clemens et al. "Human Brain Natriuretic Peptide Reduces Blood Pressure in normotensive and Acute Norepinephrine-Induced Hypertensive Rabbits" 1997, American Journal of Hypertension vol. 10 pp. 654-664.
De Serres et al., "Pharmacokinetics and Hematological Effects of the PEGylated Thrombopoietin Peptide Mimetic GW395058 in Rats and monkeys After Intravenous or Subcutaneous Administration," Stem Cells, 17(6):316-326 (1999).

(Continued)

*Primary Examiner*—Larry R. Helms
*Assistant Examiner*—Parithosh K. Tungaturthi
(74) *Attorney, Agent, or Firm*—Ropes & Gray LLP

(57) ABSTRACT

Antibodies or fragments thereof having at least two CDR regions replaced or fused with biologically active peptides are described. Compositions containing such antibodies or fragments thereof are useful in therapeutic and diagnostic modalities.

65 Claims, 36 Drawing Sheets

OTHER PUBLICATIONS

Fukui et al., "A New Thiazolodinedione, NC-2100, Which is a Weak PPAR-gamma Activator, Exhibits Potent Antidiabetic Effects and Induces Uncoupling Protein 1 in White Adipose Tissue of KKAY Obese Mice," Diabetes 49:759-767 (2000).

Ibragimova et al., "Stability of the β-Sheet of the WW Domain: A Molecular Dynamics Simulation Study," Biophysical Journal, 77:2191-2198 (1999).

Johnson et al., "Identification of a 13 Amino Acid Peptide Mimetic of Erythropoietin and Description of Amino Acids Critical for the Mimetic Activity of EMP1," Biochemistry, 37:3699-3710 (1998).

Lazar et al., "Transforming Growth Factor α: Mutation of Aspartic Acid 47 and Leucine 48 Results in Different Biological Activities," Molecular and Cell Biology, 8(3):1247-1252 (1998).

Lin et al. "Structure Function Relationships in Glucagon: Properties of Highly Purified Des-His1-, Monoiodo-, and [Des-Asn 28, Thr29](homoserine lactone27) glucagon," Biochemistry USA, 14:1559-1563 (1975).

Montrose-Rafizadeh et al., "High Potency Antagonists of the Pancreatic Glucagon-like Peptide-1 Receptor," The Journal of Biological Chemistry, 272(34):21201-21206 (1997).

Mukoyama et al. "Brain Natriuretic Peptide as a Novel Cardiac Hormone in Humans", Apr. 1991, J. Clinical Investigation vol. 87 pp. 1402-1412.

Rayburn et al., "Nesiritide: A Unique Therapeutic Cardiac Peptide," Reviews in Cardiovascular Medicine, 2(2):S25-S31 (2001).

Roch et al.,, "Altered methional homoeostasis is associated with decreased apoptosis in BAF3 bcl2 murine lymphoid cells," Biochem, 313:973-981 (1996).

Schwartz et al. "A superactive insulin: [B10-Aspartic acid] insulin (human)," Proc. Natl. Acad. Sci. USA, 84:6408-6411 (1987).

Wrighton et al., "Small Peptides as Potent Mimetics of the Protein Hormone Erythropoietin," Science, 273:458-463 (1996).

Johnson et al., "Erythropoietin mimetic peptide and the future," Nephrology Dialysis Transplantation, 15:1274-1277(2000).

Li et al., "Expression of TPO mimetic peptide chimeric proteins with human IgG1 Fc fragments and their biological characters," Sheng Wu Gong Cheng Xue Bao = Chinese Journal of Biotechnology, 18(4):424-430(2002).

Supplementary European Search Report from Application No. EP 03786822, dated Jun. 21, 2006.

Frederickson et al., "A rationally designed agonist antibody fragment that functionally mimics thrombopoietin," PNAS 103(39):14307-14312 (2006).

Alfthan, Kaija, et, al. "Properties of a single-chain antibody containing different linker peptides". 1995. Protein Engineering vol. 8, No. 7, pp. 725-731.

Barbas III, Carlos F., et, al. "Assembly of combinatorial antibody libraries on phage surfaces: The gene III site". Sep. 1991. Proc. Natl. Acad. Sci. USA Biochemistry. vol. 88, pp. 7978-7982.

Barbas, Shana M., et, al. "Human autoantibody reconition of DNA". Mar. 1995. Proc. Natl. Acad. Sci. USA. vol. 92, pp. 2529-2533.

Barbas, Shana M., et, al. "Recognition of DNA by Synthetic Antibodies". Nov. 10, 1993. J. AM. Chem. Soc., vol. 116, No. 5 pp. 2161-2162.

Better, Marc, et, al. "Potent anti-CD5 ricin A chain immunoconjugates from bacterially produced Fab' and F(ab')2". Jan. 1993, Proc. Natl. Acad. Sci. USA, vol. 90, pp. 457-461, Immunology.

Burton, Dennis R., et, al. "Human Antibodies from Combinatorial Libraries". 1994, Advances in Immunology, vol. 57, pp. 191-280.

Carlson, John R., et al., "Molecular Tools for Inactivating a Yeast Enzyme In Vivo". Jun. 1988, Molecular and Cellular Biology, vol. 8, No. 6 pp. 2547-2650.

Carter, Paul, et, al. "High level *Escherichia coli* expression and production of a bivalent humanized antibody fragment" Bio/Technology vol. 10 pp. 163-167, 1992.

Chaiken I M et al., Identifying Structure-Function Relationships in Four-Helix Bundle Cytokines: Towards De Nova Mimetics Design, Trends in Biotechnology, Elsevier Publications Cambridge, GB, vol. 14, No. 10, Oct. 1, 1996, pp. 369-375.

Cook, Jeremy, Recombinant Antibodies Containing an Engineered B-Cell Epitope Capable of Eliciting Conformation-Specific Antibody Responses, Butterworth Heinemann, Vaccine, vol. 13, No. 18, pp. 1770-1778, 1995, Esevier Science Ltd.

Cwirla, Steven E., et. al., "Peptide Agonist of the Thrombopoietin Receptor as Potent as the Natural Cytokine", Jun. 13, 1997, Science, vol. 276 pp. 1696-1699.

de Kruif, John, et, al. "Leucine zipper Dimerized Bivalent and Bispecific scFv Antibodies from a Semi-synthetic Antibody Phage Display Library". Mar. 29, 1996. The J. of Biological Chemistry, vol. 271, No. 13, pp. 7630-7634.

de Sauvage, Frederic J., et, al. "Stimulation of megakaryocytopoiesis and thrombopoiesis by the c-Mpl ligand". Jun. 1994, Nature, vol. 369, pp. 533-538.

DeBernardi, Maria A., et al., "Single cell Ca2+/cAMP cross-talk monitored by simultaneous Ca2+/cAMP fluor escence ratio imaging". May 1996, Proc. Natl. Acad. Sci. USA, vol. 93, pp. 4577-4582, Cell Biology.

Deng, Su-jun, et, al. "Synthetic Antibody Gene Libraries for In Vitro Affinity Maturation". 1995, Methods in Molecular Biolog, vol. 51: Antibody Engineering Protocols. pp. 329-342.

Deng. B. et al. "An Agonist Murine Monoclonal Antibody To The Human C-MPL Receptor Stimulates In Vitro MegaKaryocytopoiesis," Abstract No. XP-002095741 (260) 1996.

Drachman, Jonathan G., et, al. Thrombopoietin Signal Transduction Requires Functional JAK2, Not TYK2. May 7, 1999, The J. of Biological Chemistry, vol. 274, No. 19, pp. 13480-13484.

Eaves, C.J., "Assays of Hemopoietic Progenitor Cells". Williams Hematology. 5th Edition. Chapter L4, pp. L22-L26, 1995.

European Search Report for EP04077554 dated Sep. 21, 2005.

Gallinari, Paola, et al. "Localization of a 34-Amino-Acid Segment Implicated in Dimerzation of the *Herpes simplex* Virus Type 1 ICP4 Ploypeptide by a Dimerization Trap". Jun. 1994, J. of Virology, vol. 68, No. 6, pp. 3809-3820.

Hawkins, Robert E., et, al. "Selection of Phage Antibodies by Binding Affinity". Apr. 1992. J. Mol. Biol. 226, pp. 889-896.

Hayden M S et al, Antibody Engineering, current Opinion in Immunology, Current Biology Ltd, XX, vol. 9, No. 2, Apr. 1997, pp. 201-212.

Healy, Judith M., et, al. "Peptide Ligands for Integrin avb3 Selected from Random Phage Display Libraries", Jan. 13, 1995 Biochemistry vol. 34, No. 12, 1995. pp. 3948-3955.

Helms, Larry, R., et al., "Destabilizing loop swaps in the CDRs of an immunoglobulin $V_L$ domain," Protein Science, 4:2073-2081 (1995).

Hiatt, Andrew, et al., "Production of antibodies in transgenic plants". Nov. 2, 1989, Nature, vol. 342, pp. 76-78.

Hiltunen, Timo, et, al. "Assembly of Humanized Antibody Genes from Synthetic Olgonucleotides Using a Single-Round PCR". Mar. 10, 1994. BioTechniques vol. 17, No. 2.

Holliger, Philipp, et, al. "Engineering bispecific antibodies". 1993, Biotechnology, vol. 4, pp. 446-449.

Ihle, James N., et. al., "Signaling Through the Hematopoietic Cytokine Receptors". (1995), Annu. Rev. Immunology, vol. 13, pp. 369-398.

Jagerschmidt, Alexandre, Human Trombopietin Structure-Function Relationships: Identification of Functionally Important Residues, Biochem. J. (1998) 333, 729-734.

Kamura, Takumi, Characterization of Human Thrombopoietin Gene Promotoer, The Journal of Biological Chemistry, 1997 by The American Society for Biochemistry and Molecular Biology, Inc., vol. 272, No. 17, Issue of Apr. 25, pp. 11361-11368, 1997.

Kim, Baek, et, al. "Dimerization of a Specific DNA-Binding Protein on the DNA". Jan. 1992, Science, vol. 255, pp. 203-206.

Kitamura, Toshio, et, al. "Establishment and Characterization of a Unique Human Cell Line That Proliferates Dependently on GM_CSF, IL-3, or Erythropoietin" Feb. 28, 1989, J. of Cellular Physiology vol. 140 pp. 323-334.

Kitamura, Toshio, et, al. "Identification and Analysis of Human Erythropoietin Receptors on a Factor-Dependent Cell Line, TF-1". Feb. 1989, Blood. vol. 73, No. 2, pp. 375-380.

Kitamura, Toshio, et, al. "IL-1 up-regulates the expression of cytokine receptors on a factor-dependent human hemopoietic cell line, TF-1". (1991) International Immunology, vol. 3, No. 6 pp. 571-577.

Klose, Karl E., et al. "The major Dimerization Determinants of the Nitrgen Regulatory Protein NTRC from Enteric Bacteria Lie in Its Carboxy-terminal Domain". (1994) J. Mol. Biol. vol. 241, pp. 233-245.

Knappik, Achim, et al. "Fully Sythetic Human Combinatorial Antibody Libraries (HuCAL) Based on Modular Consensus Frameworks and CDR's Randomized with Trinucleotides". J. Mol. Biol. (2000). 296. pp. 57-86.

Koivunent, Erkki, et, al. "Phage Libraries Displaying Cyclic peptides with Different Ring Sizes: Ligand Specificities of the RDG-Directed Integrins" Bio/Technology vol. 13 Mar. 1995 pp. 265-270.

Koivunent, Erkki, et, al. "Selection of Peptides Binding to the 5b1 Integrin from Phage Display Library". Sep. 25, 1993. The J. of Biological Chemistry. vol. 268, No. 27, pp. 20205-20210.

Kortt, Alexander A., et, al. "Recombinant anti-sialidase single-chain variable fragment antibody". 1994. Eur. J. Biochem. 221, pp. 151-157.

Kostelny, Sheri A., et, al. "Formation of Bispecific Antibody By The Use Of Leicine Zippers". Mar. 1, 1992, The J. of Immunology, vol. 148, No. 5, pp. 1547-1553.

Koumenis, Iphigenia Leonidou, et al., "Modulating pharmacokinetics of an anti-interleuken-8F(ab')2 by amine-specific PEGylation with preserved bioactivity". International J. of Pharmaceutics (2000), vol. 198, pp. 83-95.

Kunel, Thomas A., "Rapid and efficient site-specific mutagenesis without phenotypic selection", Jan. 1985. Proc. Natl. Acad. Sci. US vol. 82, pp. 488-492.

Lang, Irene M., et, al. "Purification of Storage Granule Protein-23". Nov. 22, 1996. The J. of Biological Chemistry. vol. 271, No. 47, pp. 30126-30135.

Lee, L. Stanford, et, al. "Prolonged Circulating Lives of Single-Chain Fv Proteins Conjugation Chemistries and Compounds". (1999) Bioconjugate Chemistry, vol. 10, No. 6, pp. 973-981.

MacBeath, Gavin, et al., "Redesigning Enzyme Topology by Directed Evolution". Mar. 20, 1998, Science. vol. 279; pp. 1958-1961.

MacBeath, Gavin, et, al. "A Small, Thermosable, and Monofunctional Chorismate Mutase from the Archeon *Methanococcu jannaschii*". (1998) Biochemistry vol. vol. 37, pp. 10062-10073.

Monfardini, C. et al. "Recombinant Antibodies in Bioactive Peptide Design," J. Biochem. 270(12):6628-6638 (1995).

Mosmann, Tim, "Rapid Colorimetric Assay for Cellular Growth and Survival: Application to Proliferation and Cytotoxicity Assays". (1983) J. of Immunological Methods> vol. 63, pp. 5563.

Pack, Peter, et, al. "Miniantibodies: Use of Amphipathic Helices To Produce Functional, Flexibly Linked Dimeric Fv Fragments with High Activity in *Escherichia coli*". Feb. 18, 1992, Biochemistry, vol. 31, No. 6, pp. 1579-1584.

Parhami-Seren B. et al, Selection of High Affinity P-Azophenyarsonate Fabs From Heavy-Chain CDR2 Insertaion Libraries, Journal of Immunological Methods, Elsevier Science Publishers B.V., Amsterdam, NL, vol. 259, No. 1-2, Jan. 1, 2002.

Raines, Elaine W., et, al. "Purification of Human Platelet-Derived Growth Factor". (1985) Methods in Enzymology, vol. 109, pp. 749-773.

Shi, Xu-Bao, et, al. "Rapid PCR Construction of a Gene Containing Lym-1 Antibody Variable Regions", Aug. 1993. PCR Methods-And-Applications vol. 3, No. 1. pp. 46-53.

Siegel, Don L., et, al. "Isolation of cell-surface-specific human monoclonal antibodies using phage display and magnetically-activated cell sorting: applications in immunohematology". 1997, J. of Immunological Methods, 206 pp. 73-85.

Spaeny-Dekking, Liesbeth, et, al. "Gin Invertase of Bacteriophage Mu Is a Dimer in Solution, with the omain for Dimerization in the N-Terminal Part of the Protein". (1995) Biochemistry vol. 34, pp. 1779-1786.

Trill, John J., et al., "Production of monoclonal antibodies in COS and CHO cells", (1995), Current Opinion in Biotechnology, vol. 6 pp. 553-560.

van Heecheren, William J., et al. "Role of the conserved leucines in the leucine zipper dimerization motif of yeast GCN4". Jun. 12, 1992, Nucleic Acids Research, vol. 20. No. 14, pp. 3721-3724.

Witthuhn, Bruce A., et, al. "JAK2 Associates with the Erthropoietin Receptor and Is Tyrosine Phosphorylated and Activated following Stimulation with Erythropoien". Jul. 30, 1993, Cell, vol. 74, pp. 227-236.

* cited by examiner

Human Antibody sequence (TT sequence) (SEQ ID NO: 54)
Heavy Chain: cloning sites Xho I and Spe I are underlined

```
1                                  11
gag gtg cag ctg CTC GAG CAG TCT GGG GCT GAG GTG AAG AAG CCT GGG TCC TCG GTG AAG
glu val gln leu leu glu gln ser gly ala glu val lys lys pro gly ser ser val lys
21                                 31
GTC TCC TGC AGG GCT TCT GGA GGC ACC TTC AAC AAT TAT GCC ATC AGC TGG GTG CGA CAG
val ser cys arg ala ser gly gly thr phe asn asn tyr ala ile ser trp val arg gln
41                                 51
GCC CCT GGA CAA GGG CTT GAG TGG ATG GGA GGG ATC TTC CCT TTC CGT AAT ACA GCA AAG
ala pro gly gln gly leu glu trp met gly gly ile phe pro phe arg asn thr ala lys
61                                 71
TAC GCA CAA CAC TTC CAG GGC AGA GTC ACC ATT ACC GCG GAC GAA TCC ACG GGC ACA GCC
tyr ala gln his phe gln gly arg val thr ile thr ala asp glu ser thr gly thr ala
81                                 91
TAC ATG GAG CTG AGC AGC CTG AGA TCT GAG GAC ACG GCC ATA TAT TAT TGT GCG AGA GGG
tyr met glu leu ser ser leu arg ser glu asp thr ala ile tyr tyr cys ala arg gly
101                                111
GAT ACG ATT TTT GGA GTG ACC ATG GGA TAC TAC GCT ATG GAC GTC TGG GGC CAA GGG ACC
asp thr ile phe gly val thr met gly tyr tyr ala met asp val trp gly gln gly thr
121                                131
ACG GTC ACC GTC TCC GCA GCC TCC ACC AAG GGC CCA TCG GTC TTC CCC cTG GCA CCC TCC
thr val thr val ser ala ala ser thr lys gly pro ser val phe pro leu ala pro ser
141                                151
TCC AAG AGC ACC TCT GGG GGC ACA GCG GCC CTG GGC TGC CTG GTC AAG GAC TAC TTC CCC
ser lys ser thr ser gly gly thr ala ala leu gly cys leu val lys asp tyr phe pro
161                                171
GAA CCG GTG ACG GTG TCG TGG AAC TCA GGC GCC CTG ACC AGC GGC GTG CAC ACC TTC CCG
glu pro val thr val ser trp asn ser gly ala leu thr ser gly val his thr phe pro
181                                191
GCT GTC CTA CAG TCC TCA GGA CTC TAC TCC CTC AGC AGC GTG GTG ACC GTG CCC TCC AGC
ala val leu gln ser ser gly leu tyr ser leu ser ser val val thr val pro ser ser
201                                211
AGC TTG GGC ACC CAG ACC TAC ATC TGC AAC GTG AAT CAC AAG CCC AGC AAC ACC AAG GTG
ser leu gly thr gln thr tyr ile cys asn val asn his lys pro ser asn thr lys val
221                                231
GAC AAG AAA GTT GAG CCC AAA TCT TGT GAC AAA act agt
asp lys lys val glu pro lys ser cys asp lys thr ser
```

Fig. 2A

Human Antibody Sequence (TT sequence) (SEQ ID NO: 55)

Light Chain: cloning sites Sac I and Xba I are underlined

```
1                                      11
gag ctc acg cag tct cca ggc acc ctg tct ttg tct ccA ggg gaa aga gcc acc ctc tcc
glu leu thr gln ser pro gly thr leu ser leu ser pro gly glu arg ala thr leu ser
21                                     31
tgc agg gcc agt cac agt gtt agc agg gcc tac tta gcc tgg tac cag cag aaa cct ggc
cys arg ala ser his ser val ser arg ala tyr leu ala trp tyr gln gln lys pro gly
41                                     51
cag gct ccc agg ctc ctc atc tat ggt aca tcc agc agg gcc act ggc atc cca gac agg
gln ala pro arg leu leu ile tyr gly thr ser ser arg ala thr gly ile pro asp arg
61                                     71
ttc agt ggc agt ggg tct ggg aca gac ttc act ctc acc atc agc aga ctg gag cct gaa
phe ser gly ser gly ser gly thr asp phe thr leu thr ile ser arg leu glu pro glu
81                                     91
gat ttt gca gtg tac tac tgt cag cag tat ggt ggc tca ccg tgg ttc ggc caa ggg acC
asp phe ala val tyr tyr cys gln gln tyr gly gly ser pro trp phe gly gln gly thr
101                                    111
AAG GTG GAA CTC AAA CGA ACT GTG GCT GCA CCA TCT GTC TTC ATC TTC CCG CCA TCT GAT
lys val glu leu lys arg thr val ala ala pro ser val phe ile phe pro pro ser asp
121                                    131
GAG CAG TTG AAA TCT GGA ACT GCC TCT GTT GTG TGC CTG CTG AAT AAC TTC TAT CCC AGA
glu gln leu lys ser gly thr ala ser val val cys leu leu asn asn phe tyr pro arg
141                                    151
GAG GCC AAA GTA CAG TGG AAG GTG GAT AAC GCC CTC CAA TCG GGT AAC TCC CAG GAG AGT
glu ala lys val gln trp lys val asp asn ala leu gln ser gly asn ser gln glu ser
161                                    171
GTC ACA GAG CAG GAC AGC AAG GAC AGC ACC TAC AGC CTC AGC AGC ACC CTG ACG CTG AGC
val thr glu gln asp ser lys asp ser thr tyr ser leu ser ser thr leu thr leu ser
181                                    191
AAA GCA GAC TAC GAG AAA CAC AAA GTC TAC GCC TGC GAA GTC ACC CAT CAG GGC CTG AGC
lys ala asp tyr glu lys his lys val tyr ala cys glu val thr his gln gly leu ser
201                                    211
TTG CCC GTC ACA AAG AGC TTC AAC AGG GGA GAG TGT TAG Ttc tag a
leu pro val thr lys ser phe asn arg gly glu cys AMB
```

Fig. 2B

Method of grafting peptide into antibody with random sequences surrounding peptide sequence FR3 TPO Mimetic Peptide (SEQ ID NO: 56) Y Y C A R X X I E G P T L R Q (SEQ ID NO: 57) TATTAT-TGT-GCG-AGA-NNR-NNR-ATT-GAA-GGG-CCG-ACG-CTG-CGG-CAA-

FR4

W L A A R A X X W G Q G T

TGG-CTG-GCG-GCG-CGC-GCG-NNY-NNY-TGG-GGC-CAA-GGG-ACC-

The TPO mimetic peptide was grafted into the heavy chain CDR3 region of the tetanus toxoid antibody. The peptide was flanked on either side by two random amino acids, shown as "X"s in the figure.

| CLONE | AMINO ACID SEQUENCE | SEQ ID NO. |
|---|---|---|
| X1a | Pro-Pro-Ile-Glu-Gly-Pro-Thr-Leu-Arg-Gln-Trp-Leu-Ala-Ala-Arg-Ala-Gly-Gly<br>CCG-CCC-ATT-GAA-GGG-CCG-ACG-CTG-CGG-CAA-TGG-CTG-GCG-GCG-CGC-GCG-GGA-GGC | 25<br>26 |
| X1a-11 | Gly-Gly-Ile-Glu-Gly-Pro-Thr-Leu-Arg-Gln-Trp-Leu-Ala-Ala-Arg-Ala-Gly-Gly<br>GGG-GGT-ATT-GAA-GGG-CCG-ACG-CTG-CGG-CAA-TGG-CTG-GCG-GCG-CGC-GCG-GGC-GGA | 27<br>28 |
| X1a-13 | Gly-Gly-Ile-Glu-Gly-Pro-Thr-Leu-Arg-Gln-Trp-Leu-Ala-Ala-Arg-Ala-Gly-Gly<br>GGC-GGT-ATT-GAA-GGG-CCG-ACG-CTG-CGG-CAA-TGG-CTG-GCG-GCG-CGC-GCG-GGA-GGC | 29<br>30 |
| X1c | Trp-Leu-Ile-Glu-Gly-Pro-Thr-Leu-Arg-Gln-Trp-Leu-Ala-Ala-Arg-Ala-Pro-Val<br>TGG-CTG-ATT-GAA-GGG-CCG-ACG-CTG-CGG-CAA-TGG-CTG-GCG-GCG-CGC-GCG-CCT-GTC | 31<br>32 |
| X2c | Met-Ile-Ile-Glu-Gly-Pro-Thr-Leu-Arg-Gln-Trp-Leu-Ala-Ala-Arg-Ala-Val-Gly<br>ATG-ATA-ATT-GAA-GGG-CCG-ACG-CTG-CGG-CAA-TGG-CTG-GCG-GCG-CGC-GCG-GTT-GGC | 33<br>34 |
| X3a | Val-Val-Ile-Glu-Gly-Pro-Thr-Leu-Arg-Gln-Trp-Leu-Ala-Ala-Arg-Ala-Pro-Val<br>GTG-GTA-ATT-GAA-GGG-CCG-ACG-CTG-CGG-CAA-TGG-CTG-GCG-GCG-CGC-GCG-CCT-GTT | 35<br>36 |
| X3b | Gly-Pro-Ile-Glu-Gly-Pro-Thr-Leu-Arg-Gln-Trp-Leu-Ala-Ala-Arg-Ala-Pro-Asp<br>GGG-CCG-ATT-GAA-GGG-CCG-ACG-CTG-CGG-CAA-TGG-CTG-GCG-GCG-CGC-GCG-CCC-GAT | 37<br>38 |
| X4b | Leu-Pro-Ile-Glu-Gly-Pro-Thr-Leu-Arg-Gln-Trp-Leu-Ala-Ala-Arg-Ala-Pro-Val<br>TTG-CCA-ATT-GAA-GGG-CCG-ACG-CTG-CGG-CAA-TGG-CTG-GCG-GCG-CGC-GCG-CCT-GTT | 39<br>40 |
| X4c | Ser-Leu-Ile-Glu-Gly-Pro-Thr-Leu-Arg-Gln-Trp-Leu-Ala-Ala-Arg-Ala-Pro-Ile<br>TCA-CTG-ATT-GAA-GGG-CCG-ACG-CTG-CGG-CAA-TGG-CTG-GCG-GCG-CGC-GCG-CCC-ATC | 41<br>42 |
| X5a | Thr-Met-Ile-Glu-Gly-Pro-Thr-Leu-Arg-Gln-Trp-Leu-Ala-Ala-Arg-Ala-Pro-Val<br>ACA-ATG-ATT-GAA-GGG-CCG-ACG-CTG-CGG-CAA-TGG-CTG-GCG-GCG-CGC-GCG-CCC-GTT | 43<br>44 |
| X5c | Thr-Thr-Ile-Glu-Gly-Pro-Thr-Leu-Arg-Gln-Trp-Leu-Ala-Ala-Arg-Ala-Pro-Val<br>ACG-ACA-ATT-GAA-GGG-CCG-ACG-CTG-CGG-CAA-TGG-CTG-GCG-GCG-CGC-GCG-CCT-GTC | 45<br>46 |
| X7a | Thr-Arg-Ile-Glu-Gly-Pro-Thr-Leu-Arg-Gln-Trp-Leu-Ala-Ala-Arg-Ala-Cys-Ser<br>ACA-CGG-ATT-GAA-GGG-CCG-ACG-CTG-CGG-CAA-TGG-CTG-GCG-GCG-CGC-GCG-TGC-AGC | 47<br>48 |
| X7b | no peptide deletion mutant | |
| X7c | Gln-Thr-Ile-Glu-Gly-Pro-Thr-Leu-Arg-Gln-Trp-Leu-Ala-Ala-Arg-Ala-Pro-Asp<br>CAG-ACA-ATT-GAA-GGG-CCG-ACG-CTG-CGG-CAA-TGG-CTG-GCG-GCG-CGC-GCG-CCT-CAC | 49<br>50 |

Fig. 5

(SEQ ID NO: 60)

GGGAAATTGTAAGCGTTAATATTTTGTTAAAATTCGCGTTAAATTTTTGTTAA
ATCAGCTCATTTTTTAACCAATAGGCCGAAATCGGCAAAATCCCTTATAAATC
AAAAGAATAGACCGAGATAGGGTTGAGTGTTGTTCCAGTTTGGAACAAGAGT
CCACTATTAAAGAACGTGGACTCCAACGTCAAAGGGCGAAAAACCGTCTATC
AGGGCGATGGCCCACTACGTGAACCATCACCCTAATCAAGTTTTTGGGGTC
GAGGTGCCGTAAAGCACTAAATCGGAACCCTAAAGGGAGCCCCCGATTTAGA
GCTTGACGGGGAAAGCCGGCGAACGTGGCGAGAAAGGAAGGGAAGAAAGC
GAAAGGAGCGGGCGCTAGGGCGCTGGCAAGTGTAGCGGTCACGCTGCGCGT
AACCACCACACCCGCCGCGCTTAATGCGCCGCTACAGGGCGCGTCAGGTGGC
ACTTTTCGGGGAAATGTGCGCGGAACCCCTATTTGTTTATTTTTCTAAATACA
TTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTGAAA
GTAAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTTCCA
ATGATGAGCACTTTTAAAGTTCTGCTATGTGGCGCGGTATTATCCCGTATTGA
CGCCGGGCAAGAGCAACTCGGTCGCCGCATACACTATTCTCAGAATGACTTG
GTTGAGTACTCACCAGTCACAGAAAAGCATCTTACGGATGGCATGACAGTAA
GAGAATTATGCAGTGCTGCCATAACCATGAGTGATAACACTGCGGCCAACTT
ACTTCTGACAACGATCGGAGGACCGAAGGAGCTAACCGCTTTTTTGCACAAC
ATGGGGGATCATGTAACTCGCCTTGATCGTTGGGAACCGGAGCTGAATGAAG
CCATACCAAACGACGAGCTGTACACCACGATGCCTGTAGCAATGGCAACAAC
GTTGCGCAAACTATTAACTGGCGAACTACTTACTCTAGCTTCCCGGCAACAAT
TAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGT
AGTTATCTACACGACGGGGAGTCAGGCAACTATGGATGAACGAAATAGACA
GATCGCTGAGATAGGTGCCTCACTGATTAAGCATTGGTAACTGTCAGACCAA
GTTTACTCATATATACTTTAGATTGATTTAAAACTTCATTTTTAATTTAAAAGG
ATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCG
CTACCAGCGGTGGTTTGTTTGCCGGATCAAGAGCTACCAACTCTTTTTCCGAA
GGTAACTGGCTTCAGCAGAGCGCAGATACCAAATACTGTCCTTCTAGTGTAG
CCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGA

Fig. 6A

ACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGC
ACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGCGG
AGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAA
CCGCCTCTCCCCGCGCGTTGGCCGATTCATTAATGCAGCTGGCACGACAGGTT
TCCCGACTGGAAAGCGGGCAGTGAGCGCAACGCAATTAATGTGAGTTAGCTC
ACTCATTAGGCACCCCAGGCTTTACACTTTATGCTTCCGGCTCGTATGTTGTG
TGGAATTGTGAGCGGATAACAATTGAATTCAGGAGGAATTTAAAATGAAAAA
GACAGCTATCGCGATTGCAGTGGCACTGGCTGGTTTCGCTACCGTGGCCCAG
GCGGCCGAGCTCGGCCATGGCTGGTTGGGCAGCGAGTAATAACAATCCAGCG
GCTGCCGTAGGCAATAGGTATTTCATTATGACTGTCTCCTTGGCGACTAGCTA
GTTTAGAATTCGTAATCATGGTCATAGCTGTTTCCTGTGTGAAATTGTTATCC
GCTCACAATTCCACACAACATACGAGCCGGAAGCATAAAGTGTAAAGCCTGG
GGTGCCTAATGAGTGAGCTAACTCACATTAATTGCGTTGCGCTCACTGCCCGC
TTTCCAGTCGGGAAACCTGTCGTGTTACTAATGATGGTGATGGTGATGGCTAG
TTTTGTCACAAGATTTGGGCTCAACTTTCTTGTCCACCTTGGTGTTGCTGGGCT
TGTGATTCACGTTGCAGATGTAGGTCTGGGTGCCCAAGCTGCTGGAGGGCAC
GGTCACCACGCTGCTGAgGGAGTAGAGTCCTGAGGACTGTAGGACAGCCGGG
AAGGTGTGCACGCCGCTGGTCAgGGCGCCTGAgTTCCACGACACcGTCGCCGG
TTCgGGGAAGTAGTCCTTGACCAGGCAGCCCAGGGCCGCTGTGCCCCAGAG
GTGCTCTTGGAGGAGGGTGCCAGGGGGAAGACCGATGGGCCCTTGGTGGAG
GCTGCGGAGACGGTGACCGTGGTACCAGCAGAAACCTGGCCAGGCTCCCAG
GCTCCTCATCTATGGTACATCCAGCAGGGCCACTGGCATCCCAGACAGGTTC
AGTGGCAGTGGGTCTGGGACAGACTTCACTCTCACCATCAGCAGACTGGAGC
CTGAAGATTTTGCAGTGTACTACTGTCAGCAGTATGGTGGCTCACCGTGGTTC
GGCCAAGGGACCAAGGTGGAACTCAAACGAACTGTGGCTGCACCATCTGTCT
TCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGG
ATAACGCCCTCCAATCGGGTAACTCCCAGGAGAGTGTCACAGAGCAGGACAG
CAAGGACAGCACCTACAGCCTCAGCAGCACCCTGACGCTGAGCAAAGCAGA
CTACGAGAAACACAAAGTCTACGCCTGCGAAGTCacccatcagggcctgagttcgcccgtcac
aaagagcttcaacggaggagagtgttaatTCTAGATAATTAATTAGGAGGAATTTAAAATGAA
ATACCTATTGCCTACGGCAGCCGCTGGATTGTTATTACTCGCTGCCCAACCAG
CCATGGCCGAGGTGCAGCTGCTCGAGATGAGCGATAAAATTATTCACCTGAC
TGACGACAGTTTTGACACGGATGTACTCAAAGCGGACGGGGCGATCCTCGTC
GATTTCTGGGCAGAGTGGTGCGGTCCGTGCAAAATGATCGCCCCGATTCTGG
ATGAAATCGCTGACGAATATCAGGGCAAACTGACCGTTGCAAAACTGAACAT
CGATCAAAACCCTGGCACTGCGCCGAAATATGGCATCCGTGGTATCCCGACT
CTGCTGCTGTTCAAAAACGGTGAAGTGGCGGCAACCAAAGTGGGTGCACTTG
TCTAAAGGTCAGTTGAAAGAGTTCCTCGACGCTAACCTGGCGTACCCGTACG
ACGTTCCGGACTACGGTTCTACTAGTccgaaaccgtctaccccaccgggctcttcctgcggtggccgc
atcgcccgtctggaggaaaaagtgaaaaccctgaaagctcagaactccgagctggcgtccactgccaacatgctgcgcgaac

Fig. 6B aggtggcacagctgaaacagaaagttatgaaccatggcggttgtgctagtGGCCAGGCCGGCCAGCACCAT
CACCATCACCATGGCGCATACCCGTACGACGTTCCGGACTACGCTTCTTAGG
AGGGTGGTGGCTCTGAGGGTGGCGGTTCTGAGGGTGGCGGCTCTGAGGGAGG
CGGTTCCGGTGGTGGCTCTGGTTCCGGTGATTTTGATTATGAAAAGATGGCAA
ACGCTAATAAGGGGGCTATGACCGAAATGCCGATGAAAACGCGCTACAGTC
TGACGCTAAAGGCAAACTTGATTCTGTCGCTACTGATTACGGTGCTGCTATCG
ATGGTTTCATTGGTGACGTTTCCGGCCTTGCTAATGGTAATGGTGCTACTGGT
GATTTTGCTGGCTCTAATTCCCAAATGGCTCAAGTCGGTGACGGTGATAATTC
ACCTTTAATGAATAATTTCCGTCAATATTTACCTTCCCTCCCTCAATCGGTTGA
ATGTCGCCCTTTTGTCTTTAGCGCTGGTAAACCATATGAATTTTCTATTGATTG
TGACAAAATAAACTTATTCCGTGGTGTCTTTGCGTTTCTTTTATATGTTGCCAC
CTTTATGTATGTATTTTCTACGTTTGCTAACATACTGCGTAATAAGGAGTCTTA
AGCTAGCTAATTAATTTAAGCGGCCGCAGATCT

Fig. 6C

TPO Positive Clones    nnk nnk                nnk nnk
                        1   2   IEGPTLRQWLAARA  3   4

|  | Sample | nnk 1 | nnk 2 | nnk 3 | nnk 4 | Amino Acids 1 | Amino Acids 2 | Amino Acids 3 | Amino Acids 4 |
|---|---|---|---|---|---|---|---|---|---|
| HC CDR3 | X1c | tgg | ctg | cct | gtc | Trp | Leu | Pro | Val |
|  | X3a | gtg | gta | cct | gtt | Val | Val | Pro | Val |
|  | X3b | ggg | ccg | ccc | gat | Gly | Pro | Pro | Asp |
|  | X4b | ttg | cca | cct | gtt | Leu | Pro | Pro | Val |
|  | X4c | tca | ctg | ccc | atc | Ser | Leu | Pro | Ile |
|  | X5a | aca | atg | ccc | gtt | Thr | Met | Pro | Val |
|  | X5c | acg | aca | cct | gtc | Trp | Leu | Pro | Val |
|  | X7c | cag | aca | cct | cac | Gln | Thr | Pro | Asp |
| HC CDR2 | 24 | ctt | tat | tct | aat | Leu | Tyr | Ser | Asn |
|  | 39 | act | tac | ttg | cat | Thr | Tyr | Leu | His |
|  | 3 | agg | atg | ctc | gag | Arg | Met | Leu | Glu |
|  | 7 | aag | gaa | tct | aag | Lys | Glu | Ser | Lys |
|  | 8 | gcg | cat | gtg | cag | Ala | His | Val | Gln |
|  | 10 | cag | gag | att | agt | Gln | Glu | Ile | Ser |
|  | 11 | cgg | aat | aat | ccg | Arg | Asn | Asn | Pro |
|  | 19 | cag | cta | aat | tct | Gln | Leu | Asn | Ser |
|  | 25 | agt | att | ttt | gtc | Ser | Ile | Phe | Val |
|  | 28 | ggg | ccc | act | agt | Gly | Pro | Thr | Ser |
| LC CDR1 | 10 | aag | ggt | gtt | agt | Lys | Gly | Val | Ser |
|  | 11 | cat | ggg | gtg | gct | His | Gly | Val | Ala |
|  | 12a | cgt | acg | atg | gct | Arg | Thr | Met | Ala |
|  | 12b | cgt | ggt | gtt | aat | Arg | Gly | Val | Asn |
|  | 14 | cgt | tcg | ctt | gcg | Arg | Ser | Leu | Ala |
|  | 16 | cgg | ggt | gtt | gcg | Arg | Gly | Val | Ala |
|  | 18 | agg | acg | gtg | tct | Arg | Thr | Val | Ser |
|  | 47 | aag | ggg | gtg | gcg | Lys | Gly | Val | Ala |
| LC CDR2 | 1 | aat | ccg | agg | ggt | Asn | Pro | Arg | Gly |
|  | 2 | tcg | cct | cgg | agt | Ser | Pro | Arg | Ser |
|  | 3 | tcg | cct | cgt | acg | Ser | Pro | Arg | Thr |
|  | 4 | tcg | cct | tgg | cgt | Ser | Pro | Trp | Arg |
|  | 5 | act | ccg | aat | tgg | Thr | Pro | Asn | Trp |
|  | 6 | aat | cct | gcg | agg | Asn | Pro | Ala | Arg |
|  | 7 | aat | ccg | tcg | ggg | Asn | Pro | Ser | Gly |
|  | 9 | aat | cct | tat | tag | Asn | Pro | Tyr | Stop |
|  | 10 | aat | ccg | cgg | tct | Asn | Pro | Arg | Ser |
|  | 11 | aat | ccg | gat | gtg | Asn | Pro | Asp | Val |
|  | 12 | tcg | ccg | tcg | cgg | Ser | Pro | Ser | Arg |
|  | 13 | aat | cct | ctg | ttt | Asn | Pro | Leu | Phe |
|  | 14 | aat | ctt | ggg | tat | Asn | Pro | Gly | Tyr |
|  | 15 | aat | cct | att | agt | Asn | Pro | Ile | Ser |
|  | 16 | aat | cct | cag | cgg | Asn | Pro | Gln | Arg |
|  | 18 | aat | ccg | cgg | acg | Asn | Pro | Arg | Thr |
|  | 19 | aat | ccg | cgt | ggg | Asn | Pro | Arg | Gly |
|  | 20 | cat | ttg | aga | ctg | His | Leu | Arg | Leu |
|  | 21 | aag | tag | att | tat | Lys | Stop | Ile | Tyr |
|  | 23 | aat | cct | ggt | aag | Asn | Pro | Gly | Lys |
|  | 24 | aat | cct | cgt | ggg | Asn | Pro | Arg | Gly |
|  | 26 | aat | cct | aat | gtg | Asn | Pro | Asn | Val |
|  | 27 | tct | ccg | cgg | gtt | Ser | Pro | Arg | Val |
|  | 29 | acg | cct | cgg | ggt | Thr | Pro | Arg | Gly |
|  | 30 | cct | tag | tgg | tgg | Pro | Stop | Trp | Trp |

FIG. 9

(SEQ ID NO: 67)

5G1.1 – TPO Heavy Chain (Bold denotes TPO mimetic) Amino acid sequence:

*MKWSWVILFLLSVTAGVHS*QVQLVQSGAEVKKPGASVKVSCKASGYIFSNYWIQW
VRQAPGQGLEWMGEILPGSGSTEYTENFKDRVTMTRDTSTSTVYMELSSLRSED
TAVYYCARLPIEGPTLRQWLAARAPVWGQGTLVTVSSASTKGPSVFPLAPCSR
STSESTAALGCLVKDYFPEPVTVSWNSGALTSGVHTFPAVLQSSGLYSLSSVVTV
PSSNFGTQTYTCNVDHKPSNTKVDKTVERKCCVECPPCPAPPVAGPSVFLFPPKP
KDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRL
TVDKSRWQEGNVFSCSVMHEALHNHYTQKSLSLSLGK.

(SEQ ID NO: 68)

5G1.1 – TPO Heavy Chain (Bold denotes TPO mimetic) Nucleic acid sequence:

ATGAAGTGGAGCTGGGTTATTCTCTTCCTCCTGTCAGTAACTGCCGGCGTCCA
CTCCCAAGTCCAACTGGTGCAATCCGGCGCCGAGGTCAAGAAGCCAGGGGCC
TCAGTCAAAGTGTCCTGTAAAGCTAGCGGCTATATTTTTTCTAATTATTGGAT
TCAATGGGTGCGTCAGGCCCCCGGGCAGGGCCTGGAATGGATGGGTGAGATC
TTACCGGGCTCTGGTAGCACCGAATATACCGAAAATTTTAAAGACCGTGTTA
CTATGACGCGTGACACTTCGACTAGTACAGTATACATGGAGCTCTCCAGCCTG
CGATCGGAGGACACGGCCGTCTATTATTGCGCGCGTTTGCCAATTGAAGGG
CCGACGCTGCGGCAATGGCTGGCGGCGCGCGCGCCTGTTTGGGGTCAAG
GAACCCTGGTCACTGTCTCGAGCGCCTCCACCAAGGGCCCATCCGTCTTCCCC
CTGGCGCCCTGCTCCAGGAGCACCTCCGAGAGCACAGCCGCCCTGGGCTGCC
TGGTCAAGGACTACTTCCCCGAACCGGTGACGGTGTCGTGGAACTCAGGCGC
CCTGACCAGCGGCGTGCACACCTTCCCGGCTGTCCTACAGTCCTCAGGACTCT
ACTCCCTCAGCAGCGTGGTGACCGTGCCCTCCAGCAACTTCGGCACCCAGAC
CTACACCTGCAACGTAGATCACAAGCCCAGCAACACCAAGGTGGACAAGAC
AGTTGAGCGCAAATGTTGTGTCGAGTGCCCACCGTGCCCAGCACCACCTGTG
GCAGGACCGTCAGTCTTCCTCTTCCCCCCAAAACCCAAGGACACCCTCATGAT
CTCCCGGACCCCTGAGGTCACGTGCGTGGTGGTGGACGTGAGCCAGGAAGAC
CCCGAGGTCCAGTTCAACTGGTACGTGGATGGCGTGGAGGTGCATAATGCCA
AGACAAAGCCGCGGGAGGAGCAGTTCAACAGCACGTACCGTGTGGTCAGCG
TCCTCACCGTCCTGCACCAGGACTGGCTGAACGGCAAGGAGTACAAGTGCAA
GGTCTCCAACAAAGGCCTCCCGTCCTCCATCGAGAAAACCATCTCCAAAGCC
AAAGGGCAGCCCCGAGAGCCACAGGTGTACACCCTGCCCCCATCCCAGGAG
GAGATGACCAAGAACCAGGTCAGCCTGACCTGCCTGGTCAAAGGCTTCTACC
CCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCT
CCGTGATGCATGAGGCTCTGCACAACCACTACACACAGAAGAGCCTCTCCCT
GTCTCTGGGTAAATGA

Fig. 13A (SEQ ID NO: 69)

5G1.1 Light Chain Amino Acid Sequence

*MDMRVPAQLLGLLLLWLRGARC*DIQMTQSPSSLSASVGDRVTITCGASENIYGALN
WYQQKPGKAPKLLIYGATNLADGVPSRFSGSGSGTDFTLTISSLQPEDFATYYCQ
NVLNTPLTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTH
QGLSSPVTKSFNRGEC.

(SEQ ID NO: 70)

5G1.1 Light Chain Nucleic Acid Sequence

ATGGACATGAGGGTCCCCGCTCAGCTCCTGGGGCTCCTGCTACTCTGGCTCCG
AGGTGCCAGATGTGATATCCAGATGACCCAGTCCCCGTCCTCCCTGTCCGCCT
CTGTGGGCGATAGGGTCACCATCACCTGCGGCGCCAGCGAAAACATCTATGG
CGCGCTGAACTGGTATCAACAGAAACCCGGGAAAGCTCCGAAGCTTCTGATT
TACGGTGCGACGAACCTGGCAGATGGAGTCCCTTCTCGCTTCTCTGGATCCGG
CTCCGGAACGGATTTCACTCTGACCATCAGCAGTCTGCAGCCTGAAGACTTC
GCTACGTATTACTGTCAGAACGTTTTAAATACTCCGTTGACTTTCGGACAGGG
TACCAAGGTGGAAATAAAACGAACTGTGGCTGCACCATCTGTCTTCATCTTCC
CGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACA
GCACCTACAGCCTCAGCAGCACCCTGACGCTGAGCAAAGCAGACTACGAGA
AACACAAAGTCTACGCCTGCGAAGTCACCCATCAGGGCCTGAGCTCGCCCGT
CACAAAGAGCTTCAACAGGGGAGAGTGTTAG

Note: Italics denotes leader sequence

Fig. 13B

VARIABLE REGION OF 4-29 LIGHT CHAIN (SEQ ID NO: 116)

```
                                                                          CDR1
 1   2   3   4   5   6   7   8   9  10  11  12  13  14  15  16  17  18  19  20  21  22  23  24  25  26  27  27a 27b 27c 27d 27e 27f 28
GAC ATC CAG ATG ACC CAG TCT CCA TCC CTG TCT GCA TCT GTA GGA GAC AGA GTC ACC ATC ACT TGC CGG GCG AGT CAG ... ... ... ... ... ... AGT

Grafted CDR2                                                  CDR1
 29  30  31  32  33  34  35  36  37  38  39  40  41  42  43  44  45  46  47  48  49  50  51  52  52a 52b 52c 52d 52e 52f 52g 52h 52i 52j
ATT AGT AGT TTG CTG GCC TGG TAT CAG CAG AAA CCA GGG AAA GCT CCT AAG CTC CTG ATC TAT AAC CCG ATC GAA GGC CCA ACC CTG CGC CAG TGG CTG GCT Grafted CDR2
 52k 53  54  55  56  57  58  59  60  61  62  63  64  65  66  67  68  69  70  71  72  73  74  75  76  77  78  79  80  81  82  83  84  85
 ACT CGC GCT CGT GGT GGG GTC CCA TCA AGG TTC AGC GGC AGT GGA TCT GGG ACA GAT TTC ACT CTC ACC ATC AGC AGC CTG CAG CCT GAA GAT TTT GCA ACT CDR3
 86  87  88  89  90  91  92  93  94  95  96  97  98  99 100 101 102 103 104 105 106 107
 TAT TAC TGC CAA CAG TAT AAT AGT TAC CCT CCC ACT TTC GGC CCT GGG ACC AAA GTG GAT ATC AAA
```

Fig. 16

ATACCAAACGACGAGCTGTACACCACGATGCCTGTAGCAATGGCAACAACGTTGCCGCAAACTATTAACTGGCGAACTACTTACTCTAGCTTCCCGGCAAC
BsrGI                                    BsrDI AclI  FspI

————— beta-lactamase —————

AATTAATAGACTGGATGGAGGCGGATAAAGTTGCAGGACCACTTCTGCGCTCGGCCCTTCCGGCTGGCTGGTTTATTGCTGATAAATCTGGAGCCGGTGA
   AseI                                        EclI                  BgII

————— beta-lactamase —————

GCGTGGGTCTCGCGGTATCATTGCAGCACTGGGGCCAGATGGTAAGCCCTCCCGTATCGTAGTTATCTACACGACGGGGAGTCAGGCAACTATGGATGAA
  BpmI
  BsaI BsrDI                        BmrI                                                        AhdI

————— beta-lactamase —————

CGAAATAGACAGATCGCTGAGATAGGTGCCTCACTGATTAAGCATTGGTAACTGTCAGACCAAGTTTACTCATATATACTTTAGATTGATTTAAAACTTC
                                                                                            DraI

————— beta-lactamase —————

ATTTTAATTTAAAAGGATCTAGGTGAAGATCCTTTTTTGATAATCTCATGACCAAAAATCCCTTAACGTGAGTTTTCGTTCCACTGAGCGTCAGACCCCGT
    DraI                                                BspHI

AGAAAAGATCAAAGGATCTTCTTGAGATCCTTTTTTTCTGCGCGTAATCTGCTGCTTGCAAACAAAAAAACCACCGCTACCAGCGGTGGTTTGTTTGCCG

Fig. 21D

```
                                                                                                  Eco57I
GATCAAGAGCTACCAACTCTTTTTCCGAAGGTAACTGGCTTCAGCAGAGCAGATACCAAATACTGTCCTTCTAGTGTAGCCGTAGTTAGGCCACCACT
                                                     colE I origin                                                                    1800

TCAAGAACTCTGTAGCACCGACTACATACCCTCGCTCTGCTAATCCTGTTACCAGTGGCTGCTGCCAGTGGCGATAAGTCGTGTCTTACCGGGTTGGACTC
                                             colE I origin                          AlwNI                                             1900

AAGACGATAGTTACCGGATAAGGCGCAGCGGTCGGGCTGAACGGGGGGTTCGTGCACACAGCCCAGCTTGGAGCGAACGACCTACACCGAACTGAGATAC
                                                                    ApaLI
                                                        colE I origin                                                                 2000

CTACAGCGTGAGCTATGAGAAAGCGCCACGCTTCCCGAAGGGAGAAAGGCGGACAGGTATCCGGTAAGCGGCAGGGTCGGAACAGGAGAGCGCACGAGGG
                                                          colE I origin                      EciI BclVI            BssSI              2100

AGCTTCCAGGGGGAAACGCCTGGTATCTTTATAGTCCTGTCGGGTTTCGCCACCTCTGACTTGAGCGTCGATTTTTGTGATGCTCGTCAGGGGGCGGAG
                                                          colE I origin            DrdI                                               2200
                                                                                               PciI
CCTATGGAAAAACGCCAGCAACGCGGCCTTTTTACGGTTCCTGGCCTTTTGCTGGCCTTTTGCTCACATGTTCTTTCCTGCGTTATCCCCTGATTCTGTG
    colE I origin       EciI                                                                                                           2300
```

116 Light Chain (SEQ. ID NO. 122):

EIVLTQSPGTLSLSPGERATLSCRASQSVSSSYLAWYQQKPGQAPRLLIYGASSRATGIPDRFSG
SGSGTDFTLTISRLEPEDFAVYYCQQYGSSPWTFGQGTKVEIKRTVAAPSVFIFPPSDEQLKSGT
ASVVCLLNNFYPREAKVQWKVDNALQSGNSQESVTEQDSKDSTYSLSSTLTLSKADYEKHKVYA
CEVTHQGLSLPVTKSFNRGEC.

Variable Region of 116 Light Chain (SEQ. ID NO. 123):

EIVLTQSPGTLSLSPGERATLSCRASQSVSSSYLAWYQQKPGQAPRLLIYGASSRATGIPDRFSG
SGSGTDFTLTISRLEPEDFAVYYCQQYGSSPWTFGQGTKVEIK

116 Heavy Chain (SEQ. ID NO. 124):

QVQLVQSGAEVKKPGSSVKVSCKASGGTFSSYAISWVRQAPGQGLEWMGQLIEGPTLRQWLA
ARANSRVTITADESTSTAYMELSSLRSEDTAVYYCARLPIEGPTLRQWLAARAPVWGQGTTVTV
SSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKK { <u>VEPKSCDKTHTCPPCP</u> } *APELLGGP* end CH1 constant domain↗      hinge region      tail region

Variable Region of 116 Heavy Chain (SEQ. ID NO. 125):

QVQLVQSGAEVKKPGSSVKVSCKASGGTFSSYAISWVRQAPGQGLEWMGQLIEGPTLRQWLA
ARANSRVTITADESTSTAYMELSSLRSEDTAVYYCARLPIEGPTLRQWLAARAPVWGQGTTVTV
SS

Clone 116. The light chain sequence is as given. The heavy chain may have several forms depending on the final antibody form. For example: the minimum sequence ending with the CH1 constant domain may result in Fab assembly but the heavy chain/light chain interaction will not be stable. Commonly, a portion of the hinge region containing a cysteine (the underlined bold portion of hinge region) may be included for a covalent interaction between the heavy and light chains. Fab'₂ association would need further cysteines such as an entire IgG₁ hinge region (bold). In this example, clone 116 was cloned in a Xoma pING3302 modified vector which includes a transition tail region (italicized).

Figure 22

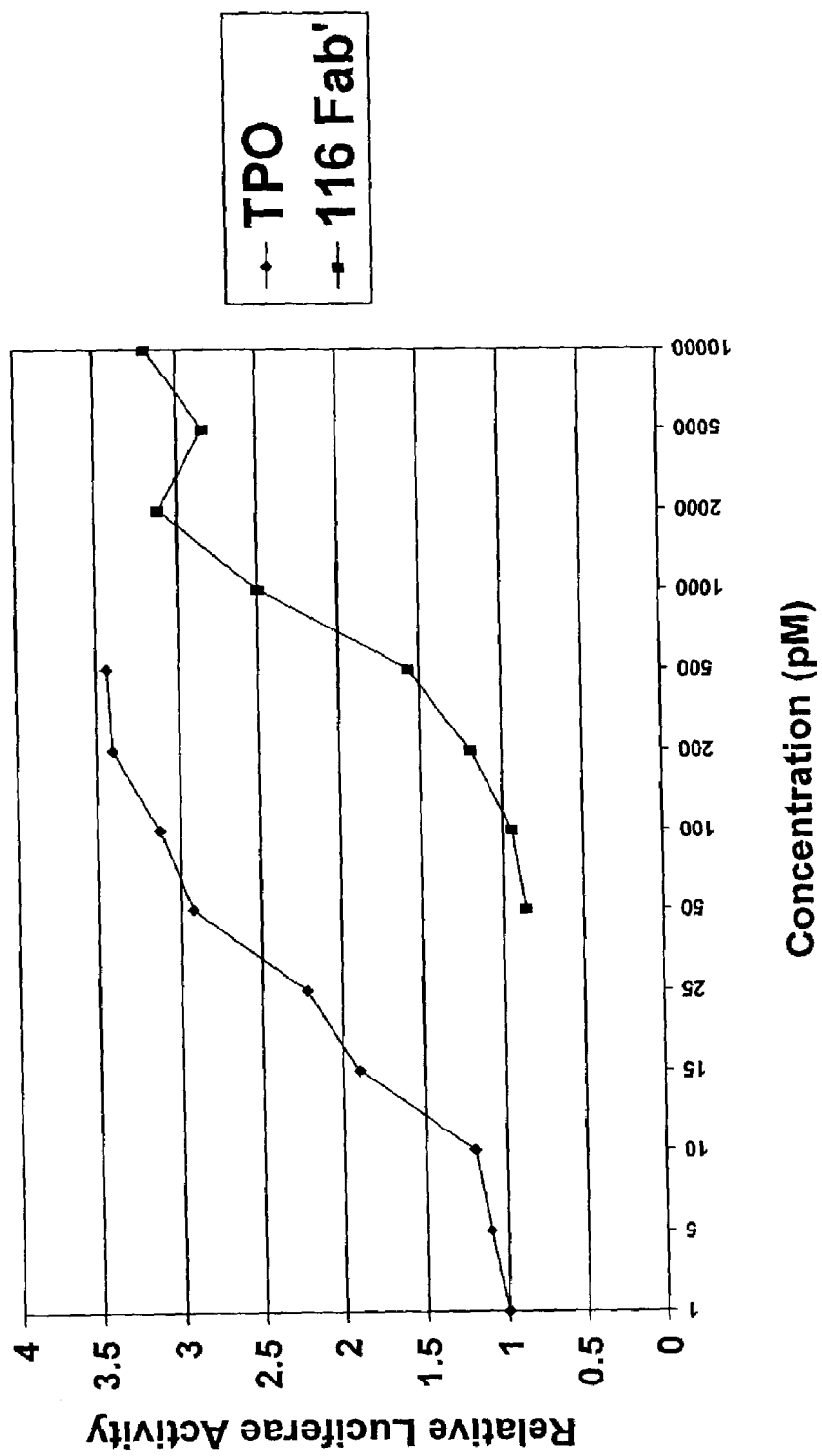
Figure 23: Activity of 116 Fab' prep #5

Figure 24

Sample Sequences of Heavy Chain CDR2 clones

Gly-Ile-Phe-xxx-xxx-Ile-Glu-Gly-Pro-Thr-Leu-Arg-Gln-Trp-Leu-Ala-Arg-Ala-Ala-Arg-Ala-xxx-xxx-Gly (SEQ ID NO. 126)
TT backbone   randomized                        TPO peptide                          randomized  TT backbone

| Clone | Amino Acid Sequence |
|---|---|
| HR2-14 | Gly-Ile-Phe-Ser-Pro-Ile-Glu-Gly-Pro-Thr-Leu-Arg-Gln-Trp-Leu-Ala-Arg-Ala-Ala-Arg-Ala-Ala-Gly-Gly (SEQ. ID NO. 127) |
| HR2-20 | Gly-Ile-Phe-Pro-Gln-Ile-Glu-Gly-Pro-Thr-Leu-Arg-Gln-Trp-Leu-Ala-Arg-Ala-Ala-Arg-Ala-Lys-His-Gly (SEQ. ID NO. 128) |
| HR2-23 | Gly-Ile-Phe-Pro-Asn-Ile-Glu-Gly-Pro-Thr-Leu-Arg-Gln-Trp-Leu-Ala-Arg-Ala-Ala-Arg-Ala-Thr-Gly-Gly (SEQ. ID NO. 129) |
| HR2-28 | Gly-Ile-Phe-Lys-Gly-Ile-Glu-Gly-Pro-Thr-Leu-Arg-Gln-Trp-Leu-Ala-Arg-Ala-Ala-Arg-Ala-Pro-Gly-Gly (SEQ. ID NO. 130) |
| HR2-43 | Gly-Ile-Phe-Pro-Pro-Ile-Glu-Gly-Pro-Thr-Leu-Arg-Gln-Trp-Leu-Ala-Arg-Ala-Ala-Arg-Ala-Ala-Val-Gly (SEQ. ID NO. 131) |
| HR2-44 | Gly-Ile-Phe-Pro-Arg-Ile-Glu-Gly-Pro-Thr-Leu-Arg-Gln-Trp-Leu-Ala-Arg-Ala-Ala-Arg-Ala-Lys-Leu-Gly (SEQ. ID NO. 132) |
| HR2-48 | Gly-Ile-Phe-Pro-Arg-Ile-Glu-Gly-Pro-Thr-Leu-Arg-Gln-Trp-Leu-Ala-Arg-Ala-Ala-Arg-Ala-Lys-Leu-Gly (SEQ. ID NO. 133) |
| HR2-50 | Gly-Ile-Phe-Pro-Tyr-Ile-Glu-Gly-Pro-Thr-Leu-Arg-Gln-Trp-Leu-Ala-Arg-Ala-Ala-Arg-Ala-Lys-Arg-Gly (SEQ. ID NO. 134) |

SEQUENCE LISTING

```
<160> NUMBER OF SEQ ID NOS: 134

<210> SEQ ID NO 1
<211> LENGTH: 14
<212> TYPE: PRT
<213> ORGANISM: artificial sequence
<220> FEATURE:
<223> OTHER INFORMATION: TPO/mimetic peptide

<400> SEQUENCE: 1

Ile Glu Gly Pro Thr Leu Arg Gln Trp Leu Ala Ala Arg Ala
1               5                   10

<210> SEQ ID NO 2
<211> LENGTH: 15
<212> TYPE: PRT
<213> ORGANISM: artificial sequence
<220> FEATURE:
<223> OTHER INFORMATION: TPO mimetic with flanking amino acids

<400> SEQUENCE: 2

Ile Glu Gly Pro Thr Leu Arg Gln Trp Leu Ala Ala Arg Ala Pro
1               5                   10                  15

<210> SEQ ID NO 3
<211> LENGTH: 18
<212> TYPE: PRT
<213> ORGANISM: artificial sequence
<220> FEATURE:
<223> OTHER INFORMATION: EPO mimetic peptide

<400> SEQUENCE: 3

Asp Tyr His Cys Arg Met Gly Pro Leu Thr Trp Val Cys Lys Pro Leu
1               5                   10                  15

Gly Gly

<210> SEQ ID NO 4
<211> LENGTH: 16
<212> TYPE: PRT
<213> ORGANISM: human

<400> SEQUENCE: 4

Gly Asp Thr Ile Phe Gly Val Thr Met Gly Tyr Tyr Ala Met Asp Val
1               5                   10                  15

<210> SEQ ID NO 5
<211> LENGTH: 24
<212> TYPE: DNA
<213> ORGANISM: artificial sequence
<220> FEATURE:
<223> OTHER INFORMATION: primer
```

```
<400> SEQUENCE: 5
tatcgcgatt gcagtggcac tggc                                              24

<210> SEQ ID NO 6
<211> LENGTH: 59
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 6
gccagccatt gccgcagcgt cggcccttca atynnynntc tcgcacaata atatatggc        59

<210> SEQ ID NO 7
<211> LENGTH: 59
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 7
ccgacgctgc ggcaatggct ggcggcgcgc gcgnnynnyt ggggccaagg gaccaccgt        59

<210> SEQ ID NO 8
<211> LENGTH: 22
<212> TYPE: DNA
<213> ORGANISM: artificial sequence
<220> FEATURE:
<223> OTHER INFORMATION: primer

<400> SEQUENCE: 8
tcaaaatcac cggaaccaga gc                                                22

<210> SEQ ID NO 9
<211> LENGTH: 59
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (33)..(33)
<223> OTHER INFORMATION: n is a, c, g or t
<220> FEATURE:
<221> NAME/KEY: misc_feature
<222> LOCATION: (36)..(36)
<223> OTHER INFORMATION: n is a, c, g or t

<400> SEQUENCE: 9
gccagccatt gccgcagcgt cggcccttca atnggnggtc tcgcacaata atatatggc        59

<210> SEQ ID NO 10
<211> LENGTH: 59
```

```
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (36)..(36)
<223> OTHER INFORMATION: n is a, c, g or t
<220> FEATURE:
<221> NAME/KEY: misc_feature
<222> LOCATION: (39)..(39)
<223> OTHER INFORMATION: n is a, c, g or t

<400> SEQUENCE: 10
ccgacgctgc ggcaatggct ggcggcgcgc gcgggnggnt ggggccaagg gaccaccgt    59

<210> SEQ ID NO 11
<211> LENGTH: 59
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (33)..(33)
<223> OTHER INFORMATION: n is a, c, g or t
<220> FEATURE:
<221> NAME/KEY: misc_feature
<222> LOCATION: (36)..(36)
<223> OTHER INFORMATION: n is a, c, g or t

<400> SEQUENCE: 11
gccagccatt gccgcagcgt cggcccttca atnccncctc tcgcacaata atatatggc    59

<210> SEQ ID NO 12
<211> LENGTH: 59
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (36)..(36)
<223> OTHER INFORMATION: n is a, c, g or t
<220> FEATURE:
<221> NAME/KEY: misc_feature
<222> LOCATION: (39)..(39)
<223> OTHER INFORMATION: n is a, c, g or t

<400> SEQUENCE: 12
ccgacgctgc ggcaatggct ggcggcgcgc gcgggnggnt ggggccaagg gaccaccgt    59

<210> SEQ ID NO 13
<211> LENGTH: 21
<212> TYPE: DNA
<213> ORGANISM: artificial sequence
<220> FEATURE:
<223> OTHER INFORMATION: primer

<400> SEQUENCE: 13
gctgcccaac cagccatggc c                                             21

<210> SEQ ID NO 14
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
```

```
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 14
ccaaccctgc gccagtggct ggctgctcgc gctnnknnka gagtcaccat taccgcggac    60

<210> SEQ ID NO 15
<211> LENGTH: 24
<212> TYPE: DNA
<213> ORGANISM: artificial sequence
<220> FEATURE:
<223> OTHER INFORMATION: primer

<400> SEQUENCE: 15
agcgtagtcc ggaacgtcgt acgg                                           24

<210> SEQ ID NO 16
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (35)..(36)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t

<400> SEQUENCE: 16
agccagccac tggcgcaggg ttgggccttc gatmnnmnna cagtagtaca ctgcaaaatc    60

<210> SEQ ID NO 17
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 17
ccaaccctgc gccagtggct ggctgctcgc gctnnknnkt tcggccaagg gaccaaggtg    60

<210> SEQ ID NO 18
<211> LENGTH: 21
<212> TYPE: DNA
<213> ORGANISM: artificial sequence
<220> FEATURE:
<223> OTHER INFORMATION: primer

<400> SEQUENCE: 18
ggccatggct ggttgggcag c                                              21

<210> SEQ ID NO 19
<211> LENGTH: 60
<212> TYPE: DNA
<213> ORGANISM: artificial sequence
```

```
<220> FEATURE:
<223> OTHER INFORMATION: primer
<220> FEATURE:
<221> NAME/KEY: misc_feature
<222> LOCATION: (35)..(36)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t

<400> SEQUENCE: 19
agccagccac tggcgcaggg ttgggccttc gatmnnmnna tagatgagga gcctgggagc    60

<210> SEQ ID NO 20
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 20
ccaaccctgc gccagtggct ggctgctcgc gctnnknnkg gcatcccaga caggttcagt    60

<210> SEQ ID NO 21
<211> LENGTH: 63
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t
<220> FEATURE:
<221> NAME/KEY: misc_feature
<222> LOCATION: (41)..(42)
<223> OTHER INFORMATION: n is a, c, g or t

<400> SEQUENCE: 21
cacccaggtc agtgggccca tgcgmnnatg atagtcmnnm nntctcgcac aataatatat    60
ggc                                                                  63

<210> SEQ ID NO 22
<211> LENGTH: 63
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t
<220> FEATURE:
<221> NAME/KEY: misc_feature
<222> LOCATION: (40)..(41)
```

-continued

```
<223> OTHER INFORMATION: n is a, c, g or t

<400> SEQUENCE: 22
cgcatgggcc cactgacctg ggtgnnkaaa ccactgnnkn nktggggcca agggaccacg    60
gtc                                                                 63

<210> SEQ ID NO 23
<211> LENGTH: 63
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t
<220> FEATURE:
<221> NAME/KEY: misc_feature
<222> LOCATION: (41)..(42)
<223> OTHER INFORMATION: n is a, c, g or t

<400> SEQUENCE: 23
cacccaggtc agtgggccca tgcgmnnatg atagtcmnnm nnacagtagt acactgcaaa    60
atc                                                                 63

<210> SEQ ID NO 24
<211> LENGTH: 63
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t
<220> FEATURE:
<221> NAME/KEY: misc_feature
<222> LOCATION: (40)..(41)
<223> OTHER INFORMATION: n is a, c, g or t

<400> SEQUENCE: 24
cgcatgggcc cactgacctg ggtgnnkaaa ccactgnnkn nkttcggcca agggaccaag    60
gtg                                                                 63

<210> SEQ ID NO 25
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 25

Pro Pro Ile Glu Gly Pro Thr Leu Arg Gln Trp Leu Ala Ala Arg Ala
1               5                   10                  15

Gly Gly

<210> SEQ ID NO 26
<211> LENGTH: 54
<212> TYPE: DNA
```

-continued

<213> ORGANISM: artificial sequence
<220> FEATURE:
<223> OTHER INFORMATION: nucleic acid encoding TPO mimetic with flanking
      amino acids

<400> SEQUENCE: 26
ccgcccattg aagggccgac gctgcggcaa tggctggcgg cgcgcgcggg aggc            54

<210> SEQ ID NO 27
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 27

Gly Gly Ile Glu Gly Pro Thr Leu Arg Gln Trp Leu Ala Ala Arg Ala
1               5                   10                  15

Gly Gly

<210> SEQ ID NO 28
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 28
gggggtattg aagggccgac gctgcggcaa tggctggcgg cgcgcgcggg cgga            54

<210> SEQ ID NO 29
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 29

Gly Gly Ile Glu Gly Pro Thr Leu Arg Gln Trp Leu Ala Ala Arg Ala
1               5                   10                  15

Gly Gly

<210> SEQ ID NO 30
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 30
ggcggtattg aagggccgac gctgcggcaa tggctggcgg cgcgcgcggg aggc            54

<210> SEQ ID NO 31
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 31

Trp Leu Ile Glu Gly Pro Thr Leu Arg Gln Trp Leu Ala Ala Arg Ala
1               5                   10                  15

Pro Val

<210> SEQ ID NO 32
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 32
tggctgattg aagggccgac gctgcggcaa tggctggcgg cgcgcgcgcc tgtc            54

<210> SEQ ID NO 33
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 33

Met Ile Ile Glu Gly Pro Thr Leu Arg Gln Trp Leu Ala Ala Arg Ala
1               5                   10                  15

Val Gly

<210> SEQ ID NO 34
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 34
atgataattg aagggccgac gctgcggcaa tggctggcgg cgcgcgcggt tggc            54

<210> SEQ ID NO 35
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 35

Val Val Ile Glu Gly Pro Thr Leu Arg Gln Trp Leu Ala Ala Arg Ala
1               5                   10                  15

Pro Val

<210> SEQ ID NO 36
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 36
gtggtaattg aagggccgac gctgcggcaa tggctggcgg cgcgcgcgcc tgtt            54

<210> SEQ ID NO 37
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 37

Gly Pro Ile Glu Gly Pro Thr Leu Arg Gln Trp Leu Ala Ala Arg Ala
1               5                   10                  15

Pro Asp

<210> SEQ ID NO 38
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 38
gggccgattg aagggccgac gctgcggcaa tggctggcgg cgcgcgcgcc cgat          54

<210> SEQ ID NO 39
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 39

Leu Pro Ile Glu Gly Pro Thr Leu Arg Gln Trp Leu Ala Ala Arg Ala
1               5                   10                  15

Pro Val

<210> SEQ ID NO 40
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 40
ttgccaattg aagggccgac gctgcggcaa tggctggcgg cgcgcgcgcc tgtt          54

<210> SEQ ID NO 41
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 41

Ser Leu Ile Glu Gly Pro Thr Leu Arg Gln Trp Leu Ala Ala Arg Ala
1               5                   10                  15

Pro Ile

<210> SEQ ID NO 42
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 42
tcactgattg aagggccgac gctgcggcaa tggctggcgg cgcgcgcgcc catc          54

<210> SEQ ID NO 43
<211> LENGTH: 18
<212> TYPE: PRT

```
<213> ORGANISM: artificial sequence
<220> FEATURE:
<223> OTHER INFORMATION: TPO mimetic with flanking amino acids

<400> SEQUENCE: 43

Thr Met Ile Glu Gly Pro Thr Leu Arg Gln Trp Leu Ala Ala Arg Ala
1               5                   10                  15

Pro Val

<210> SEQ ID NO 44
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 44
acaatgattg aagggccgac gctgcggcaa tggctggcgg cgcgcgcgcc cgtt           54

<210> SEQ ID NO 45
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 45

Thr Thr Ile Glu Gly Pro Thr Leu Arg Gln Trp Leu Ala Ala Arg Ala
1               5                   10                  15

Pro Val

<210> SEQ ID NO 46
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 46
acgacaattg aagggccgac gctgcggcaa tggctggcgg cgcgcgcgcc tgtc           54

<210> SEQ ID NO 47
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 47

Thr Arg Ile Glu Gly Pro Thr Leu Arg Gln Trp Leu Ala Ala Arg Ala
1               5                   10                  15

Cys Ser

<210> SEQ ID NO 48
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 48
acacggattg aagggccgac gctgcggcaa tggctggcgg cgcgcgcgtg cagc           54
```

<210> SEQ ID NO 49
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 49

Gln Thr Ile Glu Gly Pro Thr Leu Arg Gln Trp Leu Ala Ala Arg Ala
1               5                   10                  15

Pro Asp

<210> SEQ ID NO 50
<211> LENGTH: 54
<212> TYPE: DNA
<213> ORGANISM: artificial sequence
<220> FEATURE:
<223> OTHER INFORMATION: nucleic acid encoding TPO mimetic with flanking
      amino acids

<400> SEQUENCE: 50
cagacaattg aagggccgac gctgcggcaa tggctggcgg cgcgcgcgcc tcac          54

<210> SEQ ID NO 51
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (35)..(36)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t

<400> SEQUENCE: 51
agccagccac tggcgcaggg ttgggccttc gatmnnmnnt cccatccact caagcccttg    60

<210> SEQ ID NO 52
<211> LENGTH: 270
<212> TYPE: DNA
<213> ORGANISM: artificial sequence
<220> FEATURE:
<223> OTHER INFORMATION: portion of vector

<400> SEQUENCE: 52
actagtccga aaccgtctac cccaccgggc tcttcctgcg gtggccgcat cgcccgtctg    60
gaggaaaaag tgaaaaccct gaaagctcag aactccgagc tggcgtccac tgccaacatg   120
ctgcgcgaac aggtggcaca gctgaaacag aaagttatga accatggcgg ttgtgctagt   180
ggccaggccg gccagcacca tcaccatcac catggcgcat acccgtacga cgttccggac   240
tacgcttctt aggagggtgg tggctctgag                                    270

<210> SEQ ID NO 53
<211> LENGTH: 81
<212> TYPE: PRT
<213> ORGANISM: artificial sequence
<220> FEATURE:
<223> OTHER INFORMATION: portion of polypeptide encoded by Seq.52

<400> SEQUENCE: 53

```
Pro Lys Pro Ser Thr Pro Pro Gly Ser Ser Cys Gly Gly Arg Ile Ala
1               5                   10                  15

Arg Leu Glu Glu Lys Val Lys Thr Leu Lys Ala Gln Asn Ser Glu Leu
            20                  25                  30

Ala Ser Thr Ala Asn Met Leu Arg Glu Gln Val Ala Gln Leu Lys Gln
        35                  40                  45

Lys Val Met Asn His Gly Gly Cys Ala Ser Gln Ala Gly Gln His
    50                  55                  60

His His His His His Gly Ala Tyr Pro Tyr Asp Val Pro Asp Tyr Ala
65                  70                  75                  80

Ser
```

```
<210> SEQ ID NO 54
<211> LENGTH: 699
<212> TYPE: DNA
<213> ORGANISM: human

<400> SEQUENCE: 54
gaggtgcagc tgctcgagca gtctggggct gaggtgaaga agcctgggtc ctcggtgaag    60
gtctcctgca gggcttctgg aggcaccttc aacaattatg ccatcagctg ggtgcgacag   120
gcccctggac aagggcttga gtggatggga ggatcttcc ctttccgtaa tacagcaaag    180
tacgcacaac acttccaggg cagagtcacc attaccgcgg acgaatccac gggcacagcc   240
tacatggagc tgagcagcct gagatctgag gacacggcca tatattattg tgcgagaggg   300
gatacgattt ttggagtgac catgggatac tacgctatgg acgtctgggg ccaagggacc   360
acggtcaccg tctccgcagc ctccaccaag ggcccatcgg tcttcccct ggcaccctcc    420
tccaagagca cctctggggg cacagcggcc ctgggctgcc tggtcaagga ctacttcccc   480
gaaccggtga cggtgtcgtg gaactcaggc gccctgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagaaag ttgagcccaa atcttgtgac aaaactagt                           699

<210> SEQ ID NO 55
<211> LENGTH: 646
<212> TYPE: DNA
<213> ORGANISM: human

<400> SEQUENCE: 55
gagctcacgc agtctccagg caccctgtct ttgtctccag gggaaagagc caccctctcc    60
tgcagggcca gtcacagtgt tagcagggcc tacttagcct ggtaccagca gaaacctggc   120
caggctccca ggctcctcat ctatggtaca tccagcaggg ccactggcat cccagacagg   180
ttcagtggca gtgggtctgg gacagacttc actctcacca tcagcagact ggagcctgaa   240
gattttgcag tgtactactg tcagcagtat ggtggctcac cgtggttcgg ccaagggacc   300
aaggtggaac tcaaacgaac tgtggctgca ccatctgtct tcatcttccc gccatctgat   360
gagcagttga aatctggaac tgcctctgtt gtgtgcctgc tgaataactt ctatcccaga   420
gaggccaaag tacagtggaa ggtggataac gccctccaat cgggtaactc ccaggagagt   480
gtcacagagc aggacagcaa ggacagcacc tacagcctca gcagcaccct gacgctgagc   540
aaagcagact acgagaaaca caaagtctac gcctgcgaag tcacccatca gggcctgagc   600
ttgcccgtca caaagagctt caacagggga gagtgttagt tctaga                  646
```

<210> SEQ ID NO 56
<211> LENGTH: 28
<212> TYPE: PRT
<213> ORGANISM: artificial sequence
<220> FEATURE:
<223> OTHER INFORMATION: portion of artificial heavy chain variable
      region
<220> FEATURE:
<221> NAME/KEY: misc_feature
<222> LOCATION: (6)..(7)
<223> OTHER INFORMATION: Xaa is any of 14 amino acids
<220> FEATURE:
<221> NAME/KEY: misc_feature
<222> LOCATION: (22)..(23)
<223> OTHER INFORMATION: Xaa is any of 14 amino acids encoded by the
      triplet NNY which eliminates all stops

<400> SEQUENCE: 56

Tyr Tyr Cys Ala Arg Xaa Xaa Ile Glu Gly Pro Thr Leu Arg Gln Trp
1               5                   10                  15

Leu Ala Ala Arg Ala Xaa Xaa Trp Gly Gln Gly Thr
            20                  25

<210> SEQ ID NO 57
<211> LENGTH: 84
<212> TYPE: DNA
<213> ORGANISM: artificial sequence
<220> FEATURE:
<223> OTHER INFORMATION: nucleotides encoding artificial CDR3
<220> FEATURE:
<221> NAME/KEY: misc_feature
<222> LOCATION: (16)..(17)
<223> OTHER INFORMATION: n is a, c, g or t
<220> FEATURE:
<221> NAME/KEY: misc_feature
<222> LOCATION: (19)..(20)
<223> OTHER INFORMATION: n is a, c, g or t
<220> FEATURE:
<221> NAME/KEY: misc_feature
<222> LOCATION: (64)..(65)
<223> OTHER INFORMATION: n is a, c, g or t
<220> FEATURE:
<221> NAME/KEY: misc_feature
<222> LOCATION: (67)..(68)
<223> OTHER INFORMATION: n is a, c, g or t

<400> SEQUENCE: 57
tattattgtg cgagannrnn rattgaaggg ccgacgctgc ggcaatggct ggcggcgcgc    60
gcgnnynnyt ggggccaagg gacc                                          84

<210> SEQ ID NO 58
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 58
ccaaccctgc gccagtggct ggctgctcgc gctnnknnkt ggtaccagca gaaacctggc    60

<210> SEQ ID NO 59
<211> LENGTH: 60

```
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (35)..(36)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t

<400> SEQUENCE: 59
agccagccac tggcgcaggg ttgggccttc gatmnnmnng caggagaggg tggctctttc      60

<210> SEQ ID NO 60
<211> LENGTH: 5149
<212> TYPE: DNA
<213> ORGANISM: artificial sequence
<220> FEATURE:
<223> OTHER INFORMATION: vector

<400> SEQUENCE: 60
gggaaattgt aagcgttaat attttgttaa aattcgcgtt aaattttgt taaatcagct      60 cattttttaa ccaataggcc gaaatcggca aaatccctta taaatcaaaa gaatagaccg     120
agatagggtt gagtgttgtt ccagtttgga acaagagtcc actattaaag aacgtggact     180
ccaacgtcaa agggcgaaaa accgtctatc agggcgatgg cccactacgt gaaccatcac     240
cctaatcaag ttttttgggg tcgaggtgcc gtaaagcact aaatcggaac cctaaaggga     300
gcccccgatt tagagcttga cggggaaagc cggcgaacgt ggcgagaaag gaagggaaga     360
aagcgaaagg agcgggcgct agggcgctgg caagtgtagc ggtcacgctg cgcgtaacca     420
ccacacccgc cgcgcttaat gcgccgctac agggcgcgtc aggtggcact tttcggggaa     480
atgtgcgcgg aacccctatt tgtttatttt tctaaataca ttcaaatatg tatccgctca     540
tgagacaata accctgataa atgcttcaat aatattgaaa aaggaagagt atgagtattc     600
aacatttccg tgtcgccctt attccctttt ttgcggcatt tgccttcct gttttgctc      660 acccagaaac gctggtgaaa gtaaaagatg ctgaagatca gttgggtgca cgagtgggtt     720
acatcgaact ggatctcaac agcggtaaga tccttgagag ttttcgcccc gaagaacgtt     780
ttccaatgat gagcactttt aaagttctgc tatgtggcgc ggtattatcc cgtattgacg     840
ccgggcaaga gcaactcggt cgccgcatac actattctca gaatgacttg gttgagtact     900
caccagtcac agaaaagcat cttacggatg gcatgacagt aagagaatta tgcagtgctg     960
ccataaccat gagtgataac actgcggcca acttacttct gacaacgatc ggaggaccga    1020
aggagctaac cgcttttttg cacaacatgg gggatcatgt aactcgcctt gatcgttggg    1080
aaccggagct gaatgaagcc ataccaaacg acgagcgtga caccacgatg cctgtagcaa    1140
tggcaacaac gttgcgcaaa ctattaactg gcgaactact tactctagct tcccggcaac    1200
aattaataga ctggatggag gcggataaag ttgcaggacc acttctgcgc tcggcccttc    1260
cggctggctg gtttattgct gataaatctg gagccggtga gcgtgggtct cgcggtatca    1320
ttgcagcact ggggccagat ggtaagccct cccgtatcgt agttatctac acgacgggga    1380
gtcaggcaac tatggatgaa cgaaatagac agatcgctga gataggtgcc tcactgatta    1440
agcattggta actgtcagac caagtttact catatatact ttagattgat ttaaaacttc    1500 attttttaatt taaaaggatc taggtgaaga tcctttttga taatctcatg accaaaatcc    1560
```

```
cttaacgtga gttttcgttc cactgagcgt cagaccccgt agaaaagatc aaaggatctt    1620
cttgagatcc tttttttctg cgcgtaatct gctgcttgca aacaaaaaaa ccaccgctac    1680
cagcggtggt ttgtttgccg gatcaagagc taccaactct ttttccgaag gtaactggct    1740
tcagcagagc gcagatacca aatactgtcc ttctagtgta gccgtagtta ggccaccact    1800
tcaagaactc tgtagcaccg cctacatacc tcgctctgct aatcctgtta ccagtggctg    1860
ctgccagtgg cgataagtcg tgtcttaccg ggttggactc aagacgatag ttaccggata    1920
aggcgcagcg gtcgggctga acggggggtt cgtgcacaca gcccagcttg gagcgaacga    1980
cctacaccga actgagatac ctacagcgtg agctatgaga aagcgccacg cttcccgaag    2040
ggagaaaggc ggacaggtat ccggtaagcg gcagggtcgg aacaggagag cgcacgaggg    2100
agcttccagg gggaaacgcc tggtatcttt atagtcctgt cgggtttcgc cacctctgac    2160
ttgagcgtcg atttttgtga tgctcgtcag ggggcggag cctatggaaa aacgccagca    2220
acgcggcctt tttacggttc ctggcctttt gctggccttt tgctcacatg ttctttcctg    2280
cgttatcccc tgattctgtg gataaccgta ttaccgcctt tgagtgagct gataccgctc    2340
gccgcagccg aacgaccgag cgcagcgagt cagtgagcga ggaagcggaa gagcgcccaa    2400
tacgcaaacc gcctctcccc gcgcgttggc cgattcatta atgcagctgg cacgacaggt    2460
ttcccgactg gaaagcgggc agtgagcgca acgcaattaa tgtgagttag ctcactcatt    2520
aggcacccca ggctttacac tttatgcttc cggctcgtat gttgtgtgga attgtgagcg    2580
gataacaatt gaattcagga ggaatttaaa atgaaaaaga cagctatcgc gattgcagtg    2640
gcactggctg gtttcgctac cgtggcccag gcggccgagc tcggccatgg ctggttgggc    2700
agcgagtaat aacaatccag cggctgccgt aggcaatagg tatttcatta tgactgtctc    2760
cttggcgact agctagttta gaattcgtaa tcatggtcat agctgtttcc tgtgtgaaat    2820
tgttatccgc tcacaattcc acacaacata cgagccggaa gcataaagtg taaagcctgg    2880
ggtgcctaat gagtgagcta actcacatta attgcgttgc gctcactgcc cgctttccag    2940
tcgggaaacc tgtcgtgtta ctaatgatgg tgatggtgat ggctagtttt gtcacaagat    3000
ttgggctcaa cttcttgtc caccttggtg ttgctgggct tgtgattcac gttgcagatg    3060
taggtctggg tgcccaagct gctggagggc acggtcacca cgctgctgag ggagtagagt    3120
cctgaggact gtaggacagc cgggaaggtg tgcacgccgc tggtcagggc gcctgagttc    3180
cacgacaccg tcgccggttc ggggaagtag tccttgacca ggcagcccag ggccgctgtg    3240
cccccagagg tgctcttgga ggagggtgcc aggggaaga ccgatgggcc cttggtggag    3300
gctgcggaga cggtgaccgt ggtaccagca gaaacctggc caggctccca ggctcctcat    3360
ctatggtaca tccagcaggg ccactggcat cccagacagg ttcagtggca gtgggtctgg    3420
gacagacttc actctcacca tcagcagact ggagcctgaa gattttgcag tgtactactg    3480
tcagcagtat ggtggctcac cgtggttcgg ccaagggacc aaggtggaac tcaaacgaac    3540
tgtggctgca ccatctgtct tcatcttccc gccatctgat gagcagttga aatctggaac    3600
tgcctctgtt gtgtgcctgc tgaataactt ctatcccaga gaggccaaag tacagtggaa    3660
ggtggataac gccctccaat cgggtaactc ccaggagagt gtcacagagc aggacagcaa    3720
ggacagcacc tacagcctca gcagcaccct gacgctgagc aaagcagact acgagaaaca    3780
caaagtctac gcctgcgaag tcacccatca gggcctgagt tcgcccgtca caaagagctt    3840
caacggagga gagtgttaat tctagataat taattaggag gaatttaaaa tgaaatacct    3900
attgcctacg gcagccgctg gattgttatt actcgctgcc caaccagcca tggccgaggt    3960
```

-continued

```
gcagctgctc gagatgagcg ataaaattat tcacctgact gacgacagtt ttgacacgga   4020
tgtactcaaa gcggacgggg cgatcctcgt cgatttctgg gcagagtggt gcggtccgtg   4080
caaaatgatc gccccgattc tggatgaaat cgctgacgaa tatcagggca aactgaccgt   4140
tgcaaaactg aacatcgatc aaaaccctgg cactgcgccg aaatatggca tccgtggtat   4200
cccgactctg ctgctgttca aaaacggtga agtggcggca accaaagtgg gtgcacttgt   4260
ctaaaggtca gttgaaagag ttcctcgacg ctaacctggc gtacccgtac gacgttccgg   4320
actacggttc tactagtccg aaaccgtcta ccccaccggg ctcttcctgc ggtgccgca   4380 tcgcccgtct ggaggaaaaa gtgaaaaccc tgaaagctca gaactccgag ctggcgtcca   4440
ctgccaacat gctgcgcgaa caggtggcac agctgaaaca gaaagttatg aaccatggcg   4500
gttgtgctag tggccaggcc ggccagcacc atcaccatca ccatggcgca tacccgtacg   4560
acgttccgga ctacgcttct taggagggtg gtggctctga gggtggcggt tctgagggtg   4620
gcggctctga gggaggcggt tccggtggtg gctctggttc cggtgatttt gattatgaaa   4680
agatggcaaa cgctaataag ggggctatga ccgaaaatgc cgatgaaaac gcgctacagt   4740
ctgacgctaa aggcaaactt gattctgtcg ctactgatta cggtgctgct atcgatggtt   4800
tcattggtga cgtttccggc cttgctaatg gtaatggtgc tactggtgat ttgctggct   4860 ctaattccca aatggctcaa gtcggtgacg tgataattc accttta atg aataatttcc   4920 gtcaatattt accttccctc cctcaatcgg ttgaatgtcg ccctttttgtc tttagcgctg   4980 gtaaaccata tgaattttct attgattgtg acaaaataaa cttattccgt ggtgtctttg   5040
cgtttctttt atatgttgcc acctttatgt atgtattttc tacgtttgct aacatactgc   5100
gtaataagga gtcttaagct agctaattaa tttaagcggc cgcagatct             5149
```

<210> SEQ ID NO 61
<211> LENGTH: 18
<212> TYPE: PRT
<213> ORGANISM: artificial sequence
<220> FEATURE:
<223> OTHER INFORMATION: TPO mimetic with flanking amino acids

<400> SEQUENCE: 61

Asn Pro Ile Glu Gly Pro Thr Leu Arg Gln Trp Leu Ala Ala Arg Ala
1               5                   10                  15

Arg Gly

<210> SEQ ID NO 62
<211> LENGTH: 41
<212> TYPE: DNA
<213> ORGANISM: artificial sequence
<220> FEATURE:
<223> OTHER INFORMATION: primer

<400> SEQUENCE: 62
taggatgcgg ccgcacaggt cttttttttt tttttttttt t                      41

<210> SEQ ID NO 63
<211> LENGTH: 24
<212> TYPE: DNA
<213> ORGANISM: artificial sequence
<220> FEATURE:
<223> OTHER INFORMATION: primer

<400> SEQUENCE: 63
ccatgtaggc tgtgcccgtg gatt                                         24

<210> SEQ ID NO 64
<211> LENGTH: 24
<212> TYPE: DNA
<213> ORGANISM: artificial sequence
<220> FEATURE:
<223> OTHER INFORMATION: primer

<400> SEQUENCE: 64
ccacgggcac agcctacatg gagc                                            24

<210> SEQ ID NO 65
<211> LENGTH: 54
<212> TYPE: DNA
<213> ORGANISM: artificial sequence
<220> FEATURE:
<223> OTHER INFORMATION: nucleic acid encoding TPO mimetic peptide
      flanking sequence

<400> SEQUENCE: 65
ttgccaattg aagggccgac gctgcggcaa tggctggcgg cgcgcgcgcc tgtt           54

<210> SEQ ID NO 66
<211> LENGTH: 18
<212> TYPE: PRT
<213> ORGANISM: artificial sequence
<220> FEATURE:
<223> OTHER INFORMATION: TPO mimetic peptide with flanking sequence

<400> SEQUENCE: 66

Leu Pro Ile Glu Gly Pro Thr Leu Arg Gln Trp Leu Ala Ala Arg Ala
1               5                   10                  15

Pro Val

<210> SEQ ID NO 67
<211> LENGTH: 472
<212> TYPE: PRT
<213> ORGANISM: artificial sequence
<220> FEATURE:
<223> OTHER INFORMATION: Humanized antibody heavy chain

<400> SEQUENCE: 67

Met Lys Trp Ser Trp Val Ile Leu Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Ile Phe
            35                  40                  45

Ser Asn Tyr Trp Ile Gln Trp Val Arg Gln Ala Pro Gly Gln Gly Leu
        50                  55                  60

Glu Trp Met Gly Glu Ile Leu Pro Gly Ser Gly Ser Thr Glu Tyr Thr
65                  70                  75                  80

Glu Asn Phe Lys Asp Arg Val Thr Met Thr Arg Asp Thr Ser Thr Ser
                85                  90                  95

Thr Val Tyr Met Glu Leu Ser Ser Leu Arg Ser Glu Asp Thr Ala Val
                100                 105                 110

Tyr Tyr Cys Ala Arg Leu Pro Ile Glu Gly Pro Thr Leu Arg Gln Trp
            115                 120                 125

Leu Ala Ala Arg Ala Pro Val Trp Gly Gln Gly Thr Leu Val Thr Val
        130                 135                 140

Ser Ser Ala Ser Thr Lys Gly Pro Ser Val Phe Pro Leu Ala Pro Cys

-continued

```
            145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys
465                 470
```

<210> SEQ ID NO 68
<211> LENGTH: 1419
<212> TYPE: DNA
<213> ORGANISM: artificial sequence
<220> FEATURE:
<223> OTHER INFORMATION: nucleic acid encoding humanized antibody heavy
      chain

<400> SEQUENCE: 68

```
atgaagtgga gctgggttat tctcttcctc ctgtcagtaa ctgccggcgt ccactcccaa      60
gtccaactgg tgcaatccgg cgccgaggtc aagaagccag ggcctcagt caaagtgtcc     120 tgtaaagcta gcggctatat tttttctaat tattggattc aatgggtgcg tcaggccccc    180
```

```
gggcagggcc tggaatggat gggtgagatc ttaccgggct ctggtagcac cgaatatacc    240
gaaaatttta aagaccgtgt tactatgacg cgtgacactt cgactagtac agtatacatg    300
gagctctcca gcctgcgatc ggaggacacg gccgtctatt attgcgcgcg tttgccaatt    360
gaagggccga cgctgcggca atggctggcg cgcgcgcgcg ctgtttgggg tcaaggaacc    420
ctggtcactg tctcgagcgc ctccaccaag ggcccatccg tcttcccct ggcgccctgc    480 tccaggagca cctccgagag cacagccgcc ctgggctgcc tggtcaagga ctacttcccc    540
gaaccggtga cggtgtcgtg gaactcaggc gccctgacca gcggcgtgca caccttcccg    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttccccca aacccaagg acaccctcat gatctcccgg    840 accctgagg tcacgtgcgt ggtggtggac gtgagccagg aagacccga ggtccagttc    900 aactggtacg tggatggcgt ggaggtgcat aatgccaaga caaagccgcg ggaggagcag    960
ttcaacagca cgtaccgtgt ggtcagcgtc ctcaccgtcc tgcaccagga ctggctgaac   1020
ggcaaggagt acaagtgcaa ggtctccaac aaaggcctcc cgtcctccat cgagaaaacc   1080
atctccaaag ccaaagggca gccccgagag ccacaggtgt acaccctgcc cccatcccag   1140
gaggagatga ccaagaacca ggtcagcctg acctgcctgg tcaaaggctt ctaccccagc   1200
gacatcgccg tggagtggga gagcaatggg cagccggaga acaactacaa gaccacgcct   1260
cccgtgctgg actccgacgg ctccttcttc ctctacagca ggctaaccgt ggacaagagc   1320
aggtggcagg aggggaatgt cttctcatgc tccgtgatgc atgaggctct gcacaaccac   1380
tacacacaga agagcctctc cctgtctctg ggtaaatga                          1419
```

<210> SEQ ID NO 69
<211> LENGTH: 236
<212> TYPE: PRT
<213> ORGANISM: artificial sequence
<220> FEATURE:
<223> OTHER INFORMATION: Humanized antibody light chain

<400> SEQUENCE: 69

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gly Ala Ser
        35                  40                  45

Glu Asn Ile Tyr Gly Ala Leu Asn Trp Tyr Gln Gln Lys Pro Gly Lys
    50                  55                  60

Ala Pro Lys Leu Leu Ile Tyr Gly Ala Thr Asn Leu Ala Asp Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Asn
            100                 105                 110

Val Leu Asn Thr Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 70
<211> LENGTH: 711
<212> TYPE: DNA
<213> ORGANISM: artificial sequence
<220> FEATURE:
<223> OTHER INFORMATION: nucleic acid encoding humanized antibody light
      chain

<400> SEQUENCE: 70
atggacatga gggtccccgc tcagctcctg gggctcctgc tactctggct ccgaggtgcc      60
agatgtgata tccagatgac ccagtccccg tcctccctgt ccgcctctgt gggcgatagg     120
gtcaccatca cctgcggcgc cagcgaaaac atctatggcg cgctgaactg gtatcaacag     180
aaacccggga agctccgaa gcttctgatt tacggtgcga cgaacctggc agatggagtc      240
ccttctcgct tctctggatc cggctccgga acggatttca ctctgaccat cagcagtctg     300
cagcctgaag acttcgctac gtattactgt cagaacgttt taaatactcc gttgactttc     360
ggacagggta ccaaggtgga aataaaacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g              711

<210> SEQ ID NO 71
<211> LENGTH: 22
<212> TYPE: PRT
<213> ORGANISM: artificial sequence
<220> FEATURE:
<223> OTHER INFORMATION: EPO mimetic with random flanking amino acids
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is any amino acid
<220> FEATURE:
<221> NAME/KEY: MISC_FEATURE
<222> LOCATION: (21)..(22)
<223> OTHER INFORMATION: Xaa is any amino acid

<400> SEQUENCE: 71
```

```
Xaa Xaa Asp Tyr His Xaa Arg Met Gly Pro Leu Thr Trp Val Xaa Lys
1               5                   10                  15

Pro Leu Gly Gly Xaa Xaa
            20
```

<210> SEQ ID NO 72
<211> LENGTH: 21
<212> TYPE: DNA
<213> ORGANISM: artificial sequence
<220> FEATURE:
<223> OTHER INFORMATION: primer

<400> SEQUENCE: 72
taggatgcgg ccgcacaggt c                                        21

<210> SEQ ID NO 73
<211> LENGTH: 39
<212> TYPE: DNA
<213> ORGANISM: artificial sequence
<220> FEATURE:
<223> OTHER INFORMATION: primer

<400> SEQUENCE: 73
cacgcgcaca acacgtctag aracatccag atgacccag                     39

<210> SEQ ID NO 74
<211> LENGTH: 39
<212> TYPE: DNA
<213> ORGANISM: artificial sequence
<220> FEATURE:
<223> OTHER INFORMATION: primer

<400> SEQUENCE: 74
cacgcgcaca acacgtctag agmcatccag ttgacccag                     39

<210> SEQ ID NO 75
<211> LENGTH: 39
<212> TYPE: DNA
<213> ORGANISM: artificial sequence
<220> FEATURE:
<223> OTHER INFORMATION: primer

<400> SEQUENCE: 75
cacgcgcaca acacgtctag agccatccrg atgacccag                     39

<210> SEQ ID NO 76
<211> LENGTH: 39
<212> TYPE: DNA
<213> ORGANISM: artificial sequence
<220> FEATURE:
<223> OTHER INFORMATION: primer

<400> SEQUENCE: 76
cacgcgcaca acacgtctag agtcatctgg atgacccag                     39

<210> SEQ ID NO 77
<211> LENGTH: 39
<212> TYPE: DNA
<213> ORGANISM: artificial sequence
<220> FEATURE:
<223> OTHER INFORMATION: primer

<400> SEQUENCE: 77
cacgcgcaca acacgtctag agatattgtg atgacccag                     39

```
<210> SEQ ID NO 78
<211> LENGTH: 39
<212> TYPE: DNA
<213> ORGANISM: artificial sequence
<220> FEATURE:
<223> OTHER INFORMATION: primer

<400> SEQUENCE: 78
cacgcgcaca acacgtctag agatrttgtg atgactcag                      39

<210> SEQ ID NO 79
<211> LENGTH: 39
<212> TYPE: DNA
<213> ORGANISM: artificial sequence
<220> FEATURE:
<223> OTHER INFORMATION: primer

<400> SEQUENCE: 79
cacgcgcaca acacgtctag agaaattgtg ttgacrcag                      39

<210> SEQ ID NO 80
<211> LENGTH: 39
<212> TYPE: DNA
<213> ORGANISM: artificial sequence
<220> FEATURE:
<223> OTHER INFORMATION: primer

<400> SEQUENCE: 80
cacgcgcaca acacgtctag agaaatagtg atgacgcag                      39

<210> SEQ ID NO 81
<211> LENGTH: 39
<212> TYPE: DNA
<213> ORGANISM: artificial sequence
<220> FEATURE:
<223> OTHER INFORMATION: primer

<400> SEQUENCE: 81
cacgcgcaca acacgtctag agaaattgta atgacacag                      39

<210> SEQ ID NO 82
<211> LENGTH: 39
<212> TYPE: DNA
<213> ORGANISM: artificial sequence
<220> FEATURE:
<223> OTHER INFORMATION: primer

<400> SEQUENCE: 82
cacgcgcaca acacgtctag agacatcgtg atgacccag                      39

<210> SEQ ID NO 83
<211> LENGTH: 39
<212> TYPE: DNA
<213> ORGANISM: artificial sequence
<220> FEATURE:
<223> OTHER INFORMATION: primer

<400> SEQUENCE: 83
cacgcgcaca acacgtctag agaaacgaca ctcacgcag                      39

<210> SEQ ID NO 84
<211> LENGTH: 39
<212> TYPE: DNA
<213> ORGANISM: artificial sequence
<220> FEATURE:
<223> OTHER INFORMATION: primer
```

```
<400> SEQUENCE: 84
cacgcgcaca acacgtctag agaaattgtg ctgactcag                              39

<210> SEQ ID NO 85
<211> LENGTH: 39
<212> TYPE: DNA
<213> ORGANISM: artificial sequence
<220> FEATURE:
<223> OTHER INFORMATION: primer

<400> SEQUENCE: 85
cacgcgcaca acacgtctag agatgttgtg atgacacag                              39

<210> SEQ ID NO 86
<211> LENGTH: 22
<212> TYPE: DNA
<213> ORGANISM: artificial sequence
<220> FEATURE:
<223> OTHER INFORMATION: primer

<400> SEQUENCE: 86
attaatacga ctcactatag gg                                                22

<210> SEQ ID NO 87
<211> LENGTH: 20
<212> TYPE: DNA
<213> ORGANISM: artificial sequence
<220> FEATURE:
<223> OTHER INFORMATION: primer

<400> SEQUENCE: 87
aattaaccct cactaaaggg                                                   20

<210> SEQ ID NO 88
<211> LENGTH: 59
<212> TYPE: DNA
<213> ORGANISM: artificial sequence
<220> FEATURE:
<223> OTHER INFORMATION: primer

<400> SEQUENCE: 88
agccagccac tggcgcaggg ttgggccttc gatcgggttc ctgatgagga gctttggrg        59

<210> SEQ ID NO 89
<211> LENGTH: 59
<212> TYPE: DNA
<213> ORGANISM: artificial sequence
<220> FEATURE:
<223> OTHER INFORMATION: primer

<400> SEQUENCE: 89
agccagccac tggcgcaggg ttgggccttc gatcgggttt tgaataatga aaatagcag        59

<210> SEQ ID NO 90
<211> LENGTH: 59
<212> TYPE: DNA
<213> ORGANISM: artificial sequence
<220> FEATURE:
<223> OTHER INFORMATION: primer

<400> SEQUENCE: 90
agccagccac tggcgcaggg ttgggccttc gatcgggttg taaatgagca rcttaggag        59

<210> SEQ ID NO 91
<211> LENGTH: 59
```

<212> TYPE: DNA
<213> ORGANISM: artificial sequence
<220> FEATURE:
<223> OTHER INFORMATION: primer

<400> SEQUENCE: 91
agccagccac tggcgcaggg ttgggccttc gatcgggtta tagatgagga gcctgggmg    59

<210> SEQ ID NO 92
<211> LENGTH: 59
<212> TYPE: DNA
<213> ORGANISM: artificial sequence
<220> FEATURE:
<223> OTHER INFORMATION: primer

<400> SEQUENCE: 92
agccagccac tggcgcaggg ttgggccttc gatcgggtta taaattaggc gccttggag    59

<210> SEQ ID NO 93
<211> LENGTH: 59
<212> TYPE: DNA
<213> ORGANISM: artificial sequence
<220> FEATURE:
<223> OTHER INFORMATION: primer

<400> SEQUENCE: 93
agccagccac tggcgcaggg ttgggccttc gatcgggtta tagatyagga gctgtggag    59

<210> SEQ ID NO 94
<211> LENGTH: 58
<212> TYPE: DNA
<213> ORGANISM: artificial sequence
<220> FEATURE:
<223> OTHER INFORMATION: primer

<400> SEQUENCE: 94
agccagccac tggcgcaggg ttgggccttc gatcgggtta tagatcagga gcttagga     58

<210> SEQ ID NO 95
<211> LENGTH: 58
<212> TYPE: DNA
<213> ORGANISM: artificial sequence
<220> FEATURE:
<223> OTHER INFORMATION: primer

<400> SEQUENCE: 95
agccagccac tggcgcaggg ttgggccttc gatcgggttr tagatcagga gcttaggg     58

<210> SEQ ID NO 96
<211> LENGTH: 58
<212> TYPE: DNA
<213> ORGANISM: artificial sequence
<220> FEATURE:
<223> OTHER INFORMATION: primer

<400> SEQUENCE: 96
agccagccac tggcgcaggg ttgggccttc gatcgggtta tagatcaggg acttaggg     58

<210> SEQ ID NO 97
<211> LENGTH: 58
<212> TYPE: DNA
<213> ORGANISM: artificial sequence
<220> FEATURE:
<223> OTHER INFORMATION: primer

<400> SEQUENCE: 97
agccagccac tggcgcaggg ttgggccttc gatcgggtta tagatcaggy gcttaggg        58

<210> SEQ ID NO 98
<211> LENGTH: 59
<212> TYPE: DNA
<213> ORGANISM: artificial sequence
<220> FEATURE:
<223> OTHER INFORMATION: primer

<400> SEQUENCE: 98
ccaaccctgc gccagtggct ggctgctcgc gctcgtggtg gggtcccctc gaggttcag        59

<210> SEQ ID NO 99
<211> LENGTH: 59
<212> TYPE: DNA
<213> ORGANISM: artificial sequence
<220> FEATURE:
<223> OTHER INFORMATION: primer

<400> SEQUENCE: 99
ccaaccctgc gccagtggct ggctgctcgc gctcgtggtg gaatcccacc tcgattcag        59

<210> SEQ ID NO 100
<211> LENGTH: 59
<212> TYPE: DNA
<213> ORGANISM: artificial sequence
<220> FEATURE:
<223> OTHER INFORMATION: primer

<400> SEQUENCE: 100
ccaaccctgc gccagtggct ggctgctcgc gctcgtggtg gggtccctga ccgattcag        59

<210> SEQ ID NO 101
<211> LENGTH: 59
<212> TYPE: DNA
<213> ORGANISM: artificial sequence
<220> FEATURE:
<223> OTHER INFORMATION: primer

<400> SEQUENCE: 101
ccaaccctgc gccagtggct ggctgctcgc gctcgtggtg gcatcccagm caggttcag        59

<210> SEQ ID NO 102
<211> LENGTH: 59
<212> TYPE: DNA
<213> ORGANISM: artificial sequence
<220> FEATURE:
<223> OTHER INFORMATION: primer

<400> SEQUENCE: 102
ccaaccctgc gccagtggct ggctgctcgc gctcgtggtg gtatcccagc caggttcag        59

<210> SEQ ID NO 103
<211> LENGTH: 59
<212> TYPE: DNA
<213> ORGANISM: artificial sequence
<220> FEATURE:
<223> OTHER INFORMATION: primer

<400> SEQUENCE: 103
ccaaccctgc gccagtggct ggctgctcgc gctcgtggtg gagtsccaga yaggttcag        59

<210> SEQ ID NO 104
<211> LENGTH: 59
<212> TYPE: DNA
<213> ORGANISM: artificial sequence

```
<220> FEATURE:
<223> OTHER INFORMATION: primer

<400> SEQUENCE: 104
ccaaccctgc gccagtggct ggctgctcgc gctcgtggtg gggtcccwga cagrttcag      59

<210> SEQ ID NO 105
<211> LENGTH: 59
<212> TYPE: DNA
<213> ORGANISM: artificial sequence
<220> FEATURE:
<223> OTHER INFORMATION: primer

<400> SEQUENCE: 105
ccaaccctgc gccagtggct ggctgctcgc gctcgtggtg gggtcccatc aaggttcag      59

<210> SEQ ID NO 106
<211> LENGTH: 59
<212> TYPE: DNA
<213> ORGANISM: artificial sequence
<220> FEATURE:
<223> OTHER INFORMATION: primer

<400> SEQUENCE: 106
ccaaccctgc gccagtggct ggctgctcgc gctcgtggtg gggtcccatc tcggttcag      59

<210> SEQ ID NO 107
<211> LENGTH: 102
<212> TYPE: DNA
<213> ORGANISM: artificial sequence
<220> FEATURE:
<223> OTHER INFORMATION: oligonucleotide

<400> SEQUENCE: 107
aattcaagga gttaattatg aaaaaaaccg cgattgcgat tgcggtggcg ctggcgggct      60
ttgcgaccgt ggcccaggcg gcctctagaa tctgcggccg ca                       102

<210> SEQ ID NO 108
<211> LENGTH: 102
<212> TYPE: DNA
<213> ORGANISM: artificial sequence
<220> FEATURE:
<223> OTHER INFORMATION: oligonucleotide

<400> SEQUENCE: 108
ctagtgcggc cgcagattct agaggccgcc tgggccacgg tcgcaaagcc cgccagcgcc      60
accgcaatcg caatcgcggt ttttttcata attaactcct tg                       102

<210> SEQ ID NO 109
<211> LENGTH: 36
<212> TYPE: DNA
<213> ORGANISM: artificial sequence
<220> FEATURE:
<223> OTHER INFORMATION: primer

<400> SEQUENCE: 109
ggagtctaga taactgtggc tgcaccatct gtcttc                              36

<210> SEQ ID NO 110
<211> LENGTH: 37
<212> TYPE: DNA
<213> ORGANISM: artificial sequence
<220> FEATURE:
<223> OTHER INFORMATION: primer
```

-continued

<400> SEQUENCE: 110
aggagcggcc gcttaacact ctcccctgtt gaagctc         37

<210> SEQ ID NO 111
<211> LENGTH: 4883
<212> TYPE: DNA
<213> ORGANISM: artificial sequence
<220> FEATURE:
<223> OTHER INFORMATION: vector

<400> SEQUENCE: 111

| | |
|---|---|
| gggaaattgt aagcgttaat attttgttaa aattcgcgtt aaattttgt taaatcagct | 60 |
| catttttta ccataggcc gaaatcggca aatcccctta taaatcaaaa gaatagaccg | 120 |
| agatagggtt gagtgttgtt ccagtttgga acaagagtcc actattaaag aacgtggact | 180 |
| ccaacgtcaa agggcgaaaa accgtctatc agggcgatgg cccactacgt gaaccatcac | 240 |
| cctaatcaag ttttttgggg tcgaggtgcc gtaaagcact aaatcggaac cctaaaggga | 300 |
| gcccccgatt tagagcttga cggggaaagc cggcgaacgt ggcgagaaag gaagggaaga | 360 |
| aagcgaaagg agcgggcgct agggcgctgg caagtgtagc ggtcacgctg cgcgtaacca | 420 |
| ccacacccgc cgcgcttaat gcgccgctac agggcgcgtc aggtggcact tttcggggaa | 480 |
| atgtgcgcgg aacccctatt tgtttatttt tctaaataca ttcaaatatg tatccgctca | 540 |
| tgagacaata accctgataa atgcttcaat aatattgaaa aaggaagagt atgagtattc | 600 |
| aacatttccg tgtcgccctt attcccttttt ttgcggcatt ttgccttcct gttttttgctc | 660 |
| acccagaaac gctggtgaaa gtaaaagatg ctgaagatca gttgggtgca cgagtgggtt | 720 |
| acatcgaact ggatctcaac agcggtaaga tccttgagag ttttcgcccc gaagaacgtt | 780 |
| ttccaatgat gagcactttt aaagttctgc tatgtggcgc ggtattatcc cgtattgacg | 840 |
| ccgggcaaga gcaactcggt cgccgcatac actattctca gaatgacttg gttgagtact | 900 |
| caccagtcac agaaaagcat cttacggatg gcatgacagt aagagaatta tgcagtgctg | 960 |
| ccataaccat gagtgataac actgcggcca acttacttct gacaacgatc ggaggaccga | 1020 |
| aggagctaac cgcttttttg cacaacatgg gggatcatgt aactcgcctt gatcgttggg | 1080 |
| aaccggagct gaatgaagcc ataccaaacg acgagctgta caccacgatg cctgtagcaa | 1140 |
| tggcaacaac gttgcgcaaa ctattaactg gcgaactact tactctagct tcccggcaac | 1200 |
| aattaataga ctggatggag gcggataaag ttgcaggacc acttctgcgc tcggcccttc | 1260 |
| cggctggctg gtttattgct gataaatctg gagccggtga gcgtgggtct cgcggtatca | 1320 |
| ttgcagcact ggggccagat ggtaagccct cccgtatcgt agttatctac acgacgggga | 1380 |
| gtcaggcaac tatggatgaa cgaaatagac agatcgctga gataggtgcc tcactgatta | 1440 |
| agcattggta actgtcagac caagtttact catatatact ttagattgat ttaaaacttc | 1500 |
| atttttaatt taaaaggatc taggtgaaga tccttttga taatctcatg accaaaatcc | 1560 |
| cttaacgtga gttttcgttc cactgagcgt cagaccccgt agaaaagatc aaaggatctt | 1620 |
| cttgagatcc ttttttttctg cgcgtaatct gctgcttgca acaaaaaaa ccaccgctac | 1680 |
| cagcggtggt ttgtttgccg gatcaagagc taccaactct ttttccgaag gtaactggct | 1740 |
| tcagcagagc gcagatacca atactgtcc ttctagtgta gccgtagtta ggccaccact | 1800 |
| tcaagaactc tgtagcaccg cctacatacc tcgctctgct aatcctgtta ccagtggctg | 1860 |
| ctgccagtgg cgataagtcg tgtcttaccg ggttggactc aagacgatag ttaccggata | 1920 |
| aggcgcagcg gtcgggctga acggggggtt cgtgcacaca gcccagcttg gagcgaacga | 1980 |

-continued

```
cctacaccga actgagatac ctacagcgtg agctatgaga aagcgccacg cttcccgaag    2040
ggagaaaggc ggacaggtat ccggtaagcg gcagggtcgg aacaggagag cgcacgaggg    2100
agcttccagg gggaaacgcc tggtatcttt atagtcctgt cgggtttcgc cacctctgac    2160
ttgagcgtcg attttttgtga tgctcgtcag ggggggcggag cctatggaaa aacgccagca   2220
acgcggcctt tttacggttc ctggcctttt gctggccttt tgctcacatg ttctttcctg    2280
cgttatcccc tgattctgtg ataaccgta ttaccgcctt tgagtgagct gataccgctc    2340
gccgcagccg aacgaccgag cgcagcgagt cagtgagcga ggaagcggaa gagcgcccaa    2400
tacgcaaacc gcctctcccc gcgcgttggc cgattcatta atgcagctgg cacgacaggt    2460
ttcccgactg gaaagcgggc agtgagcgca acgcaattaa tgtgagttag ctcactcatt    2520
aggcacccca ggctttacac tttatgcttc cggctcgtat gttgtgtgga attgtgagcg    2580
gataacaatt gaattcaagg agttaattat gaaaaaaacc gcgattgcga ttgcggtggc    2640
gctggcgggc tttgcgaccg tgcccaggc ggcctctaga taactgtggc tgcaccatct    2700
gtcttcatct tcccgccatc tgatgagcag ttgaaatctg gaactgcctc tgttgtgtgc    2760
ctgctgaata acttctatcc cagagaggcc aaagtacagt ggaaggtgga taacgccctc    2820
caatcgggta actcccagga gagtgtcaca gagcaggaca gcaaggacag cacctacagc    2880
ctcagcagca ccctgacgct gagcaaagca gactacgaga aacacaaagt ctacgcctgc    2940
gaagtcaccc atcagggcct gagctcgccc gtcacaaaga gcttcaacag gggagagtgt    3000
taagcggccg cactagatat aattaaggag ataaatatga aatatctgct gccgaccgcg    3060
gcggcgggcc tgctgctgct ggcggcgcag ccggcgatgg cgctcgagct gatgagccat    3120
ggaagctgtg tcgcctgcac caggctccca cggctcgtgg tgcggtgcgc ttctggtgtt    3180
cgctgcctac agccgacacg tcgagcttcg tgcccctaga gttgcgcgtc acagcagcct    3240
ccggcgctcc gcgatatcac cgtgtcatcc acatcaatga agtagtgctc ctagacgccc    3300
ccgtggggct ggtggcgcgg ttggctgacg agagcggcca cgtagtgttg cgctggctcc    3360
cgccgcctga cacacccatg acgtctcaca tccgctacga ggtggacgtc tcggccggca    3420
acggcgcagg gagcgtacag agggtggaga tcctggaggg ccgcaccgag tgtgtgctga    3480
gcaacctgcg gggccggacg cgctacacct tcgccgtccg cgcgcgtatg gctgagccga    3540
gcttcggcgg cttctggagc gcctggtcgg agcctgtgtc gctgctgacg cctagcgacc    3600
tggaccccct catcctgacg ctctcccctca tcctcgtggt catcctggtg ctgctgaccg    3660
tgctcgcgct gctctcccac cgccgggctc tgaagcagaa gatctggcct ggcatcccga    3720
gcccagagag cgagtttgaa ggcctcttca ccacccacaa gggtaacttc cagctgtggc    3780
tgtaccagaa tgatggctgc ctgtggtgga gccccctgcac ccccttcacg gaggacccac    3840
ctgcttccct ggaagtcctc tcagagcgct gctggggac gatgcaggca gtggagccgg    3900
ggacagatga tgagggccca tcggtcttcc ccctggcacc ctcctccaag agcacctctg    3960
ggggcacagc ggccctgggc tgcctggtca aggactactt ccccgaaccg gtgacggtgt    4020
cgtggaactc aggcgccctg accagcggcg tgcacacctt cccggctgtc ctacagtcct    4080
caggactcta ctcccctcagc agcgtggtga ccgtgccctc cagcagcttg ggcacccaga    4140
cctacatctg caacgtgaat cacaagccca gcaacaccaa ggtggacaag aaagttgagc    4200
ccaaatcttg tgacaaaact cactgccagg ccggccagca ccatcaccat caccatggcg    4260
catacccgta cgacgttccg gactacgctt cttaggaggg tggtggctct gagggtggcg    4320
```

-continued

```
gttctgaggg tggcggctct gagggaggcg gttccggtgg tggctctggt tccggtgatt    4380
ttgattatga aaagatggca aacgctaata aggggctat gaccgaaaat gccgatgaaa     4440
acgcgctaca gtctgacgct aaaggcaaac ttgattctgt cgctactgat tacggtgctg   4500
ctatcgatgg tttcattggt gacgtttccg gccttgctaa tggtaatggt gctactggtg   4560
attttgctgg ctctaattcc caaatggctc aagtcggtga cggtgataat tcacctttaa   4620
tgaataattt ccgtcaatat ttaccttccc tccctcaatc ggttgaatgt cgcccttttg   4680
tctttagcgc tggtaaacca tatgaatttt ctattgattg tgacaaaata aacttattcc   4740
gtggtgtctt tgcgtttctt ttatatgttg ccacctttat gtatgtattt tctacgtttg   4800
ctaacatact gcgtaataag gagtcttaag ctagctaatt aatttaagcg gccggccgca   4860
gatctgctct ctgaggagga tct                                            4883
```

<210> SEQ ID NO 112
<211> LENGTH: 8
<212> TYPE: PRT
<213> ORGANISM: artificial sequence
<220> FEATURE:
<223> OTHER INFORMATION: part of mimetic

<400> SEQUENCE: 112

Gly Pro Thr Leu Arg Gln Trp Leu
1               5

<210> SEQ ID NO 113
<211> LENGTH: 18
<212> TYPE: PRT
<213> ORGANISM: artificial sequence
<220> FEATURE:
<223> OTHER INFORMATION: artificial CDR2
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid

<400> SEQUENCE: 113

Gly Xaa Gly Pro Thr Leu Arg Gln Trp Leu Xaa Tyr Ala Gln Lys Phe
1               5                   10                  15

Gln Gly

<210> SEQ ID NO 114
<211> LENGTH: 48
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g or t

<400> SEQUENCE: 114
cagccactgg cgcagggttg ggccmnnccc tcccatccac tcaagccc                 48

<210> SEQ ID NO 115
<211> LENGTH: 60
<212> TYPE: DNA
<213> ORGANISM: artificial sequence
<220> FEATURE:
<223> OTHER INFORMATION: primer

```
<220> FEATURE:
<221> NAME/KEY: misc_feature
<222> LOCATION: (25)..(26)
<223> OTHER INFORMATION: n is a, c, g or t

<400> SEQUENCE: 115
ggcccaaccc tgcgccagtg gctgnnktac gcacagaaat tccagggcag agtcaccatt      60

<210> SEQ ID NO 116
<211> LENGTH: 354
<212> TYPE: DNA
<213> ORGANISM: artificial sequence
<220> FEATURE:
<223> OTHER INFORMATION: nucleotides encoding variable region of light
      chain

<400> SEQUENCE: 116
gacatccaga tgacccagtc tccatcctcc ctgtctgcat ctgtaggaga cagagtcacc      60
atcacttgcc gggcgagtca gagtattagt agtttgctgg cctggtatca gcagaaacca     120
gggaaagctc ctaagctcct gatctataac ccgatcgaag gcccaaccct gcgccagtgg     180
ctggctactc gcgctcgtgg tggggtccca tcaaggttca gcggcagtgg atctgggaca     240
gatttcactc tcaccatcag cagcctgcag cctgaagatt ttgcaactta ttactgccaa     300
cagtataata gttacccctcc cactttcggc cctgggacca agtggatat caaa          354

<210> SEQ ID NO 117
<211> LENGTH: 233
<212> TYPE: PRT
<213> ORGANISM: human

<400> SEQUENCE: 117

Glu Val Gln Leu Leu Glu Gln Ser Gly Ala Glu Val Lys Lys Pro Gly
1               5                  10                  15

Ser Ser Val Lys Val Ser Cys Arg Ala Ser Gly Gly Thr Phe Asn Asn
            20                  25                  30

Tyr Ala Ile Ser Trp Val Arg Gln Ala Pro Gly Gln Gly Leu Glu Trp
        35                  40                  45

Met Gly Gly Ile Phe Pro Phe Arg Asn Thr Ala Lys Tyr Ala Gln His
    50                  55                  60

Phe Gln Gly Arg Val Thr Ile Thr Ala Asp Glu Ser Thr Gly Thr Ala
65                  70                  75                  80

Tyr Met Glu Leu Ser Ser Leu Arg Ser Glu Asp Thr Ala Ile Tyr Tyr
                85                  90                  95

Cys Ala Arg Gly Asp Thr Ile Phe Gly Val Thr Met Gly Tyr Tyr Ala
            100                 105                 110

Met Asp Val Trp Gly Gln Gly Thr Thr Val Thr Val Ser Ala Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205
```

```
Cys Asn Val Asn His Lys Pro Ser Asn Thr Lys Val Asp Lys Lys Val
        210                 215                 220

Glu Pro Lys Ser Cys Asp Lys Thr Ser
225                 230
```

<210> SEQ ID NO 118
<211> LENGTH: 212
<212> TYPE: PRT
<213> ORGANISM: human

<400> SEQUENCE: 118

```
Glu Leu Thr Gln Ser Pro Gly Thr Leu Ser Leu Ser Pro Gly Glu Arg
1               5                   10                  15

Ala Thr Leu Ser Cys Arg Ala Ser His Ser Val Ser Arg Ala Tyr Leu
            20                  25                  30

Ala Trp Tyr Gln Gln Lys Pro Gly Gln Ala Pro Arg Leu Leu Ile Tyr
        35                  40                  45

Gly Thr Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Gly Gly Ser Pro Trp Phe
                85                  90                  95

Gly Gln Gly Thr Lys Val Glu Leu Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Leu Pro Val Thr Lys Ser Phe Asn
        195                 200                 205

Arg Gly Glu Cys
    210
```

<210> SEQ ID NO 119
<211> LENGTH: 22
<212> TYPE: PRT
<213> ORGANISM: artificial sequence
<220> FEATURE:
<223> OTHER INFORMATION: TPO mimetic peptide
<220> FEATURE:
<221> NAME/KEY: MISC_FEATURE
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (20)..(21)
<223> OTHER INFORMATION: Xaa can be any naturally occurring amino acid

<400> SEQUENCE: 119

```
Gly Ile Phe Xaa Xaa Ile Glu Gly Pro Thr Leu Arg Gln Trp Leu Ala
1               5                   10                  15

Ala Arg Ala Xaa Xaa Gly
            20
```

```
<210> SEQ ID NO 120
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (35)..(36)
<223> OTHER INFORMATION: n is a, c, g or t
<220> FEATURE:
<221> NAME/KEY: misc_feature
<222> LOCATION: (38)..(39)
<223> OTHER INFORMATION: n is a, c, g or t

<400> SEQUENCE: 120
agccagccac tggcgcaggg ttgggccttc gatmnnmnng aagatccctc ccatccactc    60

<210> SEQ ID NO 121
<211> LENGTH: 60
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (34)..(35)
<223> OTHER INFORMATION: n is a, c, g or t
<220> FEATURE:
<221> NAME/KEY: misc_feature
<222> LOCATION: (37)..(38)
<223> OTHER INFORMATION: n is a, c, g or t

<400> SEQUENCE: 121
ccaaccctgc gccagtggct ggctgctcgc gctnnknnkg gcagagtcac cattaccgcg    60

<210> SEQ ID NO 122
<211> LENGTH: 215
<212> TYPE: PRT
<213> ORGANISM: artificial sequence
<220> FEATURE:
<223> OTHER INFORMATION: antibody light chain

<400> SEQUENCE: 122

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
```

```
                    145                 150                 155                 160
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
    210                 215

<210> SEQ ID NO 123
<211> LENGTH: 108
<212> TYPE: PRT
<213> ORGANISM: artificial sequence
<220> FEATURE:
<223> OTHER INFORMATION: antibody light chain variable region

<400> SEQUENCE: 123

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 124
<211> LENGTH: 249
<212> TYPE: PRT
<213> ORGANISM: artificial sequence
<220> FEATURE:
<223> OTHER INFORMATION: antibody heavy chain

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gln Leu Ile Glu Gly Pro Thr Leu Arg Gln Trp Leu Ala Ala Arg
    50                  55                  60

Ala Asn Ser Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Leu Pro Ile Glu Gly Pro Thr Leu Arg Gln Trp Leu Ala
            100                 105                 110

Ala Arg Ala Pro Val Trp Gly Gln Gly Thr Thr Val Thr Val Ser Ser
        115                 120                 125
```

```
Ala Ser Thr Lys Gly Pro Ser Val Phe Pro Leu Ala Pro Ser Ser Lys
    130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
    210                 215                 220
Lys Val Glu Pro Lys Ser Cys Asp Lys Thr His Thr Cys Pro Pro Cys
225                 230                 235                 240
Pro Ala Pro Glu Leu Leu Gly Gly Pro
                245

<210> SEQ ID NO 125
<211> LENGTH: 128
<212> TYPE: PRT
<213> ORGANISM: artificial sequence
<220> FEATURE:
<223> OTHER INFORMATION: antibody heavy chain variable region

<400> SEQUENCE: 125

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gln Leu Ile Glu Gly Pro Thr Leu Arg Gln Trp Leu Ala Ala Arg
    50                  55                  60
Ala Asn Ser Arg Val Thr Ile Thr Ala Asp Glu Ser Thr Ser Thr Ala
65                  70                  75                  80
Tyr Met Glu Leu Ser Ser Leu Arg Ser Glu Asp Thr Ala Val Tyr Tyr
                85                  90                  95
Cys Ala Arg Leu Pro Ile Glu Gly Pro Thr Leu Arg Gln Trp Leu Ala
            100                 105                 110
Ala Arg Ala Pro Val Trp Gly Gln Gly Thr Thr Val Thr Val Ser Ser
        115                 120                 125

<210> SEQ ID NO 126
<211> LENGTH: 22
<212> TYPE: PRT
<213> ORGANISM: artificial sequence
<220> FEATURE:
<223> OTHER INFORMATION: heavy chain CDR2 clone
<220> FEATURE:
<221> NAME/KEY: MISC_FEATURE
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (20)..(21)
<223> OTHER INFORMATION: Xaa can be any naturally occurring amino acid

<400> SEQUENCE: 126

Gly Ile Phe Xaa Xaa Ile Glu Gly Pro Thr Leu Arg Gln Trp Leu Ala
1               5                   10                  15
```

Ala Arg Ala Xaa Xaa Gly
            20

<210> SEQ ID NO 127
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 127

Gly Ile Phe Ser Pro Ile Glu Gly Pro Thr Leu Arg Gln Trp Leu Ala
1               5                   10                  15

Ala Arg Ala Ala Gly Gly
            20

<210> SEQ ID NO 128
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 128

Gly Ile Phe Pro Gln Ile Glu Gly Pro Thr Leu Arg Gln Trp Leu Ala
1               5                   10                  15

Ala Arg Ala Lys His Gly
            20

<210> SEQ ID NO 129
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 129

Gly Ile Phe Pro Asn Ile Glu Gly Pro Thr Leu Arg Gln Trp Leu Ala
1               5                   10                  15

Ala Arg Ala Thr Gly Gly
            20

<210> SEQ ID NO 130
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 130

Gly Ile Phe Lys Gly Ile Glu Gly Pro Thr Leu Arg Gln Trp Leu Ala
1               5                   10                  15

Ala Arg Ala Pro Gly Gly
            20

<210> SEQ ID NO 131
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 131

Gly Ile Phe Pro Pro Ile Glu Gly Pro Thr Leu Arg Gln Trp Leu Ala
1               5                   10                  15

```
Ala Arg Ala Ala Val Gly
            20

<210> SEQ ID NO 132
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 132

Gly Ile Phe Pro Arg Ile Glu Gly Pro Thr Leu Arg Gln Trp Leu Ala
1               5                   10                  15

Ala Arg Ala Lys Leu Gly
            20

<210> SEQ ID NO 133
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 133

Gly Ile Phe Pro Arg Ile Glu Gly Pro Thr Leu Arg Gln Trp Leu Ala
1               5                   10                  15

Ala Arg Ala Lys Leu Gly
            20

<210> SEQ ID NO 134
<211> LENGTH: 22
<212> TYPE: PRT
<213> ORGANISM: artificial sequence
<220> FEATURE:
<223> OTHER INFORMATION: heavy chain CDR2 clone

<400> SEQUENCE: 134

Gly Ile Phe Pro Tyr Ile Glu Gly Pro Thr Leu Arg Gln Trp Leu Ala
1               5                   10                  15

Ala Arg Ala Lys Arg Gly
            20
```

US 7,396,917 B2

RATIONALLY DESIGNED ANTIBODIES

RELATED APPLICATIONS

This application is a continuation-in-part of U.S. application Ser. No. 10/006,593 filed Dec. 5, 2001 which claims priority to U.S. Provisional Patent Application No. 60/251,448 filed Dec. 5, 2000, and to U.S. Provisional Patent Application No. 60/288,889 filed May 4, 2001, and to U.S. Provisional Patent Application No. 60/294,068 filed May 29, 2001. The disclosures of these three provisional applications are incorporated herein in their entirety by this reference.

TECHNICAL FIELD

The present invention relates to antibody molecules and biologically active peptides as diagnostic and therapeutic reagents.

BACKGROUND OF RELATED ART

Antibodies are produced by B lymphocytes and defend against infection. Antibodies are produced in millions of forms, each with a different amino acid sequence. Antibody molecules are composed of two identical light chains and two identical heavy chains. When digested by the enzyme papain, two identical Fab fragments are produced along with one Fc fragment. When digested with the enzyme pepsin one $F(ab')_2$ fragment is produced. Light and heavy chains consist of constant and variable regions. Within the variable regions are hypervariable regions (aka complementarity determining regions (CDRs)) which form the antigen binding site. The remaining parts of the variable regions are referred to as framework regions.

Important biological functions, such as receptor binding, activation and enzymatic activity, are often attributable to discrete regions of larger protein molecules, comprising a limited number of amino acid residues. Peptides displaying binding, activation or enzymatic activity have also been discovered by screening libraries of peptides generated by the random linking of amino acid residues. These peptides may not correspond to a linear arrangement of amino acids in a larger protein molecule exhibiting similar biological activity and are referred to as discontinuous peptide epitopes or mimotopes. Certain peptide mimetics have been described and cloned. See, e.g., U.S. Pat. No. 6,083,913 (thrombopoietin (TPO) mimetic), U.S. Pat. No. 5,835,382 (erythropoietin (EPO) mimetic), U.S. Pat. No. 5,830,851 (EPO mimetic) and Wrighton et al, Science, (1996) 273:458-63. Peptide epitopes and mimotopes due to their small size are potentially advantageous over large protein molecules for use as therapeutic reagents. However, the results with these peptides as therapeutics may often be unsatisfactory. One drawback to the use of peptides as therapeutic reagents is that they are generally unstable in vivo, i.e., their clearance rates from serum may be quite rapid. In addition, it is difficult to predict the activity, therapeutic or otherwise, of a peptide if it is fused into a larger molecule since conformational changes and other molecular forces may interfere with or totally negate the activity of the peptide. Attempts have been made to introduce certain polypeptides into CDR regions of antibodies. See, e.g., PCT Appln. WO 94/18221. However, as mentioned previously, due to conformational changes which may be caused by surrounding amino acids, the biological activity of active polypeptides may be diminished or negated. Therefore, it is an object herein to provide rationally designed antibodies or fragments thereof which include biologically active peptides for use as diagnostic and therapeutic reagents.

SUMMARY

Provided herein are biologically active recombinant antibodies and fragments thereof that mimic the activity of biologically active peptides, methods of making such antibodies and methods for their use in therapy and diagnosis. These antibodies and fragments thereof do not suffer from some of the disadvantages of isolated peptides, as antibodies naturally have long serum half-lives and are highly specific in binding their target. It has surprisingly been found that incorporation of particular amino acids surrounding a target peptide that has been combined into an antibody molecule actually increases the biological activity of the peptide.

Immunoglobulins or fragments thereof have a peptide of interest inserted into a complementarity determining region (CDR) of an antibody molecule. The antibody molecule serves as a scaffold for presentation of the peptide and confers upon the peptide enhanced stability. The peptide optionally replaces all the amino acids of a CDR region, or may be added to an existing CDR, whereby the original antigen specificity is disrupted, wherein the CDR region is defined by either of the two accepted schemes (See, Kabat et al., Sequences of Proteins of Immunologics Interest, $5^{th}$ ed (1991), NIH Publication 91-3242 and Chothia et al. J.Mol. Bio (1992) (227) 776-98.) Furthermore, additional amino acids may be randomly introduced which flank the peptide and allow for the screening of optimum peptide presentation in the antibody framework. It has been surprisingly found that in certain cases a proline flanking the peptide provides an increase in biological activity.

In particular embodiments an immunoglobulin molecule or fragment has amino acids residues corresponding to one complementarity determining region (CDR) replaced with amino acid residues comprising a biologically active hemopoietic or thrombopoietic peptide. In another particular embodiment, amino acid residues corresponding to at least two complementarity determining regions (CDRs) are each replaced by amino acid residues comprising such a biologically active peptide. In a single immunoglobulin molecule or fragment thereof, one or more complementarity determining regions can be replaced with a peptide; for example, CDR3 of a heavy chain, CDR3 of a light chain, CDR3 of both a heavy and light chain, CDR2 and CDR3 of a heavy chain, or CDR2 and CDR3 of a light chain. Other combinations of replaced CDR regions are possible, including the replacement of CDR1. In addition, instead of replacement of a CDR, one could add the peptide to a native CDR without actual replacement of amino acid residues while still disrupting the original antigen specificity.

Thus, in one aspect, a biologically active peptide is provided with enhanced activity by adding a proline to its carboxy terminus to form a proline-extended biologically active peptide which is used to replace or add to at least a portion of at least one CDR region in an immunoglobulin molecule or fragment thereof. In another aspect, an immunoglobulin molecule or fragment thereof is provided which has either a TPO mimetic peptide or EPO mimetic peptide as a replacement for at least one native CDR region. In this aspect, the TPO mimetic peptide or EPO mimetic peptides may optionally be proline-extended as described herein.

In further particular embodiments the immunoglobulin molecule or fragment thereof is an Fab, a ScFv, a heavy chain variable region, a light chain or a full IgG molecule. The immunoglobulin molecule or fragment thereof can also have a dimerization domain, so as to enable immunoglobulin molecules which have only one CDR replaced with a peptide to dimerize and thus activate receptors that require dimerization for activation.

In certain embodiments, the biologically active peptide can be a linear peptide epitope or a discontinuous peptide epitope. Furthermore, the biologically active peptide, when substituted for a CDR region, can have in addition to proline, one, two or more additional flanking amino acid residues proximate to the amino and/or the carboxyl termini of the peptide, which are positioned between the peptide and immunoglobulin framework region residues (i.e., at what was the junction between a CDR and the adjoining framework). The flanking amino acid residues are not typically present in the active peptide. If preferred flanking amino acid residues are already known, the flanking amino acid residues are encoded by codons which designate those specific amino acid residues. However, by initially utilizing codons, such as NNK, NNY, NNR, NNS and the like, which designate multiple amino acid residues, a collection of peptides that differ from one another merely by the flanking residues is generated. The flanking amino acid residues may determine the presentation of the peptide in the immunoglobulin molecule or fragment thereof and thus may influence the binding and/or biological activity exhibited by the peptide. This random collection of flanking amino acids allows for the selection of the best context to display the peptide sequence within the antibody framework that results in specific binding to the target molecule and the exhibition of optimal biological activity. Screening of libraries of immunoglobulins having a common peptide but different flanking amino acid residues can be carried out using binding, growth and activation assays known by those skilled in the art and as described herein.

The peptide replacing the amino acid residues comprising a CDR can be any peptide which specifically binds a target molecule and whose utility could be altered by incorporation in an antibody framework. The peptide could also exhibit a specific activity (e.g., agonist, antagonist, enzymatic, etc.). In a particular embodiment the peptide is an agonist or an antagonist for a cell surface receptor. For example, the cell surface receptor can be for a cytokine, a growth factor, or a growth inhibitor.

In particularly useful embodiments, replacement of at least a portion of a CDR with a peptide provides an antibody that acts as an agonist. The peptide used to replace at least a portion of a CDR may itself have agonist properties. Alternatively, the peptide (although specifically binding to a receptor) may not exhibit agonist activity. Rather, agonist activity might be exhibited only when the peptide is substituted for at least a portion of a CDR and is thus present in the engineered antibody. In such embodiments, the presence or absence of proline flanking the peptide is not critical, but can, in some instances, be preferred.

Thus, in one aspect the present disclosure provides for an agonist antibody comprising an antibody framework engineered to contain at least one biologically active peptide inserted at, or in place of at least a portion of, one or more CDRs. The biologically active peptide may or may not exhibit agonist activity prior to insertion into the antibody framework. In certain embodiments the antibody framework is engineered to contain two peptides capable of dimerizing with each other.

In yet another aspect, the present disclosure provides for an immunoglobulin molecule or fragment thereof comprising a region where amino acid residues corresponding to at least a portion of a complementary determining region (CDR) are replaced with a biologically active peptide, whereby the immunoglobulin molecule or fragment thereof exhibits agonist activity. The biologically active peptide may or may not exhibit agonist activity prior to insertion into the antibody framework. In particularly useful embodiments the immunoglobulin molecule or fragment thereof exhibits c-mpl agonist activity.

In yet another aspect, the present disclosure provides for an immunoglobulin molecule or fragment thereof comprising a biologically active peptide inserted at a complementary determining region (CDR), whereby the immunoglobulin molecule or fragment thereof exhibits agonist activity.

In yet another aspect, the present disclosure provides for an immunoglobulin molecule or fragment thereof comprising a region where amino acid residues corresponding to at least a portion of a complementary determining region (CDR) are replaced with a biologically active peptide, whereby the immunoglobulin molecule or fragment thereof exhibits c-mpl agonist activity.

In further particular embodiments, the peptide replacing the amino acids of a CDR is an agonist TPO mimetic peptide. One such agonist peptide has at least the sequence IEGPTLRQWLAARA (SEQ. ID. NO. 1). Other sequences are possible for TPO agonist mimetic peptides, which can be found using binding, growth and activation assays known by those skilled in the art and as described herein. Agonist TPO mimetic peptides when positioned in CDR regions can have one or more additional amino acid residues at the amino and/or carboxyl termini of the peptide which become covalently bonded to immunoglobulin framework residues. One such TPO mimetic peptide has an additional proline residue added to the carboxyl terminus; IEGPTLRQWLAARAP (SEQ. ID. NO: 2). Other immunoglobulin molecules or fragments thereof have a CDR region replaced by the TPO mimetic peptides comprising the amino acid sequence of SEQ. ID. NOs: 25, 27, 29, 31, 33, 35, 37, 39, 41, 43, 45, 47, and 49 (see FIG. 5).

Another biologically active peptide that can replace the amino acid residues of a CDR is an agonist EPO mimetic peptide. One such EPO agonist peptide has as its amino acid sequence DYHCRMGPLTWVCKPLGG (SEQ. ID. NO: 3). Other amino acid sequences are possible for EPO agonist mimetic peptides, which can be found using binding, growth and activation assays known by those skilled in the art and as described herein. Agonist EPO mimetic peptides when located in CDR regions can also have one or more additional amino acid residues at the amino and/or carboxyl termini of the peptide which become covalently bonded to immunoglobulin residues. Thus, in particular embodiments provided herein are immunoglobulin molecules (IgG) or fragments (e.g., Fab, scFv, heavy or light chains) that have a CDR region replaced with a TPO or EPO mimetic peptide. For example, the TPO peptide can include at least the sequence IEGPTLRQWLAARA (SEQ. ID. NO:1) and may further optionally have an additional proline at the immediate downstream position. The EPO mimetic encompasses at least the sequence DYHCRMGPLTWVCKPLGG (SEQ. ID. NO: 3). Likewise, it may optionally have an additional proline at the immediate downstream position.

Any immunoglobulin molecule (antibody) or fragment thereof could potentially provide the framework and have a CDR replaced with a peptide according to the present disclosure. For therapeutic or in vivo diagnostic use it is preferable that the antibody is of human origin or humanized, such as an anti-tetanus toxoid immunoglobulin. Furthermore, independent of or in conjunction with the presence of additional flanking amino acids bound to the peptide, one or more amino acid residues in other regions of the immunoglobulin, other CDR region(s) and/or framework regions, can be altered to modify the binding, activity and/or expression displayed by the peptide in the context of the immunoglobulin molecule.

It is contemplated that after construction of biologically active recombinant antibodies and/or fragments thereof, such recombinants can be subjected to randomization methods known in the art to introduce mutations at one or more points in the sequence to alter the biological activity of the antibodies. After generation of such mutants using randomization methods such as those described herein, the resulting recombinants may be assayed for activity using binding, growth, expression and activation assays.

Further provided are nucleic acid molecules encoding immunoglobulin molecules or fragments thereof which have the amino acids of one or more CDR regions replaced by a biologically active peptide. These nucleic acid molecules can be present in an expression vector, which can be introduced (transfected) into a recombinant host cell for expression of these molecules. Also provided are methods of producing an immunoglobulin molecule or fragment thereof containing a biologically active peptide, comprising culturing a recombinant host cell under conditions such that the nucleic acid contained within the cell is expressed.

Also provided are compositions, comprising an immunoglobulin molecule or fragment thereof which has amino acid residues corresponding to a CDR replaced with amino acid residues comprising a TPO or EPO mimetic peptide and a pharmaceutically acceptable carrier.

Further provided are EPO mimetic peptides with additional flanking residues which are suitable for replacement of CDRs. Also provided are nucleic acid molecules encoding these peptides.

Further provided are methods of engineering immunoglobulin molecules or fragments thereof to exhibit an agonist activity in which a biologically active peptide replaces at least a portion of one or more CDR regions of light and/or heavy chains. The methods encompass inserting a nucleic acid molecule encoding a biologically active peptide in place of at least a CDR region of a nucleic acid molecule encoding an immunoglobulin heavy or light chain or adding the molecule to the native CDR sequence and then expressing the nucleic acid molecule encoding the immunoglobulin heavy or light chain variable domain along with its complementary variable region domain, such that the two domains associate.

Further provided are methods of engineering immunoglobulin molecules or fragments thereof to exhibit an activity (property) of a biologically active TPO or EPO peptide in which a biologically active peptide replaces one or more CDR regions of light and/or heavy chains. The methods encompass inserting a nucleic acid molecule encoding a biologically active peptide in place of at least a portion of a CDR region of a nucleic acid molecule encoding an immunoglobulin heavy or light chain or adding the molecule to the native CDR sequence; and expressing the nucleic acid molecule encoding the immunoglobulin heavy or light chain variable domain along with its complementarity variable region domain, such that the two chains associate.

In another aspect, this disclosure provides a method for producing in a polypeptide a binding site capable of binding a preselected agent, the method including the steps of introducing a nucleotide sequence that codes for an amino acid residue sequence defining said binding site into a CDR region of a nucleic acid comprising an immunoglobulin heavy or light chain gene by amplifying the CDR region of the immunoglobulin gene, the introduced nucleotide sequence having the formula $-X_a-Y-X_b$, wherein X is the same or different at each occurrence and represents a randomizing trinucleotide, the sum of a and b is 4 or less and Y is a nucleotide sequence that encodes a minimum recognition domain of said binding site. In particularly useful embodiments, amplification is achieved using overlap PCR, however, any known amplification technique could be employed, such as, for example, the methods disclosed in WO94/18221, the disclosure of which is incorporated herein by reference.

In yet another aspect, this disclosure provides methods for creation of a library of monoclonal antibodies that can be screened for a desired activity. These methods of making a library include the steps of inserting a nucleic acid molecule encoding a biologically active peptide into, or in place of at least a portion of, one or more CDR regions of a nucleic acid molecule encoding an immunoglobulin heavy or light chain, providing up to a pair of randomizing trinucleotides on either side of the inserted nucleic acid molecule, and expressing a library of monoclonal antibodies. In particularly useful embodiments, a pair of randomizing trinucleotides is provided on both sides of the inserted nucleic acid molecules. The library of monoclonal antibodies thus produced can then be screened for a desired activity.

In a specific embodiment, antibodies and fragments thereof have different amino acids flanking the peptide at the amino and the carboxyl termini where the peptide becomes bound to the antibody scaffold. This, results in a population of antibody molecules or fragments thereof that may differ in the presentation of the peptide. The population is screened for those antibodies that exhibit the biological activity of the peptide. In a preferred embodiment, the amino acid immediately adjacent the peptide is a proline.

If the activity of the biologically active peptide is to activate a target molecule, this may require dimerization of two target molecules (e.g. receptors in the hematopoietic superfamilies). For dimerization to occur, two peptides must be positioned to each bind a target molecule such that the two bound target molecules can then properly associate. This can be accomplished by having two peptides present on the same antibody or fragment thereof or by causing two antibody molecules each containing one peptide to bind together. Thus, for example, a single peptide can be inserted into or substituted for at least a portion of a CDR and then expressed as an immunoglobulin or a $F(ab')_2$ fragment. As another example, two peptides can be inserted into or substituted for at least a portion of one or more CDRs and expresses as any antibody or antibody fragment.

The screening of antibodies or fragments thereof can be accomplished by panning with cells that have surface molecules to which the peptide specifically binds. Solid phase binding using purified target molecules or fragments thereof can also be used. Binding can also be carried out in solution using labeled target molecules. In addition, antibodies or fragments thereof can be screened by the use of biological assays for agonist or antagonist activity of the peptide.

Also provided are libraries of different immunoglobulin molecules or fragments thereof wherein amino acid residues corresponding to a complementarity determining region (CDR) are replaced with amino acid residues comprising a biologically active peptide which has at least one additional amino acid residue at the amino or the carboxyl terminus and the immunoglobulin molecules or fragments thereof differ by the additional amino acid residue of the peptide.

In specific embodiments the biologically active peptide is a TPO mimetic or an EPO mimetic. The antibodies of the library are displayed on phage.

Further provided are methods of stimulating proliferation, differentiation or growth of cells, which include contacting the cells with an effective amount of an immunoglobulin molecule or fragment thereof having one or more CDRs replaced with a biologically active peptide which binds to a receptor on the cells surface. In specific embodiments the biologically active peptide is a TPO mimetic or an EPO mimetic.

In other specific embodiments, is provided a method of stimulating proliferation, differentiation or growth of megakaryocytes by contacting megakaryocytes with an effective amount of an immunoglobulin molecule or fragment thereof having one or more CDRs replaced with a TPO mimetic peptide. Also provided is a method of increasing platelet production, which involves contacting megakaryocytes with an effective amount of an immunoglobulin molecule or fragment thereof having one or more CDR regions replaced with a TPO mimetic peptide. Also provided is a method of stimulating megakaryocytes and/or increasing platelet production in a patient, in which an effective amount of an immunoglobulin molecule or fragment thereof having one or more CDRs replaced with a TPO mimetic peptide is administered to a patient in need thereof. The immunoglobulin molecule and the megagakarocytes can also be contacted in vitro and the resultant cells can be introduced into the patient. In addition, an antibody or fragment thereof having at least one TPO mimetic peptide incorporated therein can be administered to a subject who intends to donate platelets, thus increasing the capacity of a donor to generate platelets to provide a more robust source of such platelets.

Also provided herein is a method of stimulating proliferation, differentiation or growth of hematopoietic cells, comprising contacting the cells with an effective amount of an immunoglobulin molecule or fragment thereof having one or more CDRs replaced with a EPO mimetic peptide.

Also embodied herein is a method of activating a homodimeric receptor protein, by contacting the receptor with an immunoglobulin molecule or fragment thereof having a CDR region replaced with a biologically active peptide that specifically binds the receptor and which has been dimerized. In a further embodiment the receptor is a thrombopoietin receptor.

DESCRIPTION OF THE DRAWINGS

FIGS. 2A and B show the sequence of the human tetanus toxoid antibody framework, light and heavy chains, respectively.

FIG. 3 is a diagram depicting the grafting of the TPO mimetic peptide AF12505 into the heavy chain CDR3 region of the tetanus toxoid framework antibody. XX represents flanking random amino acids.

Figure 1:
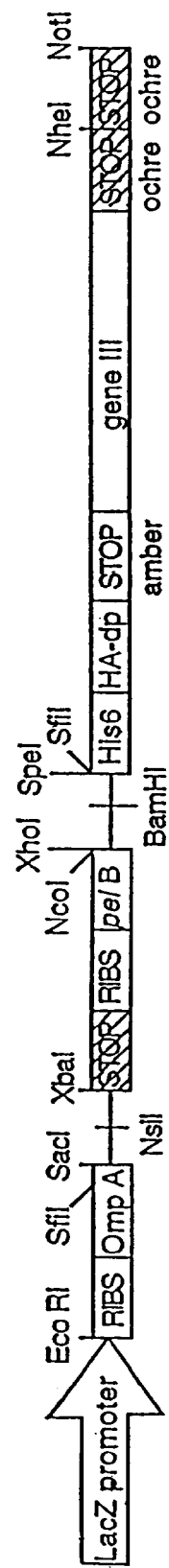
FIG. 1 is a diagrammatic representation of the vector pRL4.
Figure 4:
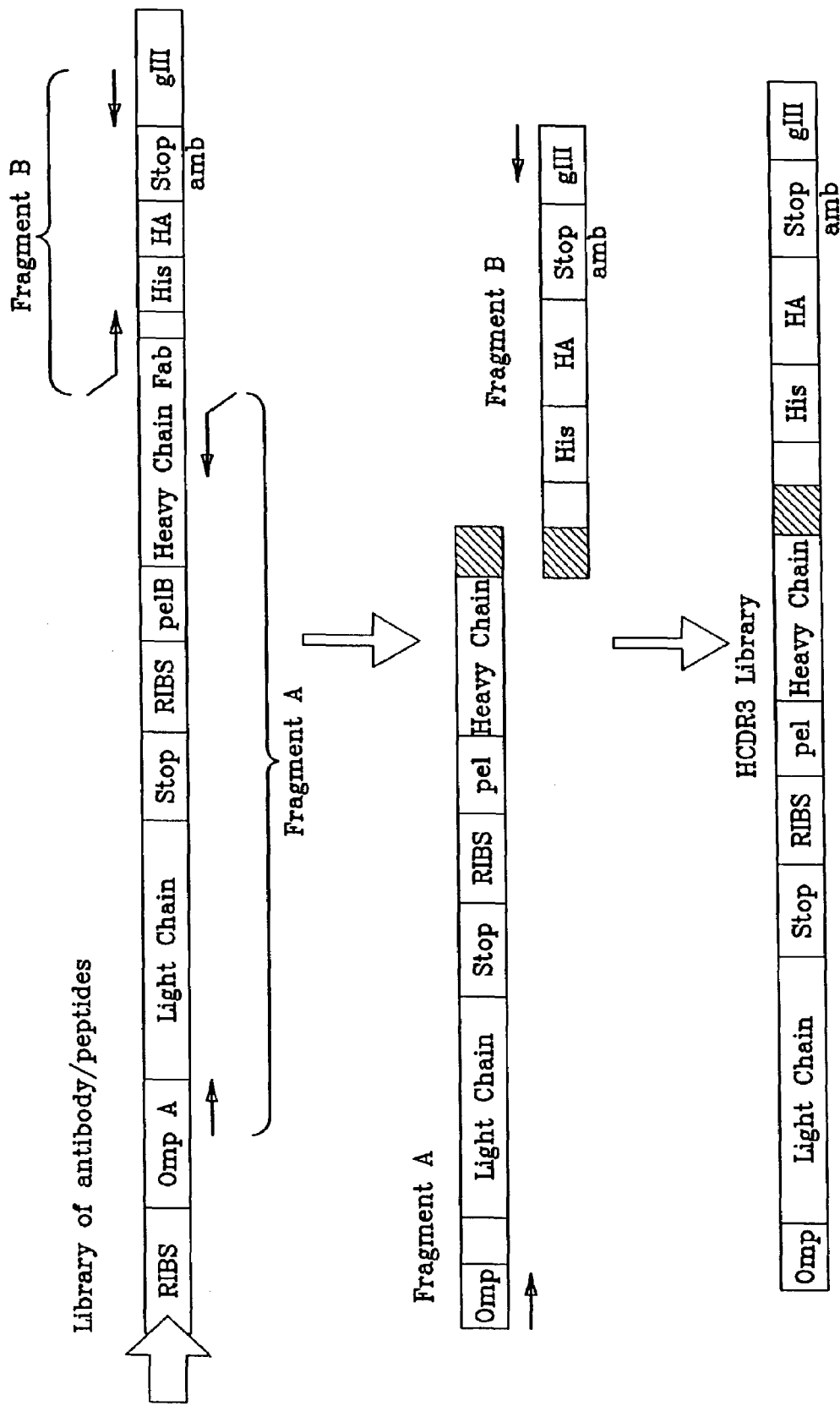
FIG. 4 is a diagram of the construction of a peptide cloned into the heavy chain CDR3 region.

FIG. 5 represents the amino acid and nucleotide sequences of clones that encode TPO mimetic peptide AF1205 with different random flanking residues.

FIGS. 6A-C depicts the nucleic acid sequence of plasmid pRL8 (SEQ. ID. NO: 60). pRL8 is a modified version of pRL4 (pRL4 is also known as pComb 3X). The pRL4 was modified between the Spe I and neighboring Sfi I restriction sites (shown by underlining) to include a flexible linker (murine kappa hinge region) followed by a Jun leucine zipper dimerization domain.

FIG. 7 is a schematic depiction of a portion of the plasmid pRL8.

FIG. 8 depicts the nucleic acid sequence of a portion of plasmid pRL8 (SEQ. ID. NO: 52) along with amino acid sequences corresponding to certain delineated nucleic acid sequences (SEQ. ID. NO: 53).

FIG. 9 is a chart showing sequences of certain TPO positive clones herein.

FIG. 10 is a bar graph showing activity of certain Fab clones containing 2 TPO mimetic peptides.

FIG. 11 is a bar graph showing activity of certain Fab clones containing 2 or 3 TPO mimetic peptides.

FIG. 12 graphically depicts the activity of Clone 59 as reflected by induction of luciferase activity.

FIG. 13A depicts the amino acid sequence and nucleic acid sequence of the 5G1.1-TPO heavy chain (SEQ. ID. NOS: 67 and 68, respectively).

FIG. 13B depicts the amino acid sequence and nucleic acid sequence of the 5G1.1 light chain (SEQ. ID. NOS: 69 and 70, respectively).

FIG. 14 is a bar graph showing FACS analysis of cMpl receptor binding of purified 5G1.1+ TPO mimetic peptide compared to parental 5G1.1 antibody.

FIG. 15 is a bar graph showing comparative activity of 5G1.1 antibody containing the TPO mimetic peptide in connection with cells transfected with a control vector containing no cMpl-R and cells transfected with a vector containing cMpl-R.

FIG. 16 shows the sequence of clone 429/Xb4 (SEQ. ID. NO: 116)

FIG. 17 is a flow chart showing the initial steps for making vector pRL5-Kappa.

FIG. 18 is a flow chart showing additional steps for making vector pRL5-Kappa.

FIG. 19 is a map of vector pRL5.

FIG. 20 is a schematic of vector pRL5-Kappa.

FIGS. 21A-I show the nucleic acid sequence of vector pRL5-Kappa.

FIG. 22 shows the amino acid sequences for the heavy and light chain of clone 116.

FIG. 23 shows the activity of clone 116.

FIG. 24 shows the sequences of heavy chain clones in accordance with an alternative embodiment of the present disclosure.

DETAILED DESCRIPTION

As used herein, "immunoglobulin" refers to an entire immunoglobulin molecule or molecules that contain immunologically active portions of whole immunoglobulin molecules and includes Fab, F(abϵ)2, scFv, Fv, heavy chain variable regions and light chain variable regions. The terms immunoglobulin and antibody are used interchangeably herein.

Any peptide that exhibits a useful property is suitable for insertion in an antibody framework. Peptide activities and uses include, but are not limited to, binding a receptor, binding a membrane bound surface molecule, binding a ligand, binding an enzyme or structural protein, activating or inhibiting a receptor, targeted drug delivery, or any enzymatic activity. Those peptides whose utility can be increased from the enhanced stability conferred upon them when presented in the context of an immunoglobulin molecule are usually selected. It should be understood that "biological activity" as used herein includes any activity associated with a molecule having activity in a biological system, including, but not limited to, the stimulatory or inhibitory activity triggered by protein-protein interactions as well as the kinetics surrounding such interactions including the stability of a protein-porotein complex. Enhancing or increasing "biological activity" herein is meant to include an increase in overall activity or an increase in any component of overall activity. It should be understood that a peptide may exhibit one biological activity (such as, e.g., simply binding to a target) before insertion into the antibody framework, and a different or enhanced biological activity (such as, e.g., agonist activity) after insertion into the antibody framework.
Figure 7:
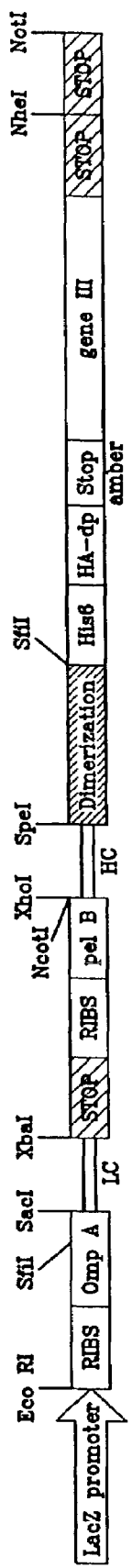
Figure 8:
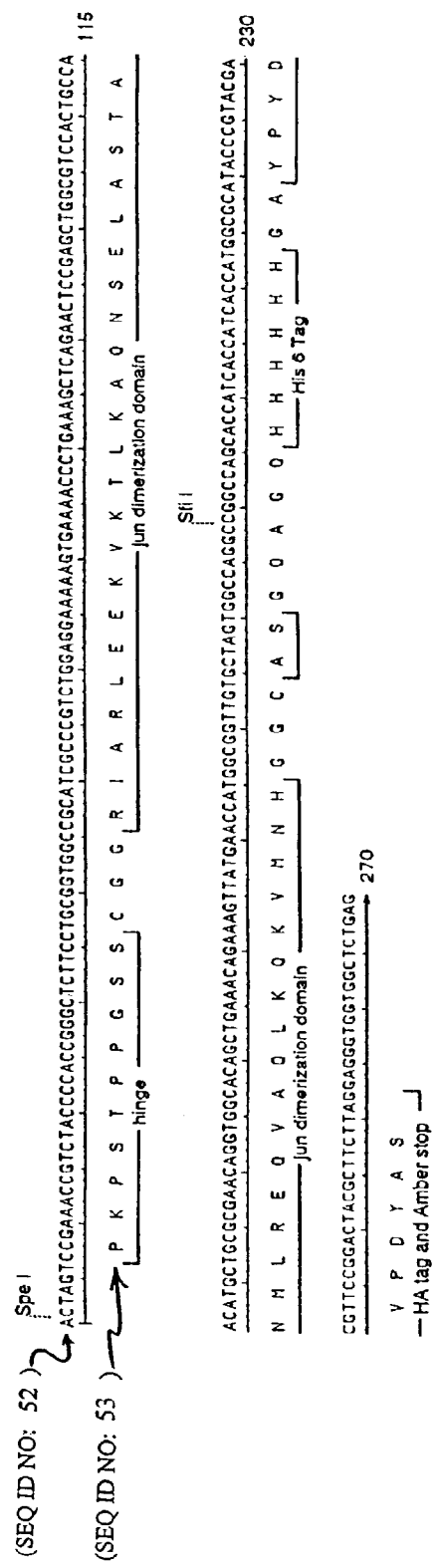
Figure 10:
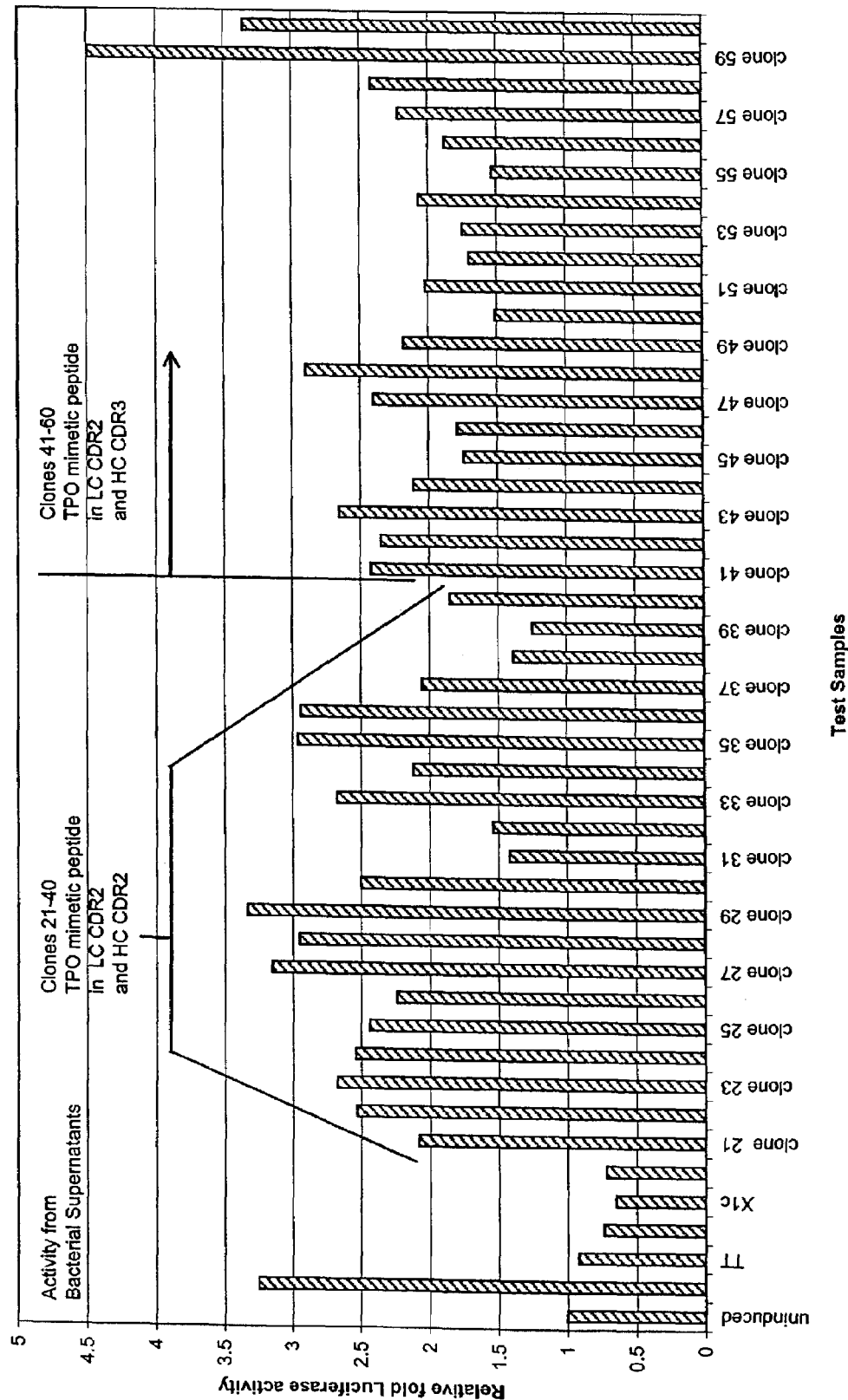
Figure 11:
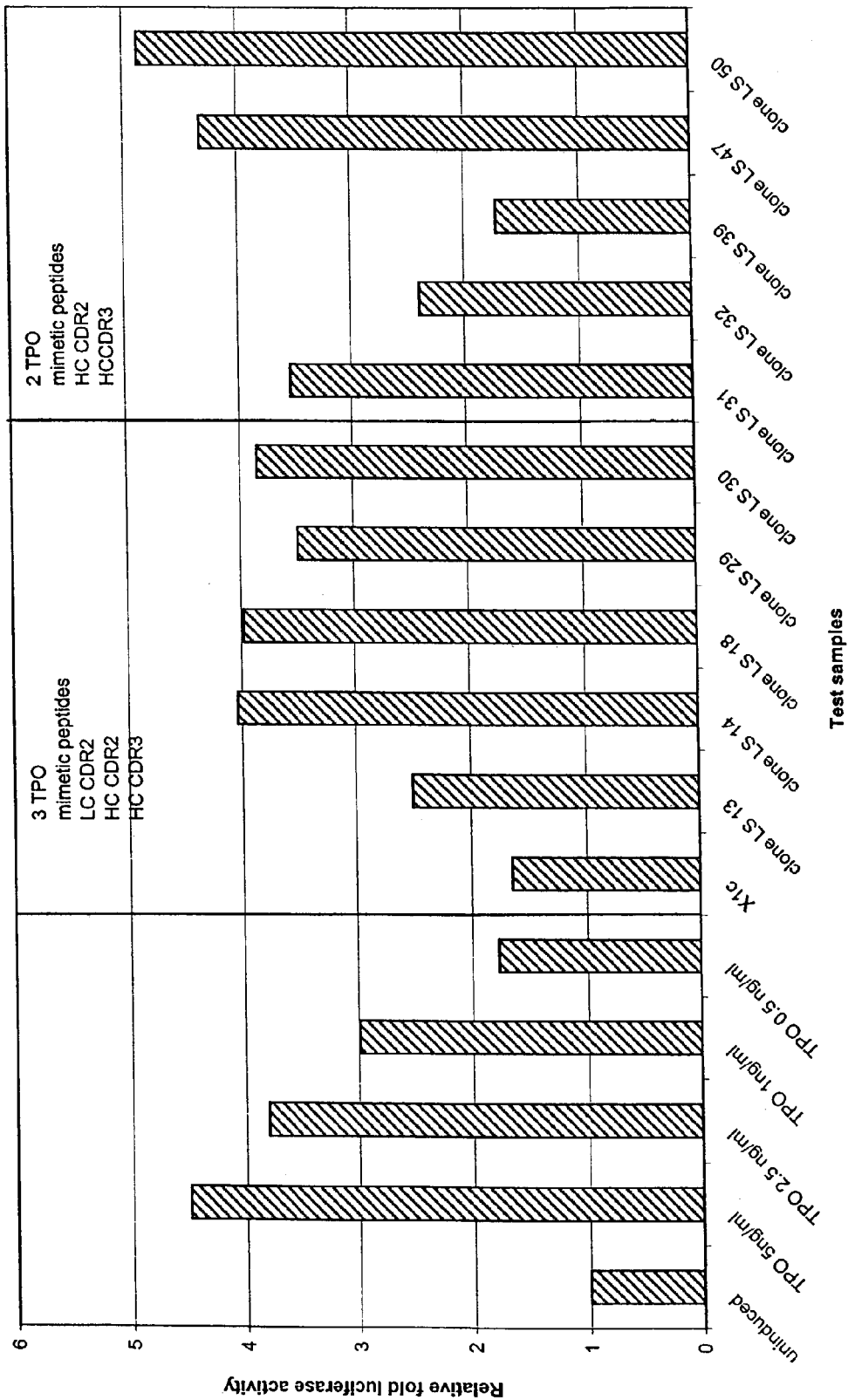
Figure 12:
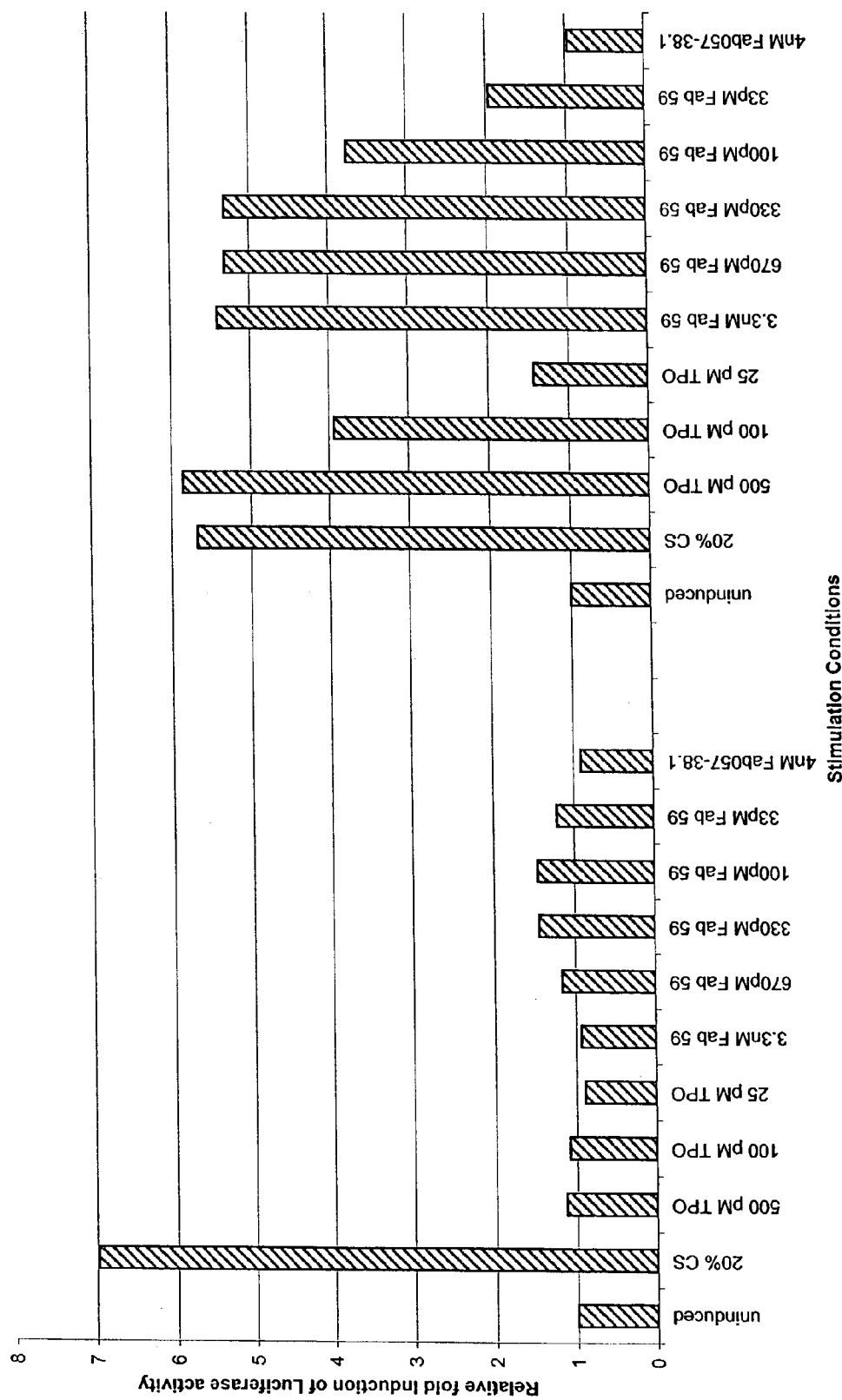

Many peptides which could benefit from display in the context of an immunoglobulin have been identified and are known to those who practice the art, e.g., EPO and TPO mimetic peptides. Other examples include peptides that bind to receptors which are activated by ligand-induced homodimerization including active fragments displaying G-CSF activity, GHR activity and prolactin activity as described in Whitty and Borysenko, *Chem Biol.*, (1999) April 6(4):R107-18; other examples of suitable peptides include a nerve growth factor mimetic from the CD loop as described in Zaccaro et al., *Med. Chem.* (2000) 43(19); 3530-40; an IL-2 mimetic as described in Eckenberg, et al., *J. Immunol.* (2000) 165(8):4312-8; glucogon-like peptide-1 as described in Evans et al., *Drugs R.D.* (1999) 2(2): 75-94; tetrapeptide I (D-lysine-L-asparaginyl-L-prolyl-L-tyrosine) which stimulates mitogen activated B cell proliferation as described in Gagnon et al., *Vaccine* (2000) 18(18):1886-92. Peptides which exhibit receptor antagonistic activity are also contemplated. For example, N-terminal peptide of vMIP-II as an antagonist of CXCR4 for HIV therapy as described in Luo et al., *Biochemistry* (2000) 39(44):13545-50; antagonist peptide ligand (AFLARAA) of the thrombin receptor for antithrombotic therapy as described in Pakala et al., *Thromb. Res.* (2000) 100(1): 89-96; peptide CGRP receptor antagonist CGRP (8-37) for attenuating tolerance to narcotics as described in Powell et al., *Br. J. Pharmacol.* (2000) 131(5): 875-84; parathyroid hormone (PTH)-1 receptor antagonist known as tuberoinfundibular peptide (7-39) as described in Hoare et al., *J. Pharmacol. Exp. Ther.* (2000) 295(2):761-70; opioid growth factor as described in Zagon et al., *Int. J. Oncol.* (2000) 17(5): 1053-61; high affinity type I interleukin 1 receptor antagonists as disclosed in Yanofsky, et al., *Proc. Natl. Acad. Sci.* USA, Vol. 93, pp. 7381-7386, July 1996 and Vigers, et al., *J. Biol. Chem.*, Vol 275, No 47, pages 36927-36933, 2000; and acid fibroblast growth factor binding peptide as described in Fan et al., *IUBMB Life* (2000) 49 (6) 545-48. Peptides can also be discovered using methods familiar to those skilled in the art. In order to identify a region of a protein that is involved in a specific biological function, a survey of the shorter peptide fragments making up that protein may reveal the linear peptide epitope responsible. Alternatively by surveying libraries of random peptides, a peptide that represents an optimal linear epitope or a discontinuous epitope may be discovered that mimics the activity of the natural protein. One method for selection is termed peptide phage-display. In this approach, a random peptide epitope library is generated so that peptides are present on the surface of a bacteriophage particle. These collections, or libraries, of peptides can then be surveyed for those able to bind to a specific immobilized target protein. (Pasqualini, R. et al., *j. Cell Biol.*, 130, 1995, 1189-1196; Wrighton, N. C., et al., *Science*, 273, 1996, pages 458-463; Cwirla, S. E., et al., *Science*, 276, 1997, pages 1696-1699; Koivunen et al, *J. Biol, Chem.*, 268, 1993, pages 20205-20210; Koivunen et al., *Bio/Technol.*, 13, 1995, pages 265-270; Healy et al., *Biochem.*, 34, 1995, pages 3948-3955; Pasqualini et al., *J. Cell Biol.*, 130, 1995, pages 1189-1196). Alternative peptide selection systems are also possible including cell surface display and ribosomal display.

Peptide mimetics used in accordance with this description are generally less than or equal to the number of amino acid residues that make up a CDR region, although they could be longer.

Any antibody can serve as a scaffold sequence, however typically human antibodies are chosen as human therapeutics is one of the ultimate objectives. Human or humanized antibodies are less likely to cause an adverse immune response in a human patient. The major criteria in selecting an antibody to serve as a framework for insertion of a peptide, is that the replacement of one or more CDRs of the antibody with the peptide must change the antigen specificity. The antibody can be a complete antibody or an Fab, scFv or F(ab')$_2$ fragment or portion thereof.

Alternatively, a library of antibodies can have one or more heavy and/or light chain CDRs replaced with a desired peptide. The resulting library can then be screened to identify antibodies having a desired activity. It should be understood that randomization with in the substituted peptide can also be provided to generate an antibody library.

A useful antibody is the anti-tetanus toxoid (TT) Fab, as it is human and because modification of the HCDR3 is sufficient to change the antigen specificity of the antibody (Barbas et al., *J. Am. Chem. Soc*., 116, 1994, pages 2161-2162 and Barbas et al., *Proc. Natl. Acad. Sci*. USA, 92, 1995, pages 2529-2533).

Grafting of the DNA sequence of the peptide of choice into an antibody so as to replace the CDR(s) of an antibody with the peptide sequence is carried out using recombinant DNA techniques known to those skilled in the art.

Examples of methods which can be utilized to graft a desired peptide having biological activity in place of a CDR region include, but are not limited to, PCR overlap, restriction enzyme site cloning, site specific mutagenesis and completely synthetic means. For a description of techniques involving overlap PCR, see, e.g., Example 1 herein. Site specific mutagenesis can be accomplished in several ways. One is based on dut/ung Kunkel mutagenesis (Kunkel, T. A., *Proc. Natl. Acad. Sci*. (1985) vol. 82, pp. 488-92). The Muta-Gene in Vitro Mutagenesis kit is available from BioRad based on this methodology (cat. #170-3581 or 170-3580). Several PCR amplification based mutagenesis approaches are also commercially available such as Stratagene's QuickChange Site-Directed Mutagenesis Kit and the ExSite PCR-based Site-Directed Mutagenesis Kit. Another non-PCR method is available from Promega as the GeneEditor in vitro Site-Directed Mutagenesis System. Completely synthetic means are also well-known and described, e.g., in Deng, et al., *Methods Mol. Biol*. (1995) 51:329-42; Kutemeler et al., *Biotechniques, (*1994) 17(2): 242-246; Shi et al., *PCR Methods Appl*., (1993) 3(1): 46-53 and Knuppik et al., *J. Mol. Biol*., (2000) 11:296 (1): 571-86 each incorporated herein by reference. In addition, the above methods used for replacing all or a portion of at least one CDR sequence can be utilized to graft a desired peptide into or adjacent to at least one native CDR sequence without replacing the original CDR sequence. In this manner, a CDR/biologically active peptide mimetic fusion construct is formed.

It is contemplated that flanking sequences may be added to the carboxyl and/or amino terminal ends of the biologically active peptide. Flanking sequences can be useful to reduce structural constraints on the grafted peptide to allow it to more easily adopt a conformation necessary for biological activity. In a preferred embodiment, a flanking region including a proline is covalently attached to the carboxy terminus of the biologically active peptide to create a proline extended biologically active peptide.

In one embodiment, a flanking region can be generated by randomizing two amino acid positions on each side of the peptide graft in order to determine the best sequence. In this manner, a library having members with multiple varied sequences can be generated. The resulting constructs are then tested for biological activity as described below by, e.g., panning techniques. Recombinant proteins can be generated that have random amino acids at specific positions. This can be accomplished by modifying the encoding DNA. When introducing randomization at a specific amino acid's codon position, a preferable deoxyribonucleotide "doping strategy" is $(NNK)_x$ in order to cover all 20 amino acids and to minimize the number of encoded stop codons. Accordingly, N may be A, C, G, or T (nominally equimolar), K is G or T (nominally equimolar), and x is typically up to about 5, 6, 7, or 8 or more, thereby producing libraries of mono-, di-, tri-, quadra-, penta-, hexa-, hepta-, and octa-peptides or more. The third position may also be G or C, designated "S". Thus, NNK or NNS (i) code for all the amino acids, (ii) code for only one stop codon, and (iii) reduce the range of codon bias from 6:1 to 3:1. There are 32 possible codons resulting from the NNK motif: 1 for each of 12 amino acids, 2 for each of 5 amino acids, 3 for each of 3 amino acids, and only one of the three stop codons. Other alternatives include, but are not limited to:

- $(NNN)_x$ which would provide all possible amino acids and all stops;
- $(NNY)_x$ eliminates all stops and still cover 14 of 20 amino acids;
- $(NNR)_x$ covers 14 of 20 amino acids; and
- $(NNS)_x$ covers all 20 amino acids and only one stop.

The third nucleotide position in the codon can be custom engineered using any of the known degenerate mixtures. However, the group NNK, NNN, NNY, NNR, NNS cover the most commonly used doping strategies and the ones used herein.

The collection of engineered antibodies that are created during this process can be surveyed for those that exhibit properties of the peptide as, e.g., phage displayed antibodies, essentially as has been described in Barbas, C. F., III, Kang, A. S., Lerner R. A., and Benkovic, S. J., Assembly of combinatorial antibody libraries on phage surfaces: the gene III site, *Proc. Natl. Acad. Sci.* USA, 88, 1991, pages 7978-7982 incorporated herein by reference. This technology allows recombinant antibodies (as complete antibodies, Fab F(ab')$_2$, or scFv) to be expressed on the surface of a filamentous bacteriophage. That same phage will have within it the genes encoding that specific antibody.

It is contemplated that any other known method of introducing randomization into a sequence may be utilized herein. For example, error prone PCR can introduce random mutations into nucleic acid sequences (See, e.g., Hawkins et al., J. Mol. Biol, (1992) 226(3): 889-96). Briefly, PCR is run under conditions which compromise the fidelity of replication, thus introducing random mutations in sequences as those skilled in the art would accomplish. After generation of such random mutants, they can be placed into phage display formats, panned and thus evaluated for activity. Likewise, particular bacteria known to provide random mutations of genes, such as *Epicurian Coli*® XL1-Red Competent cells (commercially available from Stratagen, La Jolla, Calif.), which do so during plasmid replication can be utilized to provide random mutants which are then screened for biological activity in accordance with the present disclosure.

It is also contemplated that randomization may be introduced at any point in the nucleotide sequence after incorporation of an active peptide into the antibody or fragment thereof to alter the overall biological activity of the antibody. In this manner, not only can alterations be made in the biological activity of a peptide mimetic by causing mutations within the peptide's sequence, but mutations in the surrounding scaffold can be incorporated with the resulting constructs being assayed for alterations in biological activity or expression. Indeed, it is contemplated that libraries having repertoires of multiple constructs resulting from such randomization can be generated and assayed.

Single chain libraries can be utilized in accordance with the present disclosure because an entire binding domain is contained on one polypeptide. The light chain variable region is separated from heavy chain variable region by a linker region. The use of short linkers (<11 amino acids) favors a dimeric complex where $V_H$ of one ScFv associates with $V_L$ of another ScFv molecule and visa versa, these molecules are termed diabodies (Kortt, A. A., Malky, R. L., Caldwell, J. B., Gruen, L. C., Ivanci, N., Lawrence, M. G. et al. *Eur. J. Biochem.* 221:151-157, 1994). This is because folding of monomeric ScFv is impaired with linkers <11 amino acids (Alfthan, K., Takkinen, K., Sizman, D., Soderlund, H., and Teeri, T. T. *Protein-Eng.* 8:725-731, 1995). Longer linkers (>11 amino acids) favors folding of monomeric ScFv into a single antigen binding domain, thus precluding dimer formation.

One useful phage display vector is pRL4 which is also known as pComb 3X (see FIG. 1). This vector enables display of chimeric expression products on the surface of packaged phagemid particles. pRL4 is a modified version of pComb3H (Barbas, C. F. III and Burton, D. R. 1994. Monoclonal Antibodies from Combinatorial Libraries. Cold Spring Harbor Laboratory Course Manual, Cold Spring Harbor, N.Y.; Burton, D. R.; Barbas, C. F. III. *Advances in Immunology* 57:191-280, 1994; Lang, I. M., Chuang, T. L., Barbas, C. F. 3$^{rd}$, Schleef, R. R. *J. Biol. Chem.* 271: 30126-30135, 1996; Rader and Barbas, Phage Display, A Laboratory Manual, Cold Spring Harbor Laboratory Press, Cold Spring Harbor, N.Y. (2000). The design of pRL4 allows for dimerization of scFv antigen binding domains on the phage surface and in soluble form as detailed below. When the plasmid is transformed into a supE bacterial host such as ER2537 (F' Sup E, New England Biolabs, Beverly, Mass.), the amber mutation is suppressed approximately fifty percent of the time. In this way half of the expressed scFvs are fused with the filamentous phage gene III protein (amino acids 230-406) and the other half will be terminated just prior to gene III to produce soluble scFv. Both the scFv-pIII fusion and soluble scFv products have the Omp A signal sequence and will be transported to the periplasm where they will be able to form dimeric scFv complexes, termed diabodies (Kortt, A. A., Malby, R. L., Caldwell, J. B., Gruen, L. C., Ivanci, N., Lawrence, M. C. et al. *Eur. J. Biochem.* 221: 151-157, 1994). Diabodies are expected to fold such that the $V_H$ of one scFv will pair with the $V_L$ of a second scFv-pIII resulting in divalent antibody fragments. In a non-sup E host, such as TOP10F' (InVitrogen, Carlsbad, Calif.), the amber stop codon is recognized yielding soluble scFv diabodies.

In the final single chain expression construct in pRL4, the single chain antibody fragments are cloned downstream of the *E. coli* lacZ promoter, ribosome binding site, and omp A leader sequence. These elements allow induction of expression by IPTG, and the secretion out of the cell via the omp A leader sequence when expressed in the suppressor strain ER2537. The single chain fragments are fused in frame with filamentous phage gene III (gIII) sequences (amino acids 230-406). The gIII protein product, pIII, is a minor coat protein necessary for infectivity. Upon promoter induction by IPTG, the single chain antibody-pIII fusion is synthesized and transported to the bacterial periplasmic space. In the periplasmic space, the scFv-gene III fusion proteins are inserted into the membrane. Upon superinfection with helper phage, these fragments are exported out of the cell on the surface of phage as pIII-antibody fragments. Other possible proteins to be used for fusion on the surface of phagemids include filamentous coat protein pVIII and other coat proteins.

Fab fragment libraries, that maintain the native antigen recognition site, are useful to ensure that affinity is maintained.

In the final hybrid Fab expression construct in pRL4, the light and heavy chains are cloned as a single Sfil fragment. In this way, the light chain fragments are cloned downstream of the E. coli lacZ promoter, ribosome binding site, and omp A leader sequence. These elements allow induction of expression by IPTG, and secretion out of the cell via the omp A leader sequence. The light chain fragments are followed by a stop codon, a second ribosome binding site, the E. coli pel B leader sequence and heavy chain. Hybrid heavy chain genes are fused in frame with filamentous phage gene III (gIII) sequences (amino acids 230-406). An amber stop codon is present at the fusion junction. In a sup E bacterial host such as ER2357 (New England Biolabs, Beverly, Mass.), the amber mutation is suppressed. Upon promoter induction, a single polycistronic message is transcribed and translated as two polypeptides, a light chain and a heavy chain-gene III fusion protein. Following synthesis the polypeptides are transported to the bacterial periplasmic space as directed by the leader sequences. In the periplasmic space the heavy chain-pIII fusion proteins are inserted into the membrane, and the light and heavy chains are associated covalently through disulfide bonds, forming the antigen binding sites. The human constant region CH1 and $C_L$ sequences include the cysteines that form the disulfide bond between heavy and light chains. Upon superinfection with helper phage, these fragments are exported out of the cell on the surface of phage as Fab-cpIII fusion. In a non-sup E host, such as TOP1OF' (Invitrogen, Carlsbad, Calif.), the amber stop codon is recognized yielding soluble Fab fragments. Important features of the pRL4 phage display system used include a purification His 6 tag, an HA epitope tag following the heavy chain, as well as a suppressible amber stop codon which is located between the heavy chain and the phage gene III. The HA tag is recognized by HA.11 antibody (Babco, Berkeley, Calif.) and 12CA5 antibody (Roche Molecular Biochemical, Indianapolis, Ind.). The His6 tag allows affinity purification of antibody fragments by Nickel-chelate chromatograph (Qiagen, Valencia, Calif.). The amber stop allows for quick conversion from a fusion Fab-cpIII product (for incorporation on the phage coat) when the stop is suppressed, to the soluble Fab which is made in a non-suppressor bacterial host.

Selection involves isolating from the library the best candidates that specifically bind to the peptides target molecule and display biological activity.

The phage expressing antibody fragments on their surface can be produced and concentrated so that all members of a library can be allowed to bind to the target molecule. The target molecule can be immobilized on a microtiter dish, on whole cells, the membranes of whole cells, or present in solution. Non-specific Ab-phage are washed away, and bound phage particles are released from the antigen, often by the use of low pH. The recovered Ab-phage are infectious and so can be amplified in a bacterial host. Typically, multiple rounds of this sort of selection are performed. Individual antibody fragment clones can then be analyzed as soluble Fabs or scFvs for identification of those that specifically recognize the target molecule.

Prior to any selection strategy, initial libraries are electroporated into host cells, such as ER2537. Library cultures are grown to log phase and superinfected with helper phage, such as VCSM13, a commercially available helper phage (Stratagene, La Jolla, Calif.). Superinfection provides the remaining phage components needed for packaging plasmids into phagemid particles. Alternatively, phage display without the use of helper phage may be utilized. Following overnight growth, phagemids in the culture supernate are precipitated with polyethylene glycol (PEG). PEG precipitated phage are used in panning (solid phase cell surface, internalization and membrane), FACS sorting, or magnetic sorting to purify specific binding antibodies from non specific binders.

In cell based panning, antibody-phage libraries are incubated with target cells, and the non-adherent phage are removed with multiple washes. A typical panning protocol is as follows:

1. Block phage particles with PBS+1%BSA or 10% FBS+ 4% milk powder+NaN³, (except when internalized antibodies are assayed).
2. Add target cells to blocked phages (approximately $5 \times 10^6$ cells).
3. Mix and rotate slowly at 4° C. or 37° C.
4. Wash cells twice with 1 ml ice cold PBS/1%BSA/NaN₃ or room temperature PBS/1%BSA/NaN₃.
5. Specific antibody-phage bound to cells can be eluted by low pH, for example with 76 mM citric acid ph 2.5 in PBS for 5 to 10 minutes at room temperature.
6. Neutralize eluted phage with 1M Tris-HCl pH 7.4.
7. After neutralization, antibody-phage can be used to infect ER2537 bacteria and amplify during overnight growth for the next round of panning.

Generally, 3-4 rounds of panning are performed on each library. Phage ELISAs using commercially available secondary antibody (sheep anti-M13 antibody-HRP) or soluble antibody ELISAs using a commercially available HA. 11 antibody (Babco, Berkeley, Calif.) that recognizes the HA tag incorporated into each antibody from PRL4 sequences, can be performed following each round of panning to allow estimation of the enrichment of binding antibodies over nonbinders. Following the last round of panning, the antibody-phage can be picked as single colonies from agar plates, grown as monoclonal antibody-phage and screened by ELISA for identification of specific binders. FACS analysis may also be utilized. Specifically the antibody-phage are infected into Top10F' bacteria and plated for single colonies. Single colonies are picked form agar plates, grown and induced with IPTG. Soluble antibody is screened by ELISA for identification of specific binders. Screening can be done against live cells, against intact, mildly fixed target cells, or recombinant protein(s).

Methods for whole cell panning have been described previously (Siegel, D. L., Chang, T. Y., Russell, S. L., and Bunya, V. Y. 1997. *J. Immunol. Methods* 206:73-85 incorporated herein by reference). Other techniques for selection which can be applied include fluorescent activated cell sorting (FACs). Alternative methods for selection using libraries include, but are not limited to, ribosome display and plaque hybridization to a labeled antigen.

Following panning to isolate high affinity antibody binders, bioassays for functional screens of agonist antibodies can be carried out. Dimerization is often a prerequisite for activation of many receptors and thus bioassays focus on agonist antibodies that stimulate receptors via promotion of dimerization. As previously described, single chain multivalency is approached in linker design. Fab fragment multivalency can be approached in a number of ways. A number of recent reports in the literature have shown success in dimeric antibody fragment formation which is applicable to phage display (DeKruif, J., and Logtenberg, T. 1996. *J. Biol. Chem.* 271:7630-7634, Pack, P., and Pluckthun, A. 1992. *Biochemistry* 31:1579-1584, and Holliger, P., and Winter, G. 1993. *Current Opin. Biotech.* 4:446-449). Divalent Fabs can be created in at least two ways. In one approach dimerization is achieved by addition of a dimerization domain to pRL4, forming pRL8 (See FIGS. 6A-C, 7 and 8). There are a number of dimerization domains (lexA, Zn fingers, fos, jun etc.) that can be utilized in these vectors to obtain multivalency of Fab fragments. Dimerization domains are selected from, but not limited to, the following: jun (DeKruif, J. and Logtenberg, T. *J. Biol. Chem.* 271:7630-7634, 1996; Kostelny, S. A., Cole, M. S., and Tso, J. Y. *J.Immunol.* 148:1547-1553, 1992) the LexA dimerization region (Kim, B. and Little, J. W. *Science* 255:203-206, 1992), the yeast GCN4 dimerization domain (van Heeckeren, W. J., Sellers, J. W., Struhl, K. *Nucleic Acids Res.* 20:3721-3724, 1992), Gin invertase from the bacteriophage Mu (Spaeny-Dekking, L., Schlicher, E., Franken, K., van de Putte, P., Goosen, N. *J. Bacteriol.* 34:1779-1786, 1995), *E. coli* NTRC protein dimerization domain (Klose, K. E., North, A. K., Stedman, K. M., Kustu, S. *J. Mol. Biol.* 241:233-245, 1994), and HSV-1 ICP4 dimerization domain (Gallinari, P., Wiebauer, K., Nardi, M. C., Jiricny, J. *J. Virol.* 68:3809-3820, 1994) all incorporated by reference. Also, a high temperature dimer domain from thermus organisms can be utilized (MacBeath, G., Kast, P., Hilvert, D., *Biochemistry* 37:100062-73, 1998 and MacBeath, G., Kast, P., Hilvert, D., *Science* 279: 1958-61, 1998). These are functional domains that when incorporated into a molecule allow for dimerization to occur. In addition, dimerization can be achieved in cells through the use of full IgG vectors, or dimerization domains such as CH3 dimerization domains. Those of ordinary skill in the art are familiar with these and other dimerization domains and their use to dimerize proteins.

Additional methods that may be utilized to generate antibody constructs which contain at least two binding sites are known. The antibody or antibody fragments created by each of these approaches could be utilized for testing agonistic antibody activity as described in Example 1 below for whole IgG produced in mammalian cells. These methods include chemical dimerization of Fab, pegylation of Fab, production of Fab'2, generation of whole IgG in bacterial cells, and use of diabodies (scFvs). Importantly, any of the antibody forms generated for analysis of agonistic activity could be used as the final therapeutic product.

Chemical dimerization may be also achieved using a variety of chemical crosslinking reagents. For example, SMCC (Succinimidyl trans-4 (maleimidylmethyl) cyclohexane-1-carboxylate) from Molecular Probes (Eugene, Oreg.), Cat #S-1534. This reagent will modify primary amino groups in the antibody. After incubating the antibody with the SMCC at room temperature, the reaction is run over a PD-10 column. This maleimide derivitized Fab can be added to either a second Fab or a separate batch of the same Fab that has been treated with TCEP [(Tris(2-carboxyethyl) phosphine, hydrochloride): Molecular Probes Cat #T-2556] to reduce the thiol groups to SH. The reduction reaction is carried out in the dark for 15 minutes. The conjugation of the maleimide Fab and the thiol reduced Fab occurs at a 1:1 ratio. Dimers are isolated by passing the reaction over a sephadex 200 gel filtration column. Other chemical linkers known to those skilled in the art may be used for dimerization. Production of an Fab' that has an extra cysteine residue engineered into the hinge region has been described, e.g., in U.S. Pat. No. 5,677,425 and Carter, et al., *BioTechnology*, Vol 10, February 1992, pages 163-167 the disclosures of which are hereby incorporated by reference. That thiol site can be used for conjugation to moieties such as polyethyleneglycol (PEG). Pegylation technology is known, for example, see Koumenis et al, Int. J. Pharm. (2000) 198(1): 83-95, incorporated herein by reference, which makes it possible to link two Fab' molecules together using PEG coupling.

Technology for bacterially producing Fab'2 involves cloning the human IgG hinge region, and optionally part of the CH2, as part of the Fd which includes additional cysteines and is described, e.g., in Better, et al., PNAS USA (1993) 90(2): 457-61, incorporated herein by reference. The additional thiol groups on the Fd hinge can interact and cause two Fab' molecules to dimerize, creating a Fab'2. Fab'2 can be purified directly from the bacterial cells. Additionally, undimerized Fab' from the bacteria can be isolated and chemically converted to Fab'2.

As described earlier, the variable regions of the antibody can be cloned as a single chain wherein the variable light (VL) is connected to the variable heavy (VH) by a linker region. If that linker region is short (for example 5-7 amino acids), the folding of the scFv will favor association of two scFvs where the VL of one scFv paris with the VH of the second scFv. In this manner, two antigen binding sites are presented on the diabody.

Antibody constructs which contain two binding sites may be generated using any of these methods in order to test agonist activity and/or be used as the final therapeutic product.

Following the panning or sorting steps of Fab libraries, the library of panned molecules are restricted with Sac I and Spe I and cloned into pRL8. Subcloning to pRL8 vector individually or en masse following FACS sorting or panning allows expression of dimeric soluble binding Fabs for analysis in bioassays. In pRL8, the antibody fragments are transported to the periplasmic space and form dimers there. The advantage of this approach is that it permits panning of monomeric Fab fragments, favoring high affinity Fabs.

Another approach uses a secondary antibody. pRL4 has the hemagglutinin decapeptide tag recognized by the commercially available HA. 11 antibody (Babco, Berkeley, Calif.). Fabs identified in FACS sorting or panning to be tested in bioassay are preincubated with HA. 11 which will promote dimerization, prior to addition to bioassays.

Once binding scFv's or Fabs are identified by panning or another selection method, the individual clones, each expressing a unique dimerized antibody fragment on the phage surface are tested for proliferation, differentiation, activation or survival effects on target cells. In addition, soluble dimerized antibody are examined in bioassays.

Biological Assays for Screening for TPO-Like Activity

1. Colony formation assays—Megakaryocytic colonies from bone marrow (Megacult C Kit from Stem Cell Technologies Inc., Vancouver BC, Canada).

2. Proliferation assays—proliferation of Ba/F3 cells (Cwirla et al. 1997, Science, Vol. 276 pages 1696-1699). The Ba/F3-mpl cell line was established (F. de Sauvage et al., Nature, 369:533 (1994)) by introduction of the cDNA encoding the entire cMpl receptor into the IL-3 dependent murine lymphobiastoid cell line Ba/F3. Stimulation of proliferation of Ba/F3-mpl cells in response to various concentrations of antibodies or TPO was measured by the amount of incorporation of $^3$H-thymidine as previously described (F. de Sauvage et al., supra).

3. Phosphorylation assays—phosphorylation of JAK2 (Drachman et al., J. Biol. Chem., (1999), Vol. 274, pages 13480-13484).

4. Transcriptional based assays—Transiently co-transfect full length cMpl receptor with c-Fos promoter luciferase reporter construct. 24 hour post transfection starve the cells in 0.5% FCS for 24 hours. Stimulate the cells, harvest after 6 hours and take luciferase readings (see also Example 1, Biological Assays section).

Biological Assays for Screening for EPO-Like Activity

1. Bone marrow erthroid colony formation in Methylcellulose (Wrighton et al., Science, 1996, Vol. 273 pages 458-463).

2. TF-1 cell (Human erythroleukemia cell line) proliferation. TF-1 cells express both full length and a truncated form of the Epo-R. (J.Cell Physiol., 1989, Vol 140, pages 323-334).

3. The EPO receptor couples directly to JAK2 kinase to induce tyrosine phosphorylation. Epo induces cFos in TF-1 cells. c-Fos transcriptional activation. (Witthuhn et al., Cell, (1993), Vol. 74, pages 227-236).

A number of bioassays can be used in high-throughput screening. Those of ordinary skill in the art are familiar with these and other suitable bioassays. Several non-radioactive assays have been developed in which either DNA synthesis or enzyme activity can be analyzed. For example, an MTT cell proliferation assay (Promega Corporation, Madison, Wis.) that is based on an assay described by Mosmann (Mossman, T. 1983. *J. Immunol. Methods* 65:55-57 incorporated herein by reference) can be used. This protocol is fast and easy. In the assay, MTT (3-[4,5-dimethylthiazol-2-yl]-2,5-diphenyl-tetrazolium bromide), a tetrazolium salt, is converted into a blue formazan product by mitochondrial dehydrogenase activity in living cells. The dehydrogenase content, and therefore the amount of colored product produced, is proportional to cell number. The colored product is detectable in an ELISA plate reader at 570 nm. Assays are performed in triplicate, en masse in 96 well microtiter plates. Briefly, target cells are plated in 100 μl aliquots in culture medium in 96-well plates. Following addition of various concentrations of antibodies, cells are incubated for 48-72 hours at 37° C. and 5% $CO_2$ in a fully humidified atmosphere. MTT is added to each well, and proliferation monitored via ELISA plate reader.

For example, in proliferation assays using TF-1 cells, bacterial cells containing phagemids expressing antibodies are grown overnight at 37° C. in 96 well deep well plates in 1 ml of a media that is a mixture of mammalian cell media and bacterial media (in the case of TF-1 cells: RPMI 2.7/SB 0.3/Carb 100 μg/ml). TF-1 cells are a human bone marrow erythroleukemia cell line that responds to multiple cytokines (Kitamura, T., Tange, T., Terasawa, T., Chiba, S., Kuwaki, T., Miyagawa, K., Piao, Y. F., Miyazono, K., Urabe, A., Takaku, F., *Cell Physiol*. 140:323-334, 1989; Kitamura, T., Tojo, A., Kuwaki, T., Chiba, S., Miyazono, K., Urabe, A., Takaku, F., 8*lood* 73:375-380, 1989; Kitamura, T., Takaku, F., Miyajima, A., *Int. Immunol*. 3:571-577, 1991) On the following day, the overnight cultures are subcultured ⅒ to fresh trays, and placed at 37° C. for 2 hours. Following induction with IPTG at 37° C. for 4 hours, the plates are centrifuged at 2000 rpm/15' at room temperature. 50 ul each culture supernate are filtered in 96 well filter trays (Millipore) to sterile 96 well assay plates. Mammalian cells are prewashed to remove growth factor and resuspended at a concentration of $1 \times 10^5$ cells/ml. 50 ul cells are added to each well. Assay plates are incubated in 37° C./5% $CO_2$ incubator for 72 hours. At 72 hours, the trays are developed by adding 40 ul media/MTS/PMS per well. MTS is an improved more soluble version of MTT. Both assays are based on the cellular conversion of tetrazolium salt. A MTS proliferation assay kit (catalogue number G5421) can be purchased from Promega, Inc. (Madison, Wis.). Plates are kept at 37°/$CO_2$ incubator and read at $OD_{490}$ at 1 hour, 4 hours, 8 hours with microplate reader.

The activities of cytokines are often synergistic. Synergy could be manifested through the binding of ligands to two different receptors which then sends the correct signal, or via a priming effect whereby interaction of ligand/receptor primes the cell to respond to a second cytokine. Furthermore, cytokines that act early in lineage development are more often synergistic than cytokines that act at later stages in a developmental pathway. Therefore, suboptimal concentrations of growth factors can be used in these bioassays to examine synergism. Conditions for suboptimal concentrations are determined for each assay. This is done by adding serial dilutions of growth factors, individually and as a mixture, to the assays and determining the levels below which a single factor does not promote a response compared to the mixture, and the level below which the mixture does not promote a response in the bioassay. Bone marrow stromal cells can also be added in bioassays to provide other necessary factors that may play a role in a synergistic response.

In addition, cell proliferation can be examined by monitoring DNA synthesis. A non-radioactive, colorimetric assay that examines 5-bromo-2'-deoxy-uridine (BrdU) incorporation (Roche Molecular Biochemicals, Indianapolis, Ind.) can be performed in microtiter plate format. Here, cells are cultured in 96-well plates and incubated with BrdU and suboptimal concentrations of cytokines. The amount of BrdU is determined after labeling with a peroxidase labeled anti-BrdU antibody. Final results are analyzed by ELISA plate reader at 405 nm.

A radioactive mitogenesis assay that measures the rate of DNA synthesis as an indication of proliferation (Raines and Ross, *Methods of Enzymol*. 109: 749-773, 1985) can also be used. In these assays, changes in rate of incorporation of [$^3$H]-thymidine in target cells is examined. Again, these assays permit concurrent and rapid screening of many antibody fragments. They have been widely used as a convenient method of assessing the stimulatory and inhibitory effects on the growth of many different cells. Cells are cultured in suspension until they reach exponential growth rate. Cells are then washed free of the medium in which they were cultured, and replated in fresh medium. Cells are aliquoted into 96 well plates in a total volume of 100 ul at a concentration of about $1-2 \times 10^5$ cells/ml. Dilutions of phage supernatant, soluble dimerized Fab or ScFv antibodies are added and cells are incubated for 18-48 hours in a gassed $CO_2$ incubator at a temp of 37° C. Following incubation, [$^3$H]thymidine (937 kBq) is added to each well and incubated for a further 4 hours. The cells are then removed from the incubator and counted directly in a bench top microplate scintillation counter such as Packard Top Count NXT Instrument (Packard, Meriden, Conn.). Alternatively cells can be serially transferred to GF/C filters on a Millipore cell harvester (Millipore, Bedford, Mass.) or similar apparatus. Radioactivity associated with acid-insoluble material retained on the filter is then determined. Dilutions of commercially available growth factors are applied to positive control wells. Negative controls would include supernatants from cells carrying non-insert containing plasmids or irrelevant antibodies treated similarly. The relative growth promoting activities of the standard and the diluents of the phage supernatants under test are compared to quantify the growth promoting activity in the sample.

Activation can be tested for by assaying second messengers or by transcriptional readout assays.

Survival can be assayed, for example, by monitoring apoptosis using assays such as tunnel assays or by other methods known to those who practice the art.

Other useful assays to analyze cellular signal transduction, the activity of kinases and phosphatases and ultimately cellular activities as a result of agonist activity include measurement of the generation of second messengers, e.g. cAMP, Ca++, diacylglycerol (DAG), and inositol 1,4,5-triphosphate (IP3). Measurement of spikes in intracellular calcium concentration, intracellular pH and membrane potential in high throughput screening assays can be performed using instruments such as the FLIPR Fluormetric Imaging Plate Reader System (Molecular Devices, Sunnyvale, Calif.). A number of fluorescent probes are available for examination of second messenger concentrations (Molecular Probes, Eugene Oreg.). Measurement of concentrations of second messengers can also be done on the single cell level (DeBernardi, M. A. and Brooker, G. *Proc. Natl. Acad. Sci* USA 93:4577-4582, 1996). In addition, assays that examine other signaling events such as phosphorylation, apoptosis or levels of RNA or protein of specific genes would be useful. For example. most cytokines have been shown to activate the enzyme PI 3-K (reviewed in Silvennoinen, O., Ihle, J. N. Signaling by the Hematopoietic Cytokine Receptors, R. G. Landes company, Austin, Tex. 1996). Furthermore, the Jak family of tyrosine kinases have been shown to be central mediators for cytokine receptor signaling (Ihle, J. N., Witthuhn, B. A., Quelle, F. W *Annu. Rev. Immunol.* 13:369-398, 1995). In addition, several other tyrosine kinases, e.g., members of the Src family, are activated in response to certain cytokine stimulations. In the case of RNA or proteins, e.g., c-Jun and c-Fos are rapidly and transiently upregulated upon cytokine stimulation, while c-Myc induction is slower. These proteins are required for G1 transition and proliferation (reviewed in Silvennoinen, O., Ihle, J. N. Signaling by Hematopoietic Cytokine Receptors, R. G. Landes Company, Austin, Tex. 1996). High throughput screens that detect increases in these transcripts could be utilized.

In transcriptional read out assays, changes in the transcription of specific genes are observed following exposure of cells to a growth factor' or growth factor mimetic (agonist or inhibitory antibody). For example, in a myc read-out assay, cells such as IL-3 dependent FDCP-mix cell line is starved of IL-3 growth factor for 8 hours, followed by exposure to growth factor mimetics, or native growth factors for 2 hours at 37° C. At this time, the cells are harvested, RNA is isolated, and reverse transcriptase-polymerase chain reactions (RT-PCR) are performed with primers specific for the myc gene. The RT-PCR reactions are electrophoresed in horizontal agarose gels for quantitation of PCR product. In this case expression of a single gene is being monitored.

Alternatively assay for changes in expression of genes can be monitored using CHIP technology, agonist antibodies could be identified under conditions of high probe sensitivity and a dynamic range. In this way, up to 10,000 or more could be analyzed for changes in expression. Desired genes that could be monitored could include c-myc, c-jun, NF-κB, among others. These genes are downstream of various signal transduction pathways and their expression should change upon a mitogenic response. In one type of commercially available CHIP (Affymetrix, Santa Clara, Calif.), oligonucleotides from desired test genes can be printed out onto glass surface. Target cells are exposed to test agonist antibodies. RNA is isolated from the cells exposed to test agonist antibodies, copied to cDNA, and in vitro transcribed in the presence of biotin. Hybridization of in vitro transcribed, biotinylated mRNA is used as probe in the arrays. Chips are then scanned to determine genes that show increases in transcription upon exposure to test agonist antibodies. In another version of CHIP technology (Incyte, Palo Alto, Calif.), the amount of DNA is not normalized on the glass, therefore, one would set up a competitive hybridization. RNA is isolated from the cells before and after exposure to agonist. cDNA is made from each sample whereby one cDNA reaction has one label incorporated, for example, Cy-3, and the other cDNA population has a different label incorporated, for example Cy-5. Signals are detected and compared on a dual laser scan to collect images.

Visual assays can also be used such as traditional methylcellulose colony forming assays (Stem Cell Technologies, Vancouver BC, Canada). In these assays, colony growth, and morphological changes are scored via light microscope. Visual examination for proliferation or differentiation effects in semi-solid agar cultures or methylcellulose can be performed using the appropriate cell line. Williams Hematology 5 (eds. E. Beutler, M. A. Lichtman, B. S. Coller L T. J. Kipps), McGraw-Hill, Inc., pp L22-L26, 1995). Addition of methylcellulose allows clonal progeny of a single progenitor cell to stay together and facilitates the recognition and enumeration of distinct colonies. All necessary components are added to a basic methylcellulose medium (such as Iscove's MDM, BSA, (-mercaptoethanol, L-glutamine) except colony-stimulating factor supplements and test antibodies (phage supernatants, soluble antibodies) are added to see if they can substitute for growth factors. Cells in methylcellulose culture are incubated for 10-12 days following the addition of antibodies in a 37° C. humidified atmosphere of 5% $CO_2$ in air. After 10-12 days of incubation, colonies are counted using an inverted microscope. After another 8-10 days, colonies are counted again. Comparisons are made between media containing antibodies and controls with and without growth factors. In addition, colonies can be picked from methylcellulose and individual cells examined cytologically by staining with Wright's stain (see Atlas of Hematological Cytology, F. G. J. Hayhoe and R. J. Flemans, Wiley-InterScience 1970).

The receptor-binding affinities of antibody fragments can be calculated (Lfas & Johnson, 1990) from association and dissociation rate constants measured using a BIACORE surface plasmon resonance system (Pharmacia Biosensor). A biosensor chip is activated for covalent coupling of gD-mpl receptor using N-ethyl-N'''-(3-dimethylaminopropyl)-carbodiimide hydrochloride (EDC) and N-hydroxysuccinimide (NHS) according to the supplier's (Pharmacia Biosensor) instructions. gD-mpl is buffer-exchanged into 10 mM sodium acetate buffer (pH 4.5) and diluted to approximately 30 μg/mL. An aliquot (5 μL) is injected at a flow rate of 1 μL/min to achieve approximately 400 response units (RU) of coupled protein. Finally, 1M ethanolamine is injected as a blocking agent. For kinetics measurements, 1.5 serial dilutions of antibody are injected in PBS/Tween buffer (0.05% Tween-20 in phosphate buffered saline) at 25° C. using a flow rate of 20 μL/min. Equilibrium dissociation constants, $K_d$ s, from SPR measurements are calculated as $k_{off}/k_{on}$. Standard deviations, $s_{on}$ for $k_{on}$ and $s_{off}$ for $k_{off}$, are typically obtained from measurements with >4 protein concentrations ($k_{on}$) or with >7 protein concentrations ($k_{off}$). Dissociation data are fit to a simple AB->A+B model to obtain koff +/−s.d. (standard deviation of measurements). Pseudo-first order rate constant (ks) are calculated for each association curve, and plotted as a function of protein concentration to obtain kon +/−s.e. (standard error of fit).

For conversion of antibody clones into full IgGs, the coding regions for both the light and heavy chains, or fragments thereof, can be separately cloned out of a bacterial vector and into mammalian vector(s). A single vector system, such as pDR1 or its derivatives, can be used to clone both light and heavy chain cassettes into the same plasmid. Alternatively, dual expression vectors where heavy and light chains are produced by separate plasmids can be used. Mammalian signal sequences need to be either already present in the final vector(s) or appended to the 5' end of the light and heavy chain DNA inserts. This can be accomplished by initial transfer of the chains into a shuttle vector(s) containing the proper mammalian leader sequences. Following restriction enzyme digestion, the light chain and heavy chain regions, or fragments thereof, are introduced into final vector(s) where the remaining constant regions for IgG1 are provided either with or without introns. In some cases where introns are used, primer design for PCR amplifying the light and heavy chain variable regions out of pRL4 may need to include exon splice donor sites in order to get proper splicing and production of the antibodies in mammalian cells.

With either vector expression system (single or dual plasmid), the production of antibody heavy and light chains can be driven by promoters that work in mammalian cells such as, but not limited to, CMV, SV40, or IgG promoters. Additionally, the vector(s) will contain a selectable marker for growth in bacteria (such as, but not limited to, ampicillin, chloramphenicol, kanamycin, or zeocin resistance). Selectable markers for mammalian cells (such as, but not limited to, DHFR, GS, gpt, Neomyocin, or hygromyocin resistance) may also be present in the IgG vector(s), or could be provided on a separate plasmid by co-transfection.

Those of ordinary skill in the art using known techniques would be able to synthesize antibodies in other organisms such as yeast, mammalian, insect, and plants (Carlson, J. R. and Weissman, I. L., *Mol. Cell. Biol.*, 8:2647-2650, 1988; Trill, J. J., Shatzman, A. R., Ganguly, S. *Curr. Opin. Biotechnol.* 6:553-560, 1995; Hiatt, A., Cafferkey, R. Bowdish, K. *Nature* 342: 76-78, 1989).

As stated previously, antibodies made in accordance with the disclosure herein provide increased half-life (duration of action) to the activity of small peptides or peptide mimetics such as the TPO mimetic described herein. In another aspect, the serum half-life of an antibody can itself be prolonged by making derivatives that are pegylated. See, e.g., Lee, et al., Bioconjug. Chem (1999) 10(6): 973-81, incorporated herein by reference. Another advantage, e.g., of the TPO mimetic antibody described herein is that normal TPO treatment may result in generation of TPO neutralizing antibodies in patients which interfere with the activity of a patient's naturally occurring TPO. The present TPO mimetic antibody substantially reduces the likelihood that a detrimental immune response will be produced toward native TPO because it has a different amino acid sequence.

The molecules encompassed by the claims can be used in diagnostics where the antibodies or fragments thereof are conjugated to detectable markers or used as primary antibodies with secondary antibodies that are conjugated to detectable markers. Detectable markers, include radioactive and non-radioactive labels and are well-known to those with skill in the art. Common non-radioactive labels include detectable enzymes such as horseradish peroxidase, alkaline phosphatase and fluorescent molecules. Fluorescent molecules absorb light at one wavelength and emit it at another, thus allowing visualization with, e.g., a fluorescent microscope. Spectrophotometers, fluorescence microscopes, fluorescent plate readers and flow sorters are well-known and are often used to detect specific molecules which have been made fluorescent by coupling them covalently to a fluorescent dye. Fluorochromes such as green fluorescent protein, red shifted mutants of green fluorescent protein, amino coumarin acetic acid (AMCA), fluorescein isothiocyanate (FITC), tetramethylchodamine isothiocyanate (TRITC), Texas Red, Cy3.0 and Cy5.0 are examples of useful labels.

The molecules can be used in cell isolation strategies such as fluorescence-activated cell sorting (FACS) if fluorescent markers are used, In fluorescence-activated cell sorting, cells tagged with fluorescent molecules are sorted electronically on a flow cytometer such as a Becton-Dickinson (San Jose, Calif.) FACS IV cytometer or equivalent instrument. The fluorescent molecules are antibodies that recognize specific cell surface antigens. The antibodies are conjugated to fluorescent markers such as fluorescein isothiocyanate (FITC) or Phycoerythrin (PE).

Magnetic sorting is also possible. In magnetic sorting procedures, the antibody is linked directly or indirectly to magnetic microbeads. Cells are precoated with antibodies that recognize cell surface molecules, e.g., receptors involved in proliferation, differentiation, activation or survival. The antibodies are attached to magnetic beads conjugated with a secondary immunoglobulin that binds to the primary antibody displaying the peptide, such as to the HA molecular tag engineered into each antibody. The cells are then removed with a magnet. Magnetic sorting can be positive selection where cells of interest are bound by the antibody and hence the magnet, or negative selection where undesired cells are isolated onto the magnet.

Alternatively, radiolabeled antibodies can be used for diagnostic purposes.

Antibodies and fragments thereof disclosed herein are useful for the amplification of a variety of clinically relevant cell types. Treatment can be in vivo or ex vivo. For example, agonist antibodies are useful to treat patients suffering from a deficiency in a cell population caused by disease, disorder or treatment related to for example suppression of hematopoiesis where less than the normal number of cells of a given lineage or lineages are present in a patient. The following represent only some examples of the conditions that can be treated with the antibodies containing biologically active peptides disclosed herein, those who practice the art would be able to identify other diseases and conditions that would benefit from such treatment. For example, HIV-infected patients, patients undergoing chemotherapy, bone marrow transplant patients, stem cell transplant patients, and patients suffering from myeloproliferative disorders show subnormal levels of specific hematopoietic lineages.

Thrombocytopenia can be a result of chemotherapy, bone marrow transplantation or chronic disease such as idiopathic thrombocytopenia (ITP) which all result in low platelet levels. The present TPO mimetic antibodies can be used to treat such patients.

Patients undergoing renal dialysis often suffer from treatment related anemia with subnormal levels of red blood cells. In aplastic anemia, bone marrow suppression can cause pancytopenia or may affect only the red blood cells, the white cells, or the platelets. The disclosed antibodies will augment the armamentarium of therapeutic agents for these and other diseases and disorders characterized by deficiencies in specific cell populations, such as hematopoietic cells.

The molecules encompassed by the claimed invention can also be used for ex vivo proliferation and differentiation of cells. This is useful for gene therapy purposes, for example for traditional viral vector approaches, and for autologous bone marrow transplants.

In addition, certain antibodies in accordance with the present disclosure can be radiolabeled for radioimmunotherapy or conjugated to toxins to deliver such toxins to specific cell types and result in the killing of those cells.

A biologically active c-mpl agonist antibody capable of stimulating proliferation, differentiation and maturation of hematopoietic cells may be used in a sterile pharmaceutical preparation or formulation to stimulate megakaryocytopoietic or thrombopoietic activity in patients suffering from thrombocytopenia due to impaired production, sequestration, or increased destruction of platelets. Thrombocytopenia-associated bone marrow hypoplasia (e.g., aplastic anemia following chemotherapy or bone marrow transplant) may be effectively treated with the disclosed antibodies as well as disorders such as disseminated intravascular coagulation (DIC), immune thrombocytopenia (including HIV-induced ITP and non HIV-induced ITP), chronic idiopathic thrombocytopenia, congenital thrombocytopenia, myelodysplasia, and thrombotic thrombocytopenia.

The biologically active c-mpl agonist antibodies disclosed herein containing the TPO mimetic peptide may be used in the same way and for the same indications as thrombopoietin (TPO). Thrombopoietin (TPO) stimulates megakaryocytopoiesis and platelet production. These antibodies are expected to have a longer half-life than native or pegylated TPO and thus are used in indications where a longer half-life are indicated.

An example of an assay useful for determining activity of TPO mimetics is the rebound thrombocytosis assay which involves administering to mice a single injection of goat anti-mouse platelet serum to induce acute thrombocytopenia (day 0). On days 5 and 6 mice are injected with test samples. On day 8 platelet counts are determined ($^{35}$S incorporation into platelets).

EPO mimetic antibodies herein stimulate hematopoiesis in a manner similar to naturally occurring EPO. Such therapy is useful in treating conditions where red blood cell production is compromised such as in chronic renal failure. The biological activity of EPO mimetic antibodies may be determined using in vitro or in vivo assays.

One in vitro assay measures the effect of erythropoietin mimetic antibodies on erythropoiesis in intact mouse spleen cells according to the procedure of Krystal, G., *Exp. Hematol.* 11:649-660 (1983). To screen various embodiments of the EPO mimetic antibodies for activity, for example, in vitro or in vivo, the EPO mimetic antibodies can be evaluated for the extent of erythropoiesis or receptor binding. Tests to determine biological activity are well-known to those of skill in the art. For example, the biological activity of erythropoietin can be measured as described in, e.g., U.S. Pat. No. 5,614,184 and U.S. Pat. No. 5,580,853 herein incorporated by reference.

The route of antibody administration is in accord with known methods, e.g., injection or infusion by intravenous, intraperitoneal, intracerebral, intramuscular, subcutaneous, intraocular, intraarterial, intrathecal, inhalation or intralesional routes, topical or by sustained release systems as noted below. The antibody is preferably administered continuously by infusion or by bolus injection. One may administer the antibodies in a local or systemic manner.

The antibodies of the invention may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or lung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art.

Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and may include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

When used for in vivo administration, the antibody formulation must be sterile and can be formulated according to conventional pharmaceutical practice. This is readily accomplished by filtration through sterile filtration membranes, prior to or following lyophilization and reconstitution. The antibody ordinarily will be stored in lyophilized form or in solution. Other vehicles such as naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Pharmaceutical compositions suitable for use include compositions wherein one or more rationally designed antibodies are contained in an amount effective to achieve their intended purpose. More specifically, a therapeutically effective amount means an amount of antibody effective to prevent, alleviate or ameliorate symptoms of disease or prolong the survival of the subject being treated. Determination of a therapeutically effective amount is well within the capability of those skilled in the art, especially in light of the detailed disclosure provided herein. Therapeutically effective dosages may be determined by using in vitro and in vivo methods.

An effective amount of antibody to be employed therapeutically will depend, for example, upon the therapeutic objectives, the route of administration, and the condition of the patient. In addition, the attending physician takes into consideration various factors known to modify the action of drugs including severity and type of disease, body weight, sex, diet, time and route of administration, other medications and other relevant clinical factors. Accordingly, it will be necessary for the therapist to titer the dosage and modify the route of administration as required to obtain the optimal therapeutic effect. Typically, the clinician will administer antibody until a dosage is reached that achieves the desired effect. The progress of this therapy is easily monitored by conventional assays.

For any antibody containing a peptide, the therapeutically effective dose can be estimated initially from cell culture assays. For example, a dose can be formulated in animal models to achieve a circulating concentration range that includes the $EC_{50}$ as determined in cell culture (e.g., the concentration of the test molecule which promotes or inhibits cellular proliferation or differentiation). Such information can be used to more accurately determine useful doses in humans.

Toxicity and therapeutic efficacy of the antibody molecules described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Molecules which exhibit high therapeutic indices are preferred. The data obtained from these cell culture assays and animal studies can be used in formulating a range of dosage for use in human. The dosage of such molecules lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1).

Dosage amount and interval may be adjusted individually to provide plasma levels of the antibody which are sufficient to promote or inhibit cellular proliferation or differentiation or minimal effective concentration (MEC). The MEC will vary for each antibody, but can be estimated from in vitro data using described assays. Dosages necessary to achieve the MEC will depend on individual characteristics and route of administration. However, HPLC assays or bioassays can be used to determine plasma concentrations.

Dosage intervals can also be determined using MEC value. Antibody molecules should be administered using a regimen which maintains plasma levels above the MEC for 10-90% of the time, preferably between 30-90% and most preferably between 50-90%.

In cases of local administration or selective uptake, the effective local concentration of the antibody may not be related to plasma concentration.

A typical daily dosage might range from about 1 μ/kg to up to 1000 mg/kg or more, depending on the factors mentioned above. Typically, the clinician will administer the molecule until a dosage is reached that achieves the desired effect. The progress of this therapy is easily monitored by conventional assays.

Depending on the type and severity of the disease, from about 0.001 mg/kg to abut 1000 mg/kg, more preferably about 0.01 mg to 100 mg/kg, more preferably about 0.010 to 20 mg/kg of the agonist antibody might be an initial candidate dosage for administration to the patient, whether, for example, by one or more separate administrations, or by continuous infusion. For repeated administrations over several days or longer, depending on the condition, the treatment is repeated until a desired suppression of disease symptoms occurs or the desired improvement in the patient's condition is achieved. However, other dosage regimes may also be useful.

EXAMPLES

The following examples are included for illustrative purposes only and are not intended to limit the scope of the invention.

Example 1

Library Construction of TPO Mimetic Sequences Grafted into a Human Antibody Framework An agonist TPO mimetic-peptide IEGPTLRQWLAARA (SEQ. ID. NO: 1) was grafted into the anti-tetanus toxoid (TT) Fab heavy chain CDR3 (HCDR3), replacing the entire HCDR3 sequence GDTIFGVTMGYYAMDV (SEQ. ID. NO: 4). FIG. 2A shows the sequence for the human tetanus toxoid antibody employed. Two grafting approaches were taken. In the first approach the agonist peptide was inserted into the H-CDR3 region with two glycines flanking each side. This was to reduce structural constraints on the grafted peptide so that it could more easily adopt the needed conformation. In the second approach, two amino acid positions on each side of the peptide graft were randomized in order that the best presentation of the peptide could be achieved (FIG. 3). These two approaches were taken in order to determine whether the peptide alone was sufficient or if specific residues were required for proper presentation of the agonist peptide on the antibody scaffold, thereby conferring its activity to the antibody.

FIG. 4 outlines the library construction process. Briefly, the anti-tetanus toxoid Fab was amplified as two fragments. Fragment A was amplified using a forward primer (N-Omp: 5' TAT CGC GAT TGC AGT GGC ACT GGC 3') (SEQ. ID. NO: 5) that annealed to the Omp A leader for the light chain in combination with a backward primer (TPOCDR3-B: 5' GC CAG CCA TTG CCG CAG CGT CGG CCC TTC AAT YNN YNN TCT CGC ACA ATA ATA TAT GGC 3') (SEQ. ID. NO: 6) that annealed at the end of the heavy chain framework region (FR) 3. The reverse primer contained a tail encoding the new CDR3. Fragment B was generated using a forward primer (TPOCDR3-F: 5'CCG ACG CTG CGG CAA TGG CTG GCG GCG CGC GCG NNY NNY TGG GGC CAA GGG ACC ACC GT 3')(SEQ. ID. NO:7) that annealed at the FR4 and the reverse primer Seq-G3Rev (5' TCA AAA TCA CCG GAA CCA GAG C 3') (SEQ. ID. NO: 8) which annealed in the gene III region of the plasmid, downstream of the heavy chain stop signal. The TPOCDR3-F primer also had a tail of bases that encoded the new CDR3 region. TAQ DNA Polymerase (Perkin Elmer) was used in the following PCR program: 94° 30 seconds, then 30 cycles of 94° for 15 sec, 55° for 15 seconds, and 72° for 90 seconds, followed by an extension period at 72° for 10 minutes, and a hold at 4°. After the fragments were generated by PCR and gel purified, they were combined for an overlap extension PCR. The new CDR3 primer encoded regions were complementary and provided 23 bases of overlap. Primers N-Omp and SeqG3Rev were used in the overlap PCR protocol to generate the full Fab DNA product. Taq DNA Polymerase (Perkin Elmer) was used in the following PCR program: 94° 30", then 20 cycles of 94° 30", 56° 30", and 72° 3'15", then an extension period of 72° for 15' followed by a 4° hold. After gel purification of the Fab product, an Sfi 1 digest was performed at 50° for 5 hours. Inserts were ligated into Sfi 1 digested pRL4 vector overnight. Ligation products were ethanol precipitated, resuspended in $H_2O$, and then electroporated into competent ER2537 bacteria (suppressor strain, New England Biolabs). Following one hour of shaking in 5 mls SOC, an equal volume of SB was added. Carbenicillin was added to 20 ug/ml and the culture shaken for one hour at 37°, followed by one hour at 37° in 50 ug/ml carbenicillin. The library culture was transferred into a flask containing 100 mls fresh SB, 50 ug/ml Carbenicillin, and $10^{12}$ VCS M13 helper phage. After two hours at 37°, kanamycin was added to select for those bacteria that had been infected with helper phage. The following day, the overnight cultures were spun down and the phage in the supernate were precipitated on ice using 4% PEG/0.5 M NaCl. After spinning down the phage, the pellet was resuspended in 1%BSA/PBS, filtered and dialyzed against PBS. Library phage were stored at 4°.

The construction of Fabs containing the non-randomly linked peptide was performed as described above by substituting primers TPOCDR3-B and TPOCDR3-F with alternate specific primers. For PP-(IEGPTLRQWLAARA)-GG (SEQ. ID. NO: 25) grafted antibody, primers used were TPOCDR3g-B (5' GC CAG CCA TTG CCG CAG CGT CGG CCC TTC AAT NGG NGG TCT CGC ACA ATA ATA TAT GGC 3') (SEQ. ID. NO: 9) and TPOCDR3g-F (5' CCG ACG CTG CGG CAA TGG CTG GCG GCG CGC GCG GGN GGN TGG GGC CAA GGG ACC ACC GT 3')(SEQ. ID. NO: 10). For GG-(IEGPTLRQWLAARA)-GG (SEQ. ID. NO: 29) grafted antibody, primers used were

```
TPO-CDR3-ggB  (5'GC CAG CCA TTG CCG CAG CGT CGG CCC TTC AAT NCC (SEQ. ID. NO:11)
              NCC TCT CGC ACA ATA ATA TAT GGC 3') and TPOCDR3g-F    (5'CCG ACG CTG CGG CAA TGG CTG GCG GCG CGC GCG GGN(SEQ. ID. NO:12)
              GGN TGG GGC CAA GGG ACC ACC GT 3').
```

Selection of the TPO Mimetic Peptide Heavy Chain CDR3 Library

In order to select for the optimal peptide display, panning was performed on human platelets. Because platelets express approximately 1800 TPO receptors per cell on their surface (cMpl receptors), they represented a good cell target. In addition, platelets are readily available from a local Blood Bank. To 1 ml of concentrated indated human platelets from the Blood Bank, 50 uls of freshly prepared Fab-phage were added in a 15 ml conical tube with 0.1% $NaN_3$. The tube was mixed at room temperature for 1-2 hours. Typically, 10 mls of 50% human serum (taken off the remaining platelets)+50%{IMDM/10% FBS/0.1% azide/2 mM EDTA} was added to the phage/cells. Platelets were pelleted at 5500×g for 5 minutes at room temperature. Supernatant was drained and the pellet was left resting under ~500 uls of the wash for 20 minutes. The platelets were very gently resuspended and then 10 mls of 25% human serum (taken off the remaining platelets)+75%{IMDM/10% FBS/0.1% azide/2 mM EDTA} was added to the phage/cells. The centrifugation, pellet rest, and resuspension of the platelets was repeated. In panning rounds 3 and 4, a third wash was performed. The washed phage/cells were transferred to an eppindorf tube and spun at 5200×g. Phage were eluted from the platelets 10 minutes at room temperature using acid elution buffer (0.1 M HCl, 1 mg/ml BSA, and glycine to pH 2.2). Platelets were pelleted at max speed and the eluted phage transferred to a 50 ml conical tube, neutralized with 2M Tris Base. Phage were then allowed to infect fresh ER2537 bacteria for 15 minutes at room temperature and amplified overnight as described above. Four rounds of platelet panning were performed.

After the fourth round of panning, pools of 3 Fab clones expressed as soluble proteins in nonsuppressor bacterial strain TOP10F' (Invitrogen, Carlsbad, Calif.) were tested by Facs for binding to platelets by utilizing the Fabs' HA epitope tag with rat high affinity anti-HA followed by anti-Rat-FITC (Sigma, St. Louis, Mo.). 25 uls indated concentrated human platelets (washed once with PBS/5 mM EDTA/2% FBS) were incubated with 100 uls bacterial supernate (60 uls bacterial supernate from three pooled Fab clones were pre-incubated with 40 uls 5% Milk/PSS at 4° for 15 minutes) at room temperature for 20-30 minutes. 1 ml of FACS buffer (PBS/2% FBS/5 mM EDTA) was added and cells spun down at 5200×g for 5 minutes. Pelleted cells were resuspended in 50 uls of I:10 diluted (in PBS/1% BSA/0.1% $NaN_3$) 2° anti-HA antibody [Rat IgG anti-HA High Affinity clone 3F10 (Roche Molecular Biochemicals)] was added. After 30 minutes at room temperature, the cells were washed with 1 ml FACS buffer as above. Following centrifugation, cells were resuspended in 100 uls of 1:160 diluted (in PBS/1% BSA/0.1% $NaN_3$) 3° anti-Rat IgG-FITC antibody (Sigma) and incubated 20 minutes at room temperature in the dark. Cells were washed with 1 ml FACS buffer then resuspended in 200 uls FACS buffer for analysis. As a positive control a commercially available sheep anti-IIb/IIIa Ab followed by anti-sheep FITC was used. Many pools of Fabs were clearly positive for binding to platelets by Facs. Follow up Facs analysis was then performed to identify individual clones that bound to the platelets.

Examination of Individual Candidates by Binding Activity

Several Fabs, as bacterial supernatants, were tested for reactivity to the original antigen tetanus toxoid in order to determine if that binding specificity was retained. The antibody scaffold anti-TT Fab does bind to its antigen TT, but not to BSA. However, four TPO-mimetic peptide grafted Fab clones did not show significant binding to TT or BSA. As seen in previous experiments, the replacement of anti-TT Fab HCDR3 was sufficient to change the specificity of the antibody.

To further examine the binding capabilities of Fabs, Facs analysis was performed on CMK cells, a Megakaryocytic cell line (from German Collection of Microorganisms and Cell Cultures) which also expresses the cMpl receptor. Fab clones that bound CMK cells were then analyzed to verify that the platelet and CMK cell binding was occurring via the cMpl receptor. For that experiment, 293 EBNA cells were transfected with or without the cMpl-R, which had been cloned from Tf-1 cells by RT-PCR. $1 \times 10^6$ transfected cells were incubated with bacterial supernate from each Fab clone (pre-blocked as described above) for 20-30 minutes at room temperature. Cells were spun down at 2000 rpm for 5 minutes. Pelleted cells were resuspended in 90 uls FACS buffer (PBS/2% FBS/1 mM EDTA) then 10 uls of 2° anti-HA antibody [Rat IgG anti-HA High Affinity clone 3F10 (Boehringer Mannheim Biochemicals) was added for a final 1:10 dilution. After 20 minutes at room temperature, the cells were washed with 1 ml FACS buffer. Following centrifugation, cells were resuspended in 100 uls of 1:50 diluted (in PBS/1% BSA/0.1% $NaN_3$) 3° anti-Rat IgG-PE antibody (Research Diagnostics Incorporated, RDI) and incubated 20 minutes at room temperature in the dark. Cells were washed with 1 ml FACS buffer then resuspended in 200 uls FACS buffer for analysis. Fabs selected during panning demonstrated strong binding to cells transfected with the cMpl-R but not to control vector transfected cells lacking the cMpl-R. This indicates that cell surface binding was occurring specifically through the cMpl receptor. Anti-TT Fab does not bind to control vector or cMpl-R transfected 293 cells. However, Fab clone X1c shows a shift from 3% binding of control (non-cMpl receptor) transfected cells to 95% binding of cells expressing the cMpl-R.

Examination of Individual Candidates by Sequence

Sequence analysis of Fab clones which specifically bound to the cMpl receptor (see FIG. 5), revealed the selection of preferred amino acids at the downstream linkage site. The DNA sequence data was analyzed and the amino acid and DNA sequences are as follows:

| Clone | Binding Properties | SEQ. ID. NO | Sequence |
|---|---|---|---|
| X1a | weak | 25 | Pro Pro (14 aa peptide) Gly Gly |
| X1a-11 | weak | 27 | Gly Gly (14 aa peptide) Gly Gly |
| X1a-13 | weak | 29 | Gly Gly (14 aa peptide) Gly Gly |
| X1c | strong | 31 | Trp Leu (14 aa peptide) Pro Val |
| X2c | weak | 33 | Met Ile (14 aa peptide*) Val Gly |
| X3a | strong | 35 | Val Val (14 aa peptide) Pro Val |
| X3b | strong | 37 | Gly Pro (14 aa peptide) Pro Asp |
| X4b | strong | 39 | Leu Pro (14 aa peptide) Pro Val |
| X4c | strong | 41 | Ser Leu (14 aa peptide) Pro Ile |
| X5a | strong | 43 | Thr Met (14 aa peptide) Pro Val |
| X5c | strong | 45 | Trp Leu (14 aa peptide) Pro-Val |
| X7a | weak | 47 | Thr Arg (14 aa peptide*) Cys Ser |
| X7b | weak |  | deletion mutant this clone has lost the peptide |
| X7c | strong | 49 | Gln Thr (14 aa peptide) Pro Asp |

All clones which demonstrated strong binding, were found to contain a proline just downstream of the 14 amino acid TPO mimetic peptide. Selection by panning of a proline in the downstream linker position represents determination of a surprising amino acid choice which confers improved binding characteristics to the grafted TPO mimetic peptide. Weak binders did not contain this proline although they still contained the TPO mimetic peptide. It should be noted that clone X7a had a silent mutation in this peptide (GCG to GCA retaining the Ala at position 11 in the peptide) and that clone X2c had a mutation in this peptide switching a Thr for Ala at position 11 of the peptide.

Biological Assays

Clones were tested for agonist activity using a transcriptional based assay measuring luciferase activity driven by the c-Fos promoter. Dimerization of the cMpl receptor activates Jak which stimulates the MAP kinase pathway. Thus activation can be measured by assaying luciferase production and activity stimulated by MAP kinase via the cFos promoter. Since dimerization of the cMpl receptor is required for activation, either full IgG or dimerized Fab fragments capable of dimerizing the receptor, could be used to stimulate cMpl receptor activity. Fabs produced in bacteria were dimerized via the HA tag utilizing the 12CA5 anti-HA antibody. Increasing amounts of 12CA5 was added to the bacterial Fabs to dimerize the Fab clones in order that they might in turn dimerize and activate the cMpl receptor. For measurement of agonist activities Fab containing bacterial supernatants (2 mls) mixed with 12CA5 were applied to NIH3T3 cells which had been co-transfected with either a control vector or the cMpl receptor and the Fos promoter/luciferase reporter construct. Co-transfections of 3T3 cells were performed by plating NIH 3T3 cells at $3 \times 10^5$ cells per 6 cm dish and then transfecting the following day. NIH 3T3 cells were transfected using the Effectine lipofection reagent (Qiagen), transfecting each plate with 0.1 ug pEGFP (a tracer to measure transfection efficiency), 0.2 ug of the Fos promoter/luciferase construct and 0.7 ug of either the empty control vector or the plasmid expressing the cMpl receptor. 3T3 cells were placed in 0.5% serum 24 hours post transfection and incubated for an additional 24 hours in this low serum media to reduce the background activation of the Fos promoter. Antibody supernatants were then applied to these cells for 6 hours. Cells were harvested and luciferase assays performed using 50 ug of cell lysate. No activation was stimulated by the antibodies in the absence of cMpl receptor expression. However, agonist activity was observed in cMpl receptor co-transfected 3T3 cells. This allowed us to demonstrate that the agonist activity observed was through the cMpl receptor and its interaction with the antibody. The data is as follows:

| Bacterial Supernatants with 12CA5 | | |
|---|---|---|
| | Relative Fold Luciferase activity | |
| CELL Treatment | CMpI-R transfected | Control transfected |
| Untreated: | 1.0 | 1.0 |
| + 10% FOS | 3.43 | 3.0 |
| + TPA | 2.3 | 2.42 |
| + TPO | 2.32 | 0.76 |
| + X4c Sup (alone) | 1.03 | 0.94 |
| + X4c + 60 ul α-HA | 1.97 | 0.84 |
| + X4c + 30 ul α-HA | 1.52 | 0.87 |
| + X4c + 10 ul α-HA | 1.22 | 0.86 |
| + X4c + 3 ul α-HA | 0.94 | 0.68 |
| + X4c + 1 ul α-HA | 0.91 | 1.05 |
| + X4c + 0.3 ul α-HA | 1.01 | 0.95 |

Activation of cMpl receptor can be tested in a similar manner using full IgGs (converted from Fab as described herein) produced by transient or stable transfection of mammalian cells rather than bacterially produced Fabs dimerized by anti-HA 12CA5. Experimentally transient transfection can be performed essentially as described here. For transfections $2 \times 10^6$ cells (such as 293 EBNA) would be plated in 6 cm dishes for each test sample. The following day each plate would be transfected with 2.5 ug of total DNA (2 ug total of the light chain and heavy chain plasmid(s), 0.25 ug of pAd-VAntage (Promega, Madison, Wis.), and 0.25 ug of pEGFP) using the Effectine reagent (Qiagen). The 293 cells would be placed in 0.5% serum 24 hours post transfection and incubated for an additional 24 hours in this low serum media to obtain full IgG. Residual growth factors are negligible in this media in stimulating receptors as seen in controls experiments. After 24 hours supernatants would be collected and spun for 5 minutes at 300 rpm to remove any residual cells. For measurement of agonist activities of the full IgGs, 3 mls of the conditioned 293 cell supernatants would be applied to NIH3T3 cells as described above.

Example 2

Additional Libraries Containing TPO Mimetic Sequences Grafted into a Human Antibody Framework Another approach to linking two agonistic peptides together in an antibody framework is to insert the agonist peptide in more than one position within a single Fab fragment. In order to do that, additional libraries containing TPO mimetic sequences grafted into a human antibody framework were constructed. Following selection of peptides properly presented in the context of CDR1, CDR2 or CDR3 of the light chain, or CDR2 of the heavy chain, the binding sequences were combined into a single Fab molecule, for example as listed in Table 1 below, and analyzed for enhanced activity.

TABLE 1

| Peptide 1 | Peptide 2 |
|---|---|
| H-CDR3 | H-CDR2 |
| H-CDR3 | L-CDR1 |
| H-CDR3 | L-CDR2 |
| H-CDR3 | L-CDR3 |

TABLE 1-continued

| Peptide 1 | Peptide 2 |
|---|---|
| H-CDR2 | L-CDR2 |
| H-GDR2 | L-CDR3 |
| L-CDR3 | L-CDR2 |

Four additional libraries have been constructed separately replacing the heavy chain CDR2 as well as the light chain CDR1, CDR2 and CDR3 with the TPO mimetic peptide flanked by 2 random amino acids using an NNK doping strategy. The generation of the libraries was similar to that described for the heavy chain CDR3 TPO peptide library, except that only the chain (heavy or light) being modified to form a library was amplified by PCR and used as the insert. PCR was performed using Expand High Fidelity PCR System (Roche) which contains a mixture of Taq and Pwo Polymerases. The first round of PCR was performed using the program: 94° 30", then 30 cycles of 94° 15", 56° 30", and 72° 2', followed by elongation for 10' at 72° and a 4° hold. Overlap PCR was performed for 10 cycles without primers using the program listed above to allow the full DNA template to be generated by the polymerases. Primers were then added to the PCR reaction tubes for 20 cycles of the same program for amplification.

For the HCDR2 library, the fragment A was created using the forward primer lead VH (5' GCT GCC CAA CCA GCC ATG GCC 3')(SEQ. ID. NO: 13), which annealed at the pel B leader signal located in front of the heavy chain, and the reverse primer HR2 CMPL ANTI (5' AGC CAG CCA CTG GCG CAG GGT TGG GCC TTC GAT MNN MNN TCC CAT CCA CTC AAG CCC TTG 3')(SEQ. ID. NO: 51) that annealed at the end of the heavy chain FR2. The reverse primer contained a tail encoding the new CDR2. Fragment B was created using forward primer HR2 cMpl CODE (5' CCA ACC CTG CGC CAG TGG CTG GCT GCT CGC GCT NNK NNK AGA GTC ACC ATT ACC GCG GAC 3')(SEQ. ID. NO: 14) which annealed at FR3 of the heavy chain and reverse primer N-dp (5' AGC GTA GTC CGG AAC GTC GTA CGG 3')(SEQ. ID. NO: 15) which annealed in the HA epitope tag region of the plasmid, downstream of the heavy chain constant region. The HR2 cMpl CODE primer also had a tail of bases that encoded the new CDR2 region. After the fragments were generated by PCR and gel purified, they were combined for an overlap extension PCR. The new CDR2 primer encoded regions were complementary and provided 24 bases of overlap. Primers leadVH and N-dp were used in the overlap PCR protocol to generate the full heavy chain DNA product. Following gel purification of the heavy chain product, a Xho I/Spe I digest was performed at 37° for 3 hours. Inserts were gel purified and then ligated into Xho I/Spe I digested pRL4 vector containing the anti-TT light chain. Ligation products were precipitated and electroporated into ER2537 bacteria as described above for the generation of the Fab-phage library.

The light chain CDR3 library was similarly made using primers for Fragment A of forward primer N-omp and reverse primer LR3 cMpl ANTI (5' AGC CAG CCA CTG GCG CAG GGT TGG GCC TTC GAT MNN MNN ACA GTA GTA CAC TGC AAA ATC 3') (SEQ. ID. NO: 16) and for Fragment B of forward primer LR3 cMpl CODE (5' CCA ACC CTG CGC CAG TGG CTG GCT GCT CGC GCT NNK NNK TTC GGC CAA GGG ACC AAG GTG 3')(SEQ. ID. NO: 17) and reverse primer leadB (5' GGC CAT GGC TGG TTG GGC AGC 3') (SEQ. ID. NO: 18). Primer leadB annealed to the pelB leader sequence located before the VH. The LR3 cMpl ANTI reverse and LR3 cMpl CODE forward primers annealed to the FR3 and FR4 of anti-TT light chain respectively. Both LR3 cMpl primers contain a tail of nucleotides encoding the new CDR3 peptide library, which provides the 24 basepair overlap region for the fusion PCR of Fragment A and Fragment B. Following purification of the light chain PCR products, a Sac I/Xba I digest was performed at 37° for 3 hours. The light chain fragments were then ligated into Sac I/Xba I digested pRL4 containing the anti-TT heavy chain overnight at room temperature. Ligation products were precipitated and electroporated into ER2537 bacteria as described above for the generation of the Fab-phage library.

The construction of the light chain CDR2 library was carried out as described above for the light chain CDR3 library with the exception that specific primers LR2 cMpl ANTI (5' AGC CAG CCA CTG GCG CAG GGT TGG GCC TTC GAT MNN MNN ATA GAT GAG GAG.CCT GGG AGC 3')(SEQ. ID. NO: 19) which annealed at the end of light chain FR2 and primer LR2 cMpl CODE (5' CCA ACC CTG CGC CAG TGG CTG GCT GCT CGC GCT NNK NNK GGC ATC CCA GAC AGG TTC AGT 3')(SEQ. ID. NO: 20) which annealed at the beginning of light chain FR3 were used in place of the LR3 cMpl primers.

The construction of the light chain CDR1 library was also carried out as previously described for the light chain CDR3 library with the exception that specific primers TPOLR1CODE (5' CCAACCCTGCGCCAGTGGCTG-GCTGCTCGCGCTNNKNNKTGGTACCAGCAGA AAC-CTGGC 3') (SEQ. ID. NO: 58) which annealed at the beginning of the light chain FR2 and the primer TPOLR1ANTI (5' AGCCAGCCACTGGCGCAGGGTTGGGCCT-TCGATMNNMNNGCAGGAGAGGGT GGCTCTTTC 3') (SEQ. ID. NO: 59) which annealed to the end of the light chain FR1 were used in place of the LR3 cMpl primers.

The three additional libraries, which separately replace the heavy chain CDR2 and the light chain CDR2 and CDR3 with the TPO mimetic peptide flanked by 2 random amino acids using the NNK doping strategy, were separately panned on platelets, as was previously described in Example I for the heavy chain CDR3 replacement library. Four rounds of panning were performed and clones were screened by FACS on platelets and cMpl receptor transfected 293 cells as previously described. Two positive clones were obtained from these screens. These clones had the TPO mimetic peptide in the heavy chain CDR2. Unlike with the heavy chain CDR3 clones neither of the heavy chain CDR2 clones had a proline in downstream position. Instead both were found to contain a tyrosine in the upstream position (See FIG. 9-clones HC-CDR2 No. 24 and No. 39).

The libraries, including LCDR1, were separately subjected to another panning experiment using cMpl receptor transfected 293 cells instead of platelets during the panning. The 293 cells were observed to reproducibly transfect at a high efficiency and express very high levels of the functional cMpl-receptor on their surface. Thus these cells represented a good cell target for use in panning. For these experiments different groups of plates of 293 cells were separately and sequentially transfected four days in a row. Each group of plates was then sequentially used for the four separate rounds of panning. Each round of harvesting of the cells and panning occurred two days after transfection. For harvesting, cells were removed from the plates using cell disassociation buffer, spun down at 1500 rpm for 5 minutes and re-suspended in IMDM supplemented with 10% FCS, 0.1% sodium azide and 5 mM EDTA at a concentration of $1 \times 10^6$ cell per ml ($3 \times 10^6$ for LC-CDR1). In the round one pan, $3 \times 10^{11}$ phage from each library were separately applied to 2 ml of cells (6×10⁶ for LC-CDR1 and 2×10⁶ cells for all others) and rotated in a 15 ml conical tube for two hours at room temperature. Cells were washed twice using 10 mls of the IMDM/10% FCS/0.1% sodium azide/5 mM EDTA buffer. Phage were eluted in acid and amplified as previously described in Example 1. In round two 4×10⁶ cells (6×10⁶ for LC-CDR1) were used in 2 ml of buffer and 3×10¹¹ phage from the amplified round one eluted phage was combined with 3×10¹¹ phage from the un-panned library and added to the cells. Washing, elution and amplification proceeded similar to round one. In round three 4×10⁶ cells (6×10⁶ for LC-CDR1) were used in 2 ml of buffer and 3×10¹¹ phage from the amplified round two eluted phage were used. Cells were washed three times prior to elution. In round four, 4×10⁶ cells (6×10⁶ for LC-CDR1) were again used in 2 ml of buffer and 3×10¹¹ phage from the amplified round three eluted and amplified phage were used. Cells were again washed three times prior to elution. At least thirty individual clones were screened by FACS on cMpl receptor transfected 293 cells as previously described. 12 positive clones were obtained from the heavy chain CDR2 library and 25 positive clones were obtained from the light chain CDR2 library, and 14 positive clones were obtained from the light chain CDR1 library. Clones were further analyzed by DNA sequence. The selected flanking amino acid residues for the positive clones are depicted in the attached FIG. 9. It is of interest to note that the light chain CDR2 grafted Fabs have a strong selection for a proline (Pro) upstream of the TPO mimetic peptide.

Example 3

Combinations of the TPO mimetic peptide grafted Fab clones from FIG. 9 have been generated. Thus a single antibody might contain multiple copies of the TPO mimetic peptide within a single light or heavy chain. Alternatively, both the light and heavy chains might contain peptide grafts giving multiple copies within a single Fab. Positive clones selected from the same CDR library were pooled. New libraries were constructed by combining the pool of one TPO mimetic peptide containing CDR with the pool of another. Combinations where one of the TPO mimetic peptides is in the light chain and the other is in the heavy chain are made using simple cloning techniques using the pooled plasmid DNAs, and the unique restriction sites flanking the heavy (Xho I-SpeI) and light chains (Sac I-Xba I). For example, the plasmid DNA for the H-CDR3 peptide grafted heavy chains were combined and digested by Xho I and Spe I. The purified heavy chain inserts were ligated into the Xho I/Spe I digested plasmid containing the L-CDR2 grafts. The resulting library contained heavy chains with CDR3 peptide grafts and light chains with CDR2 peptide grafts. It should be understood that individual clones could also be combined rather that using pools of clones for the pairing of two peptide containing CDRs. For example, a single heavy chain clone with a CDR3 peptide graft was paired with several individual light chain CDR1 clones to create Fabs with multiple copies of TPO mimetic peptides.

Combinations where two TPO mimetic peptides were combined within a given heavy chain was performed using overlap PCR to generate the fragment for cloning. Two overlapping primers which bind between CDR2 and CDR3, and flanking primers, such as "N omp" and "lead B" primers from the light chain and "Lead VH" and "Ndp" primers for the heavy chain were used. For example, to combine H-CDR2 and H-CDR3 CDR3 the first PCR was performed using lead VH (a primer that anneals in the vector at the heavy chain pelB leader signal) and a reverse primer annealing at FR3 using the H-CDR2 pooled plasmid DNA as the template. The sequence of that primer was 5' CCA TGT AGG CTG TGC CCG TGG ATT 3' (SEQ. ID. NO: 63). In a separate reaction, the pooled plasmids containing the H-CDR3 grafts underwent PCR with a forward primer annealing in FR3 (which is complementary to the above FR3-reverse primer) and N-dp (which anneals in the vector at an epitope tag sequence). The sequence of that primer was 5' CCA CGG GCA CAG CCT ACA TGG AGC 3' (SEQ. ID. NO: 64). The first PCR products were purified then combined in an overlap PCR reaction, where fusion of the two fragments occurred through the complementary FR2 sequences. The full heavy chain product was cloned by Xho I/Spe I into a plasmid containing the anti-tetanus toxoid light chain. In all, five classes of Fabs bearing multiple copies of TPO mimetic peptides were created as detailed in Table 2 below.

TABLE 2

| Peptide 1 | Peptide 2 | Peptide 3 |
|---|---|---|
| H-CDR3 | H-CDR2 | |
| H-CDR3 | L-CDR2 | |
| H-CDR2 | L-CDR2 | |
| H-CDR3 | H-CDR2 | L-CDR2 |
| H-CDR3 | L-CDR1 | |

20 clones from each combination library and four individual clones of H-CDR3 plus L-CDR1 were tested for biological activity in a luciferase reporter assay as previously described. See FIGS. 10 and 11. In both experiments, the negative controls can include uninduced cells, cells treated with an irrelevant Fab (anti-tetanus toxoid), cells treated with a Fab clone that only weakly binds cMpl receptor, and X4b and/or X1c Fabs which do bind the cMpl receptor but only have a single binding domain and so can not activate the receptor. The positive control was the addition of TPO. All remaining samples were from the newly formed combination libraries. As can be observed, several clones have significant activity as Fabs. This indicates that incorporation of multiple TPO mimetic peptides into a single Fab molecule is able to bind two receptors and cause receptor activation.

In fact, using Fab 59 the agonistic activity obtained can be as high as native TPO activity. Clone 59 containing two TPO mimetic peptides (HC CDR3 sample x4c and LC CDR2 sample 19 as identified in FIG. 9) and a His6 tag was partially purified from a bacterial periplasmic prep by FPLC using nickel column chromatography. The activity of this Fab was measured and found to be approximately equivalent to that of TPO (see FIG. 12), as estimated by cMpl-R specific induction of luciferase activity in direct comparison to known concentrations of TPO. A quantitative western blot was performed in order to determine the Fab 59 antibody concentrations.

These Fabs, or various other two CDR combinations, could be used as a therapeutic product. Alternatively, these clones could be converted to framework germline sequences (either with or without codon optimization) for use as a therapeutic agent so long as activity was maintained.

Example 4

The TPO mimetic peptide graft in Fab clone X4b has been transplanted into the heavy chain CDR3 of another antibody framework, 5G1.1. Construction of 5G1.1 is described in U.S. application. Ser. No. 08/487,283, incorporated herein by reference. The sequence was cloned into 5G1.1 in such a fashion as to replace the native CDR3 with 5' ttg cca ATT GAA GGG CCG ACG CTG CGG CAA TGG CTG GCG GCG CGC GCG cct gtt 3' (SEQ. ID. NO: 65). The peptide graft translated into amino acids is Leu Pro Ile Glu Gly Pro Thr Leu Arg Gln Trp Leu Ala Ala Arg Ala Pro Val (SEQ. ID. NO: 66). The 5G1+peptide was produced as a whole IgG antibody (See FIGS. 13A and 13B).

Figure 14:
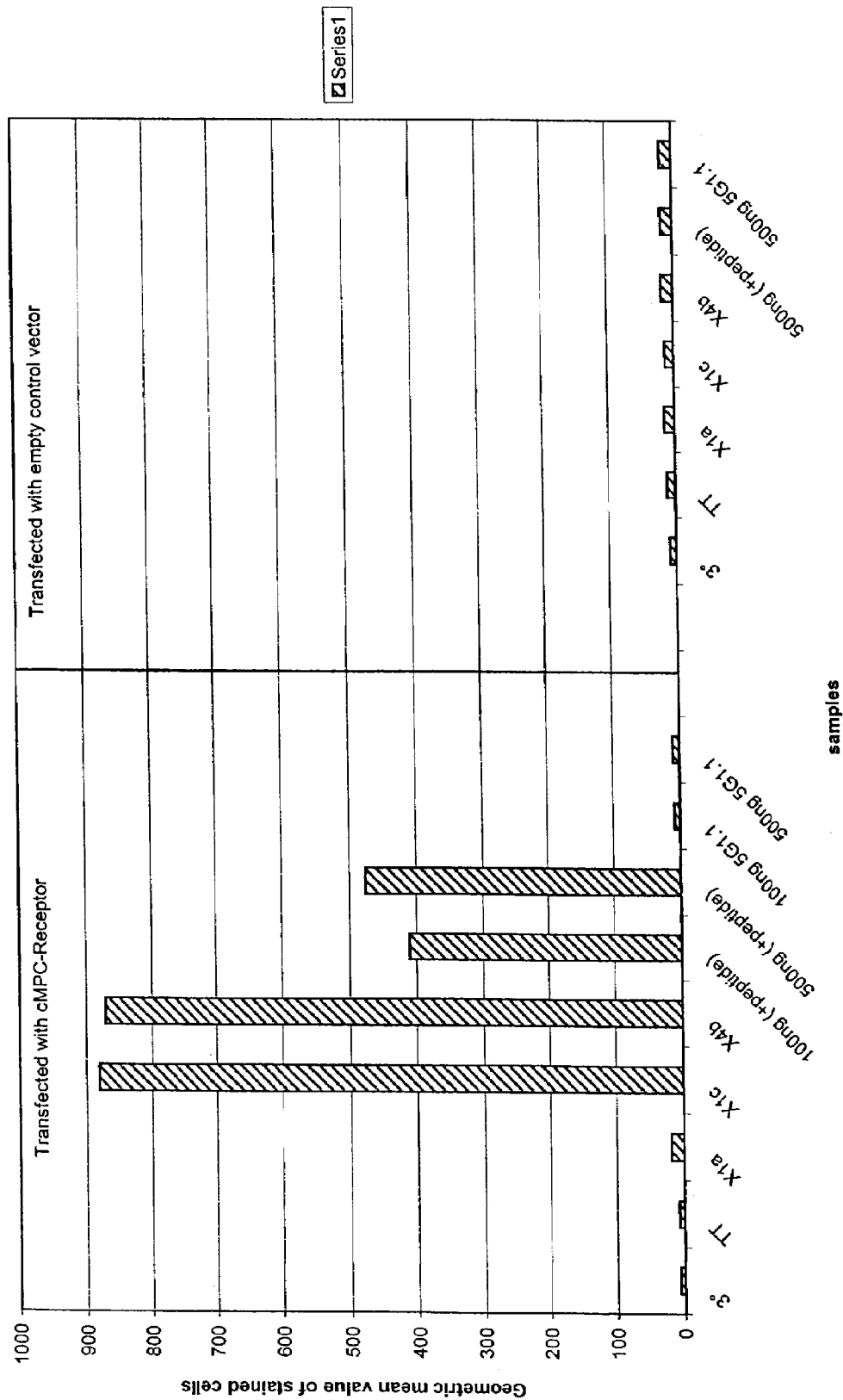

Purified 5G1.1+peptide antibody as well as the parental 5G1.1 were analyzed for their ability to bind to cMpl receptor by FACS analysis. Binding to receptor expressing and non-receptor expressing 293 cells was compared. See FIG. 14. The FACS staining was performed essentially as described previously herein, with the exception that the detection was done using PE conjugated F(ab')2 fragment of goat anti-human IgG (H+L). The negative controls of 3° only anti-tetanus toxoid irrelevant Fab, and Fab X1a which binds weakly to cMpl receptor all showed very little staining. However, binding Fabs X1c and X4b showed strong staining as did the 5G1.1+peptide. None of those clones demonstrated binding to the non-receptor expressing cells indicating that the cell staining is occurring through specific recognition of the cMpl receptor. The parental 5G1.1 without the TPO mimetic peptide did not show staining to any of the cells tested.

Figure 15:
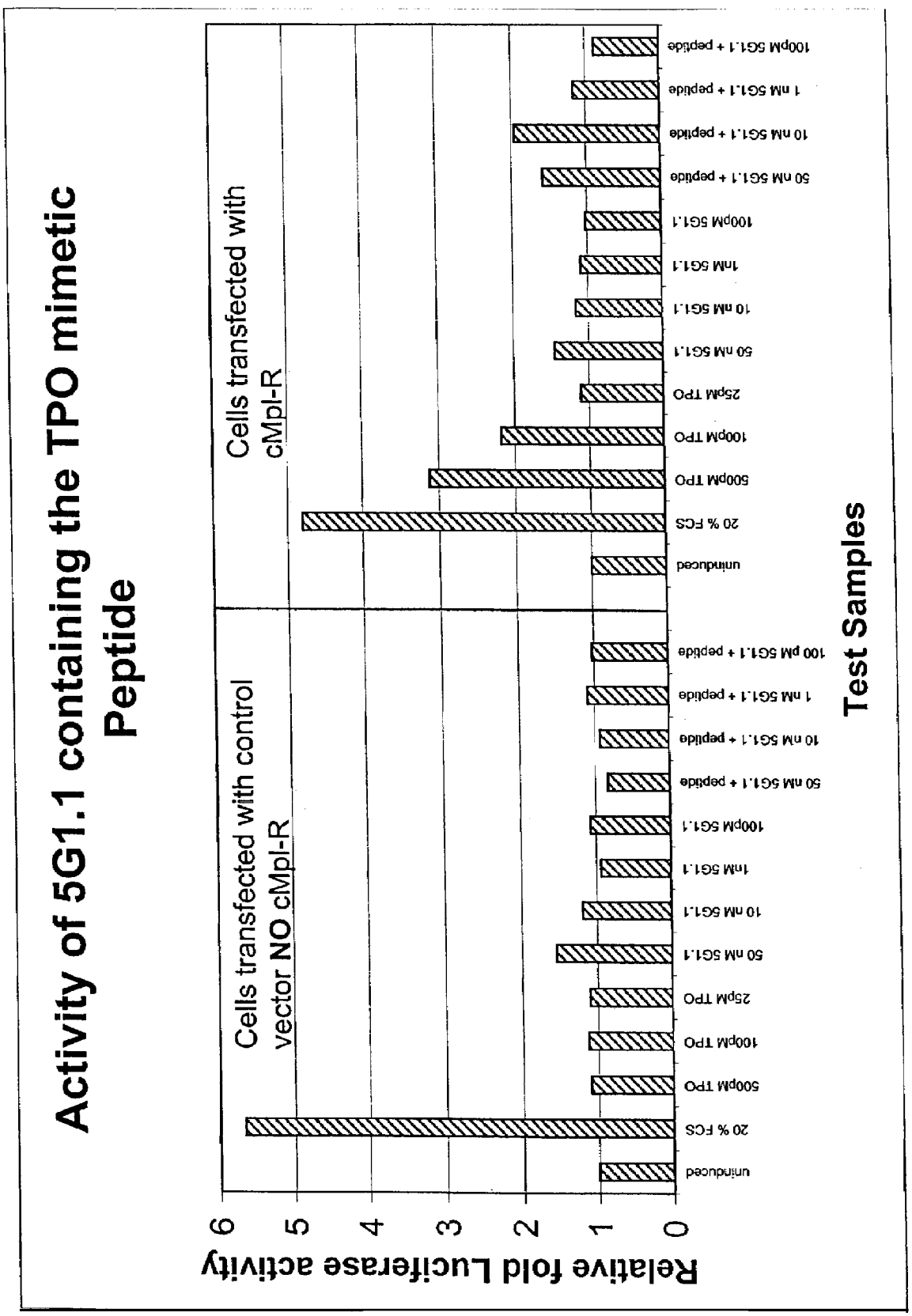

The ability of the 5G1.1+ peptide whole IgG to activate the cMpl receptor using the luciferase reporter assay has been determined (see FIG. 15). The results herein indicate that the configuration of a whole IgG causes steric limitations in its ability to productively bring the two cMpl receptors together for activation. The activity of the 5G1.1 full IgG construct containing the TPO mimetic peptide in the heavy chain CDR3 positions, was only weakly activating and required approximately 100-200 fold higher molar concentrations as compared to TPO, to stimulate equivalent activity. As was previously observed with the binding experiments, activation by the 5G1.1 containing the peptide was observed only when the cMpl-R was expressed on the cell surface. No receptor specific binding or activity was observed with the parental 5G1.1 not containing the peptide. These results demonstrate that binding and activity of the TPO mimetic peptide and selected amino acid flanking sequences is not limited to or specific for the Tetanus Toxoid antibody framework, but can be applied to other antibody frameworks. Thus the flanking amino acid sequences that were selected during panning are specific for presentation of the TPO mimetic peptide within a given CDR position, but not for amino acid sequence of the antibody framework.

Example 5

Library Construction of Epo Mimetic Sequences Grafted into a Human Antibody Framework An agonist EPO mimetic-peptide DYHCRMG-PLTWVCKPLGG (SEQ. ID. NO: 3) (designated EMP2 in Wrighton et al. 1996) was grafted separately into the anti-tetanus toxoid Fab heavy and light chain CDR3 region creating two antibody libraries as XXDYHXRMGPLTWVXK-PLGGXX (SEQ. ID. NO: 71). Randomized positions were generated using an NNK doping strategy. As with the TPO mimetic peptide, two amino acids flanking the EPO mimetic peptide were randomized in order to select for the optimum presentation of the peptide. In addition the cysteine residues, which formed a disulfide bridge in the original cyclic peptide, were randomized. This was done not only because the CDRs already form loop structures and so the disulfide bridge was not necessary to constrain the peptide, but also because the cysteines might in fact disrupt the normal disulfide bonds of the antibody.

The CDR 3 of the anti-TT antibody heavy chain was completely replaced by the EPO peptide library graft. The generation of the library was essentially as described for the TPO heavy chain CDR2 library. Two alternate primers were used for the HCDR3 library: the reverse primer HR3 EPO ANTI (5' CAC CCA GGT CAG TGG GCC CAT GCG MNN ATG ATA GTC MNN MNN TCT CGC ACA ATA ATA TAT GGC 3')(SEQ. ID. NO: 21) that annealed at the end of the heavy chain FR3, and forward HR3 EPO CODE (5'CGC ATG GGC CCA CTG ACC TGG GTG NNK AAA (SEQ. ID. NO:22) CCA CTG NNK NNK TGG GGC CAA GGG ACC ACG GTC 3')

which annealed at FR4 of the heavy chain.

The light chain CDR3 EPO peptide library was constructed essentially as described above for the light chain CDR3 TPO peptide library using reverse primer LR3 EPO ANTI (5' CAC CCA GGT CAG TGG GCC CAT GCG MNN ATG ATA GTC MNN MNN ACA GTA GTA CAC TGC AAA ATC 3') (SEQ. ID. NO: 23) that annealed at the end of light chain FR3 and forward primer LR3 EPO CODE (5' CGC ATG GGC CCA CTG ACC TGG GTG NNK AAA CCA CTG NNK NNK TTC GGC CAA GGG ACC AAG GTG 3') (SEQ. ID. NO: 24) which annealed to FR4 of the light chain.

Selection of the Epo Mimetic Peptide Heavy Chain Cdr3 Library and Light Chain Cdr3 Library Selection for peptide presentation was performed by solid phase panning on the soluble EPO receptor. In this method, 1 ug of purified human EPO-soluble R (hEPO-sR from R&D Systems, Minneapolis, Minn. cat #307-ER-050) was immobilized on a microtiter dish overnight at 4°. After washing off free hEPO-sR, the plates were blocked with 1% BSA/PBS for one hour at 37°. Phage, prepared as described above, were added to the wells and incubated two hours at 37°. Washes were performed using PBS/0.5% Tween 20 for 5' at room temperature per wash. 1, 5, 10, and 10 washes were performed in the first, second, third and fourth panning rounds respectively. After the washing steps were completed, the bound Fab-phage were eluted with 30 uls of elution buffer for 10' at room temperature. Eluted phage were then neutralized and amplified as described in Example 1.

Example 6

A library was generated by the insertion of a TPO mimetic peptide and previously selected flanking amino acids (NP-IEGPTLRQWLAARA-RG) (SEQ. ID. NO: 61) into a collection of human kappa gene fragments, in this case the CDR2 of the light chain. Stocks of human kappa light chains from multiple human peripheral blood lymphocyte (PBL) donors had been previously generated and cloned into pBluescript II SK+. Those constructs served as the source of antibody gene fragments.

Antibody Gene Banks

Total RNA from human PBLs was isolated using TRI Reagent (Molecular Research Center, Cincinnati, Ohio) followed by mRNA purification with Oligotex mRNA purification System (QIAGEN, Valencia, Calif.) according to kit instructions. First strand cDNA was made using SuperScript RTase II cDNA Synthesis Kit (Life Technologies, Rockville, Md.) with a modified oligo dT primer. The sequence of the primer was 5' TAGGATGCGGCCGCACAGGTC($T_{20}$) 3'

(SEQ. ID. NO: 62). Samples were cleaned up over a PCR purification Kit spin column (QIAGEN, Valencia, Calif.) according to kit directions. Light chain products were amplified using the reverse "Not I" primer and forward primers which annealed at the framework 1 (FR1) position of Kappa chains on the 1st strand cDNA. The "Not I" primer had sequence which was identical to the 5' end of the modified oligo dT primer (5' TAGGATGCGGCCGCACAGGTC 3') (SEQ. ID. NO: 72). The set of Kappa FR1 primers used were:

```
XVB Vk1a  CACGCGCACAACACGTCTAGARACATCCAGATGACCCAG      (SEQ. ID. NO:73)

XVB Vk1b  CACGCGCACAACACGTCTAGAGMCATCCAGTTGACCCAG      (SEQ. ID. NO:74)

XVB Vk1c  CACGCGCACAACACGTCTAGAGCCATCCRGATGACCCAG      (SEQ. ID. NO:75)

XVB Vk1d  CACGCGCACAACACGTCTAGAGTCATCTGGATGACCCAG      (SEQ. ID. NO:76)

XVB Vk2a  CACGCGCACAACACGTCTAGAGATATTGTGATGACCCAG      (SEQ. ID. NO:77)

XVB Vk2b  CACGCGCACAACACGTCTAGAGATRTTGTGATGACTCAG      (SEQ. ID. NO:78)

XVB Vk3a  CACGCGCACAACACGTCTAGAGAAATTGTGTTGACRCAG      (SEQ. ID. NO:79)

XVB Vk3b  CACGCGCACAACACGTCTAGAGAAATAGTGATGACGCAG      (SEQ. ID. NO:80)

XVB Vk3c  CACGCGCACAACACGTCTAGAGAAATTGTAATGACACAG      (SEQ. ID. NO:81)

XVB Vk4a  CACGCGCACAACACGTCTAGAGACATCGTGATGACCCAG      (SEQ. ID. NO:82)

XVB Vk5a  CACGCGCACAACACGTCTAGAGAAACGACACTCACGCAG      (SEQ. ID. NO:83)

XVB Vk6a  CACGCGCACAACACGTCTAGAGAAATTGTGCTGACTCAG      (SEQ. ID. NO:84)

XVB Vk6b  CACGCGCACAACACGTCTAGAGATGTTGTGATGACACAG      (SEQ. ID. NO:85)
```

A typical amplification reaction contained 2 μls cDNA reaction, dNTPs, "Not I" reverse primer, one of the XVB forward primers, Opti-prime buffer #5 (Stratagene, La Jolla, Calif.), and Expand High Fidelity polymerase mixture (Roche Molecular Biochemicals, Indianapolis, Ind.). Samples were heated to 94° C. for 2 minutes, then carried through 10 cycles of 94° C. for 15 seconds, 56° C. for 30 seconds, and 72° C. for 1 minute, followed by 20 cycles of 94° C. for 15 seconds, 56° C. for 30 seconds, and 72° C. for (1 minute+5 seconds/cycle). The cycles were followed by an extended incubation at 72° C. (7 minutes) prior to 4° C. hold. Products were ethanol precipitated and then gel purified. Fragments of approximately 850 bp were isolated and then digested with Xba I and Sac I. The resulting kappa products were ligated into pBluescript II SK+ that had likewise been digested with Xba I and Sac I. The ligation products were electroporated into Top10F' (Invitrogen, Carlsbad, Calif.) and grown overnight. The bacterial pellet was used to isolate the Kappa library DNA with QIAGEN's MAXIprep DNA isolation kit.

Construction of Framework Library with TPO Mimetic Peptide

For construction of the TPO light chain framework library, equal amounts of four different kappa light chain libraries from four different patients were used as the starting template for the PCR reactions (25 ng total per reaction). The TPO mimetic peptide and selected flanking amino acids were incorporated into the light chains by overlap PCR. In the first round of PCR a set of reverse primers (VK ANTI primers) which bound to the kappa light chain FR2 were separately combined with the forward T7 seq-F primer (5'-ATTAATAC-GACTCACTATAGGG-3') (SEQ. ID. NO: 86) to synthesize the N terminal piece of the light chain and part of the TPO mimetic peptide within the LC CDR2 position. A second set of forward primers (VK CODE primers), which bound to FR3, were combined separately with the T3 reverse primer (5'-AATTAACCCTCACTAAAGGG-3') (SEQ. ID. NO: 87) to synthesize the rest of the TPO mimetic peptide within the LC CDR2 position and the C terminal half of the light chain by PCR. Separate reactions were performed for each pair of primer combinations in duplicate.

```
VK6ANTI
5'AGCCAGCCACTGGCGCAGGGTTGGGCCTTCGATCGGGTTCCTGATGAGGAGC     (SEQ. ID. NO:88)
TTTGGRG-3'

VK5ANTI
5'AGCCAGCCACTGGCGCAGGGTTGGGCCTTCGATCGGGTTTTGAATAATGAAAA    (SEQ. ID. NO:89)
TAGCAG-3'

VK4ANTI
5'AGCCAGCCACTGGCGCAGGGTTGGGCCTTCGATCGGGTTGTAAATGAGCARCT    (SEQ. ID. NO:90)
TAGGAG-3'

VK3ANTI
5'AGCCAGCCACTGGCGCAGGGTTGGGCCTTCGATCGGGTTATAGATGAGGAGC     (SEQ. ID. NO:91)
CTGGGMG-3'

VK2AANTI
5'AGCCAGCCACTGGCGCAGGGTTGGGCCTTCGATCGGGTTATAAATTAGGCGCC    (SEQ. ID. NO:92)
TTGGAG-3'

VK2BANTI
5'AGCCAGCCACTGGCGCAGGGTTGGGCCTTCGATCGGGTTATAGATYAGGAGCT    (SEQ. ID. NO:93)
GTGGAG-3'

VK1AANTI
5'AGCCAGCCACTGGCGCAGGGTTGGGCCTTCGATCGGGTTATAGATCAGGAGCT    (SEQ. ID. NO:94)
```

-continued

```
TAGGA-3'

VK1BANTI
5'AGCCAGCCACTGGCGCAGGGTTGGGCCTTCGATCGGGTTRTAGATCAGGAGCT   (SEQ. ID. NO:95)
TAGGG-3'

VK1CANTI
5'AGCCAGCCACTGGCGCAGGGTTGGGCCTTCGATCGGGTTATAGATCAGGGACT   (SEQ. ID. NO:96)
TAGGG-3'

VK1DANTI
5'AGCCAGCCACTGGCGCAGGGTTGGGCCTTCGATCGGGTTATAGATCAGGYGCT   (SEQ. ID. NO:97)
TAGGG-3'

VK6CODE
5'CCAACCCTGCGCCAGTGGCTGGCTGCTCGCGCTCGTGGTGGGGTCCCCTCGA    (SEQ. ID. NO:98)
GGTTCAG-3'

VK5CODE
5'CCAACCCTGCGCCAGTGGCTGGCTGCTCGCGCTCGTGGTGGAATCCCACCTC    (SEQ. ID. NO:99)
GATTCAG-3'

VK4CODE
5'CCAACCCTGCGCCAGTGGCTGGCTGCTCGCGCTCGTGGTGGGGTCCCTGACC    (SEQ. ID. NO:100)
GATTCAG-3'

VK3ACODE
5'CCAACCCTGCGCCAGTGGCTGGCTGCTCGCGCTCGTGGTGGCATCCCAGMCA    (SEQ. ID. NO:101)
GGTTCAG-3'

VK3BCODE
5'CCAACCCTGCGCCAGTGGCTGGCTGCTCGCGCTCGTGGTGGTATCCCAGCCA    (SEQ. ID. NO:102)
GGTTCAG-3'

VK2ACODE
5'CCAACCCTGCGCCAGTGGCTGGCTGCTCGCGCTCGTGGTGGAGTSCCAGAYA    (SEQ. ID. NO:103)
GGTTCAG-3'

VK2BCODE
5'CCAACCCTGCGCCAGTGGCTGGCTGCTCGCGCTCGTGGTGGGGTCCCWGACA    (SEQ. ID. NO:104)
GRTTCAG-3'

VK1ACODE
5'CCAACCCTGCGCCAGTGGCTGGCTGCTCGCGCTCGTGGTGGGGTCCCATCAA    (SEQ. ID. NO:105)
GGTTCAG-3'

VK1BCODE
5'CCAACCCTGCGCCAGTGGCTGGCTGCTCGCGCTCGTGGTGGGGTCCCATCTC    (SEQ. ID. NO:106)
GGTTCAG-3'
```

Fragments from the first rounds of PCR were gel purified. Those purified fragments were then combined, in an antibody family specific manner, in overlap PCR reactions to generate the full light chain. Reactions for each family were performed in triplicate using 40 ng of both the N-terminal and C-terminal piece of the light chain in each reaction. The reactions were run for 10 cycles prior to the addition of the T3 and T7 Seq-F primers, followed by an additional 25 cycles after primer addition. The full length LC fusion PCR products were gel purified, digested with Sac I and Xba I, and then again gel purified. The light chain inserts were then ligated into an appropriate phage display vector, which had been similarly digested with Xba I and Sac I and gel purified. The pRL5-kappa vector used had restriction sites which were compatible with the LC fragments and contained the remaining Kappa constant region from the native Sac I site to the C-terminal Cys. In addition, the anti-tetanus toxoid heavy chain was inserted into the vector by Xho I and Spe I for Fab production.

The ligation mixture was transformed by electroporation into XL-1 Blue bacteria (Stratagene, La Jolla Calif.) and amplified. The library was panned four rounds on 293 EBNA cells transfected with the cMpl-R in a manner similar to that previously described. Clones obtained during panning were screened for binding by FACs analysis on 293 EBNA cells transfected with or without the cMpl-R as previously described. A number of clones, which specifically bound the cMpl-R, were obtained. DNA fingerprinting of the resulting light chains by digestion with Bst N1 indicated that the clones could be divided into 5 different groups. Partial sequencing of 8 of these clones showed that frameworks from at least two different kappa light chain families were selected during the panning (VK1 and VK3). In an initial test, 3 of the light chain framework clones were combined with the heavy chain of X4b to create a Fab with 2 TPO mimetic peptides. These clones induced activation of the cMpl-R in luciferase assays as previously described. The level of activation using bacterial supernatants of one such clone 429/X4b (see FIG. 16) was approximately 10-20 fold lower than that observed with TPO, as estimated by comparing activity to known concentrations of TPO and using quantitative western blots to determine the concentration of the antibody in the supernatant. Additional clones can be screened in a similar fashion on order to identify clones with greater activity.

These Fabs, or various other LC, HC or intrachain CDR combinations, could be used as a therapeutic product. Alternatively, these clones could be converted to framework germline sequences (either with or without codon optimization) for use as a therapeutic agent so long as activity was maintained.

Modification of the Phage Display Vectors pAX131 and pRL5

Figure 17:
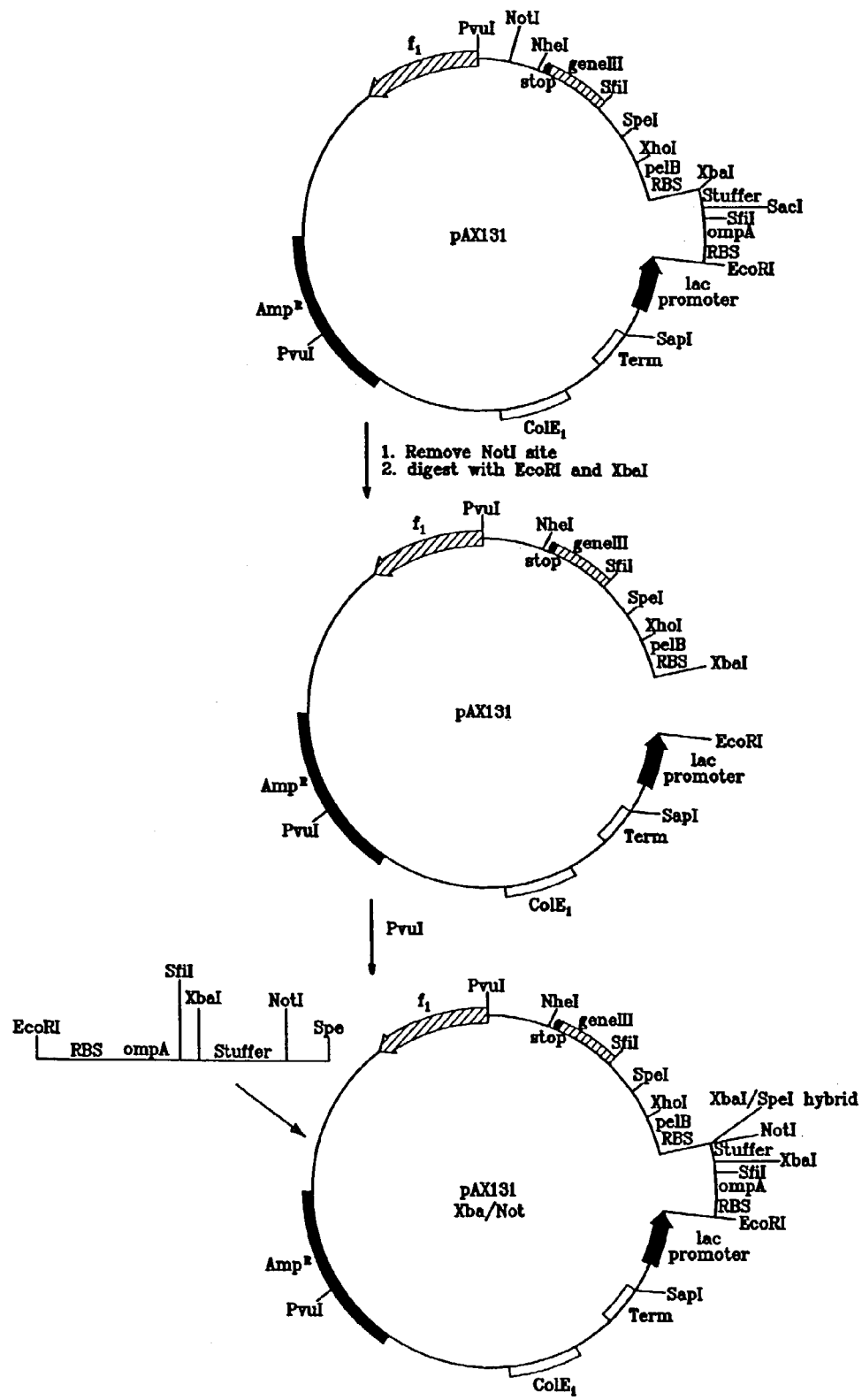

The Not I site in pAX131 was removed by digesting the vector with Not I, using Klenow polymerase to fill in the Not I overhangs, and then re-ligating the vector. See FIG. 17. Further modification was made by digesting pAX 131 with EcoR I and Xba I. An insert that replaced the elements removed by such digestion was generated using overlapping oligonucleotides with the following changes: conversion of the Sac I site to a new Xba I site (single underline in primer sequences below), conversion of the original Xba I site to a Not I site (double underline in the primer sequences below), and ending the insert with a Spe I overhang which is compatible with the vector's Xba I digest generated overhang. Ligation of the EcoR I/Spe I insert into the EcoR I/Xba I cut vector resulted in an Spe I/Xba I hybrid which will no longer cut with either Spe I or Xba I at that site. The sequence of the oligos used were: "EcoSpe" 5' AA TTC

```
                                            (SEQ. ID. NO:107)
"EcoSpe" 5' AA TTC AAG GAG TTA ATT ATG AAA AAA ACC

GCG ATT GCG ATT GCG GTG GCG CTG GCG GGC TTT GCG

ACC GTG GCC CAG GCG GCC TCT AGA ATC TGC GGC CGC a 3', and (SEQ. ID. NO:108)
"SpeEco" 5' ct agt GCG GCC GCA GAT TCT AGA GGC CGC

CTG GGC CAC GGT CGC AAA GCC CGC CAG CGC CAC CGC

AAT CGC AAT CGC GGT TTT TTT CAT AAT TAA CTC CTT

G 3'.
```

Figure 18:
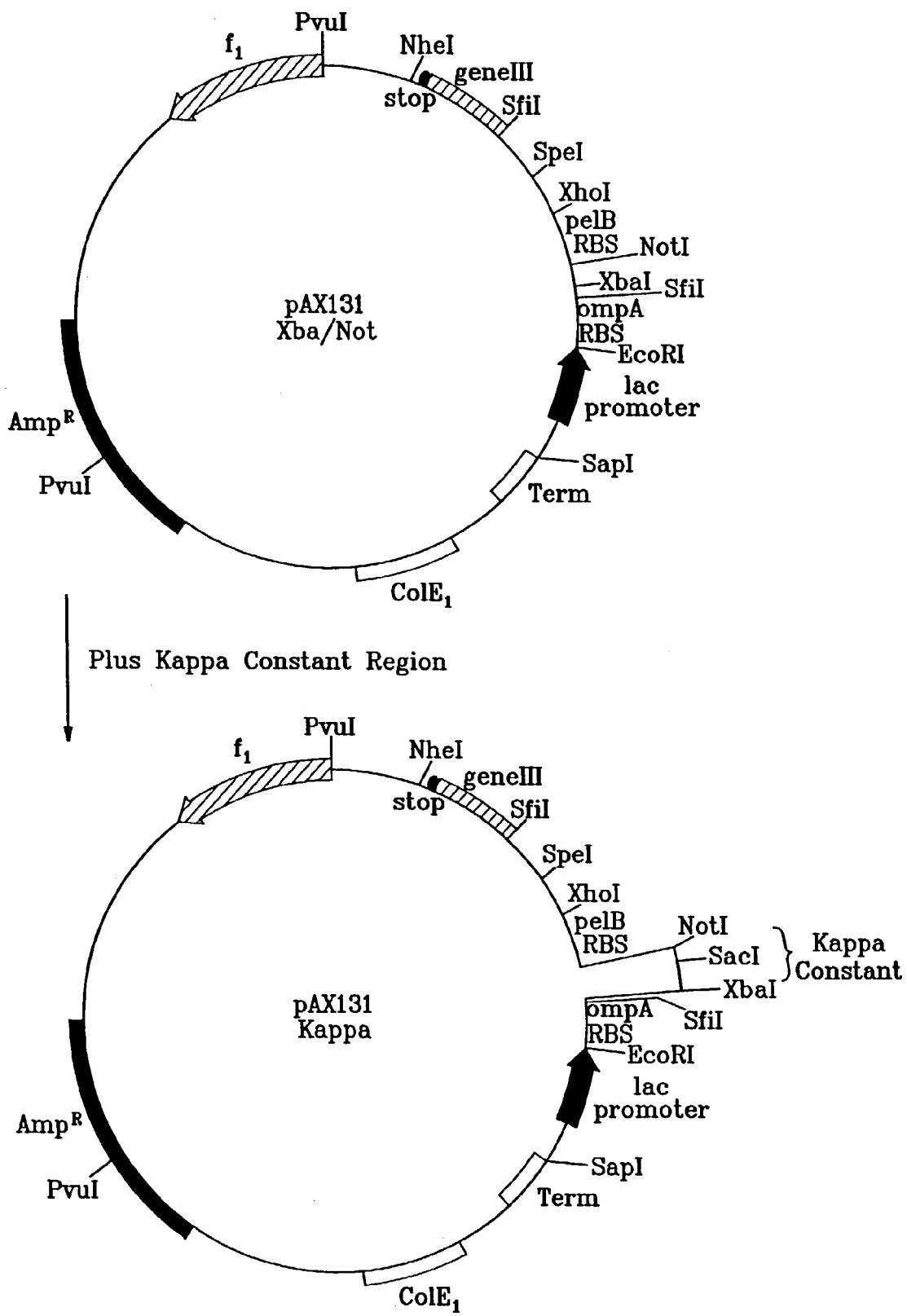

The intermediate vector created was pAX131Xba/Not. The human kappa constant region was inserted between the Xba I and Not I sites generating pAX131-kappa (see FIG. 18). The human kappa constant region was PCR amplified from human cDNA using primers that introduced the upstream Xba I site and in the downstream position a TAA stop codon followed by a Not I site. The primers used

```
CKXba I  (5' GGA GTC TAG ATA ACT GTG GCT GCA CCA TCT GTC TTC 3')   (SEQ. ID. NO:109)
and CKNotI   (5' AGG AGC GGC CGC TTA ACA CTC TCC CCT GTT GAA GCT C     (SEQ. ID. NO:110)
         3').
```

Figure 19:
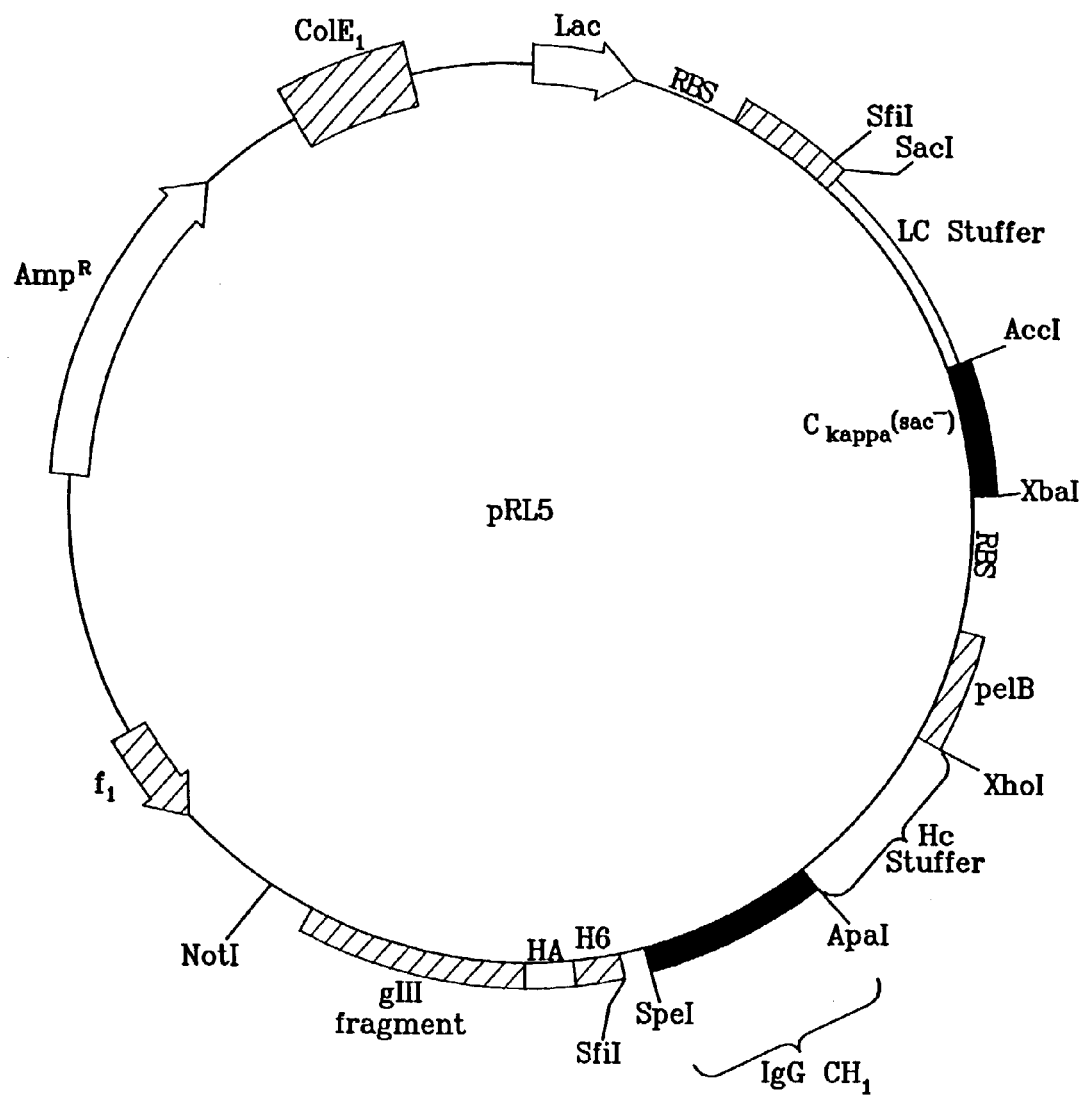
Figure 20:
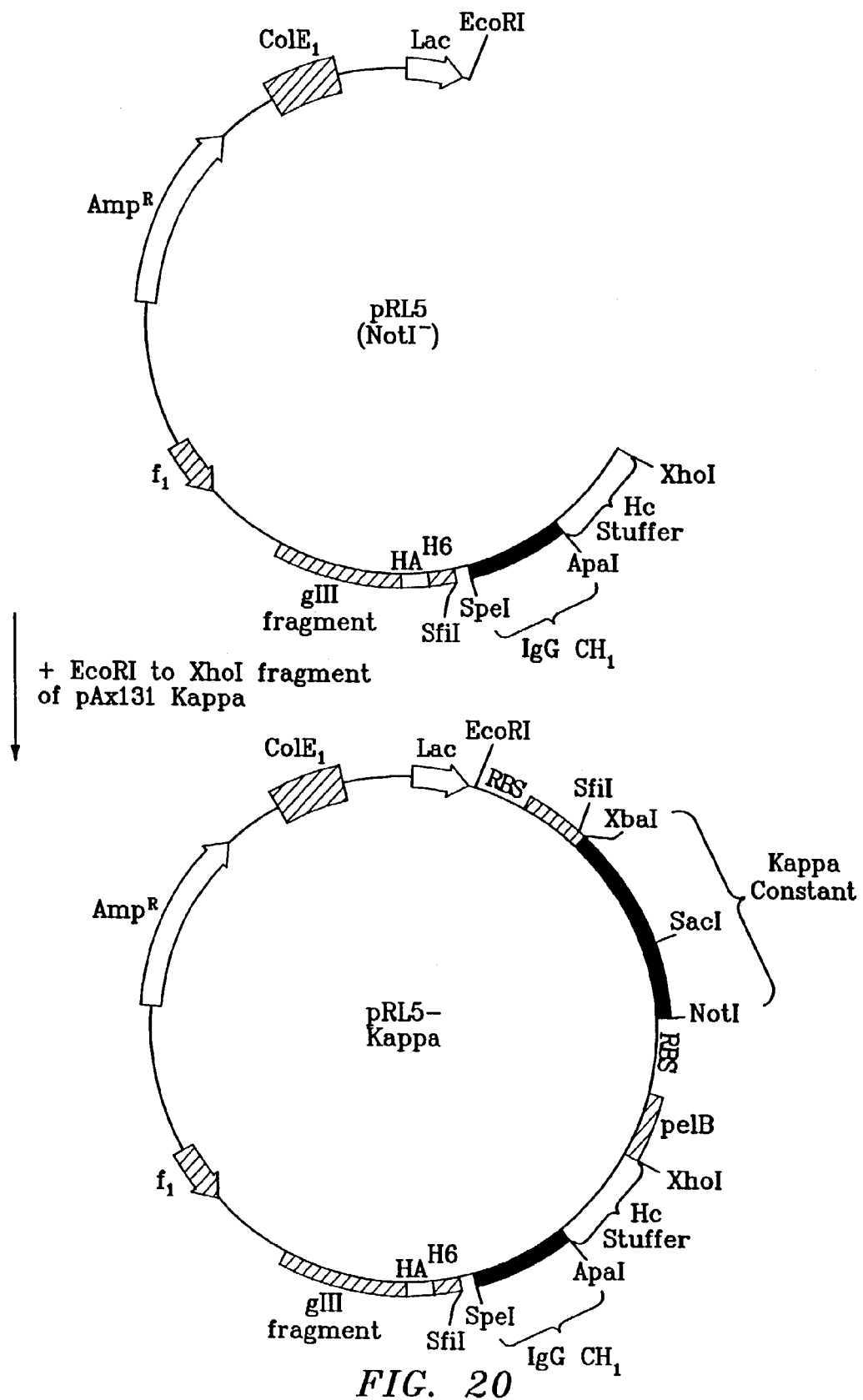
Figure 21A:
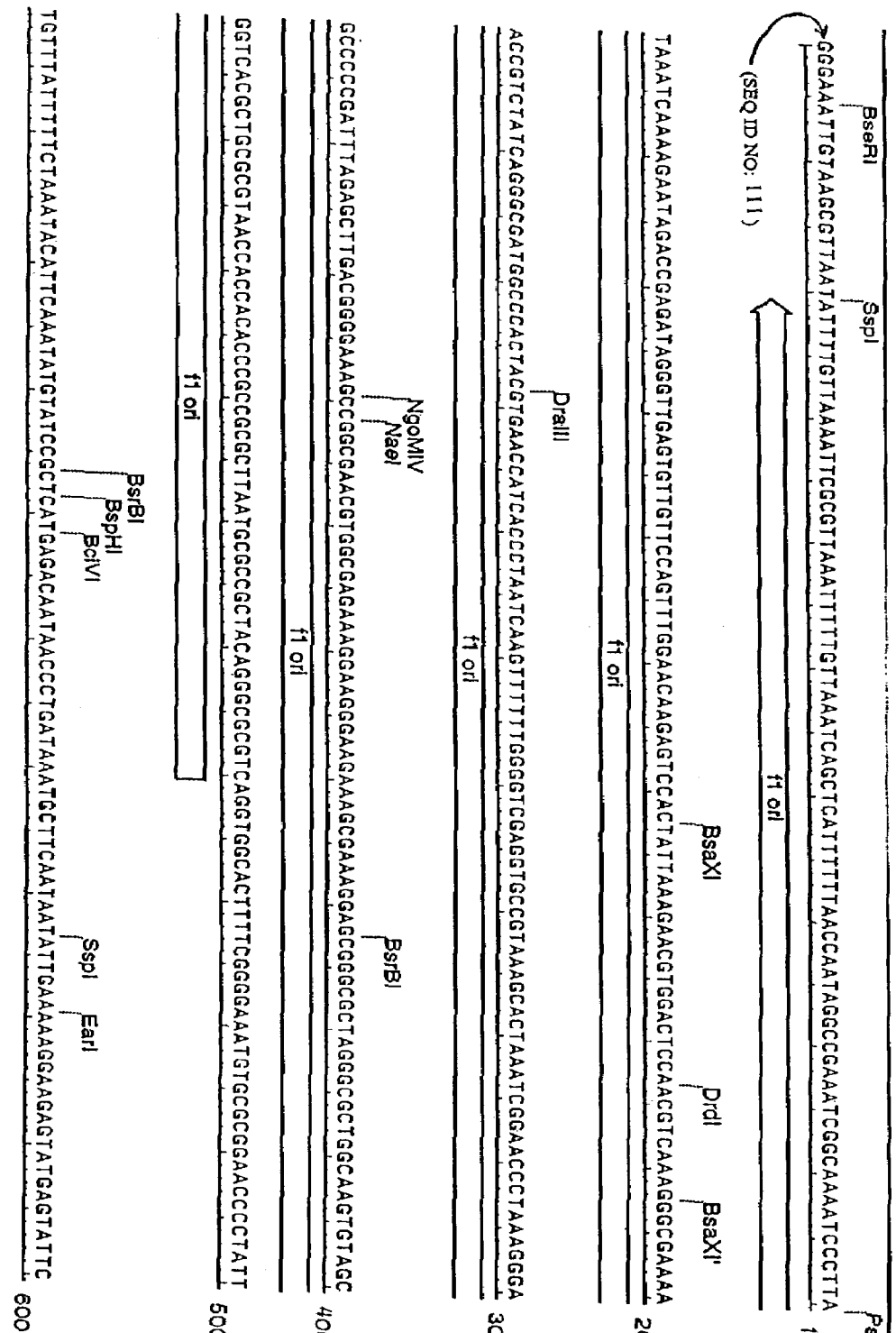
Figure 21B:
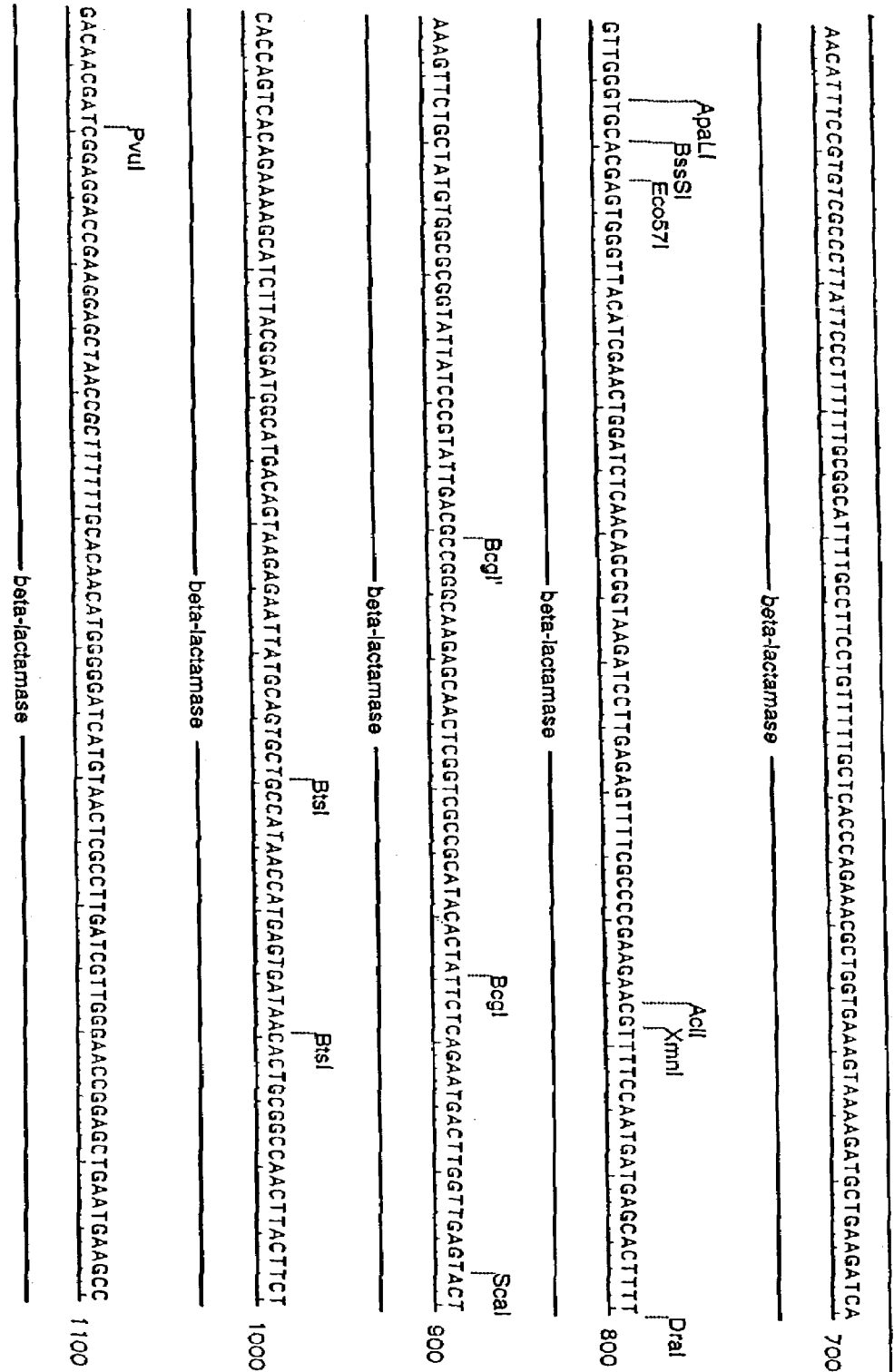
Figure 21C:
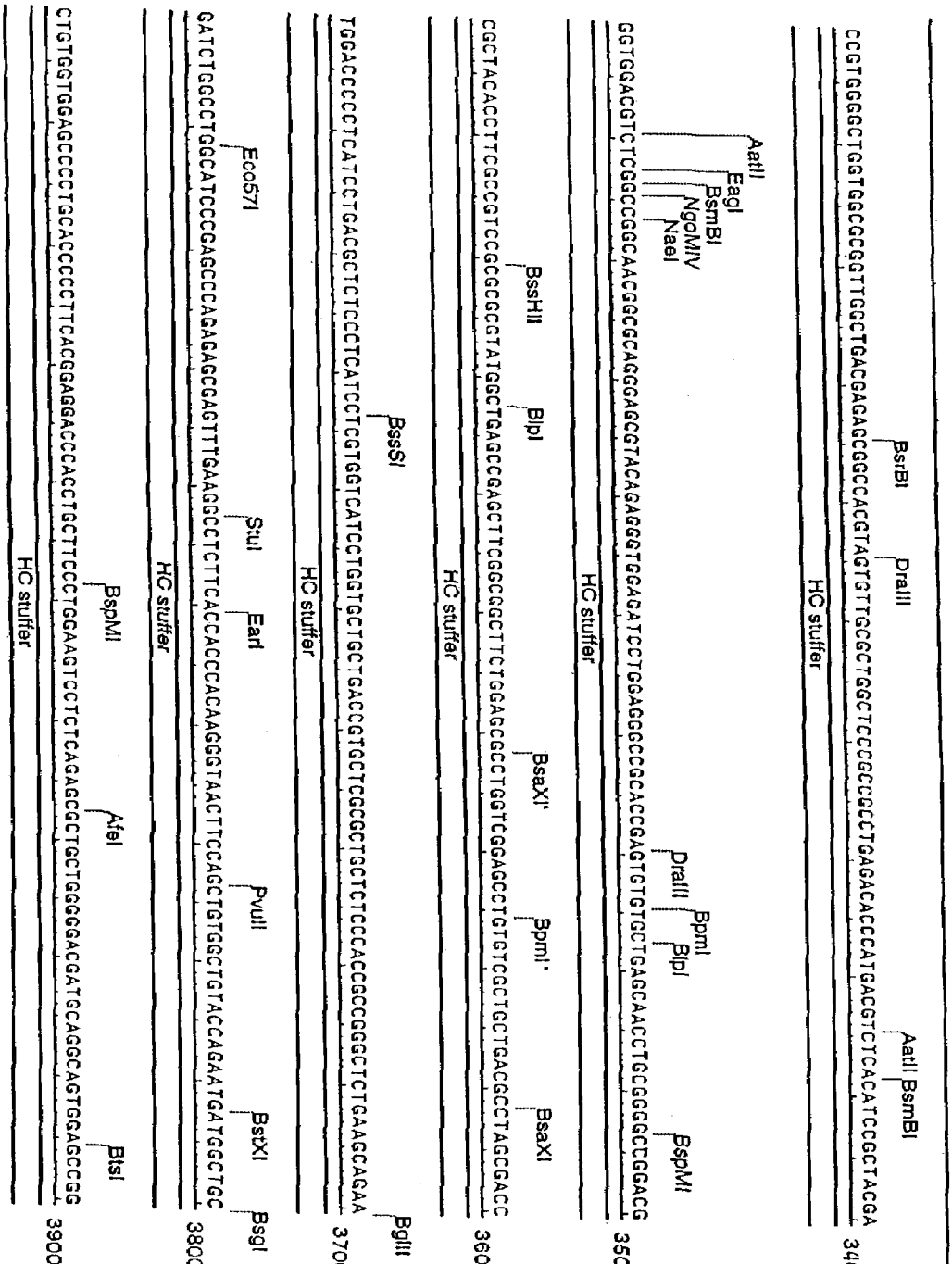
Figure 21F:
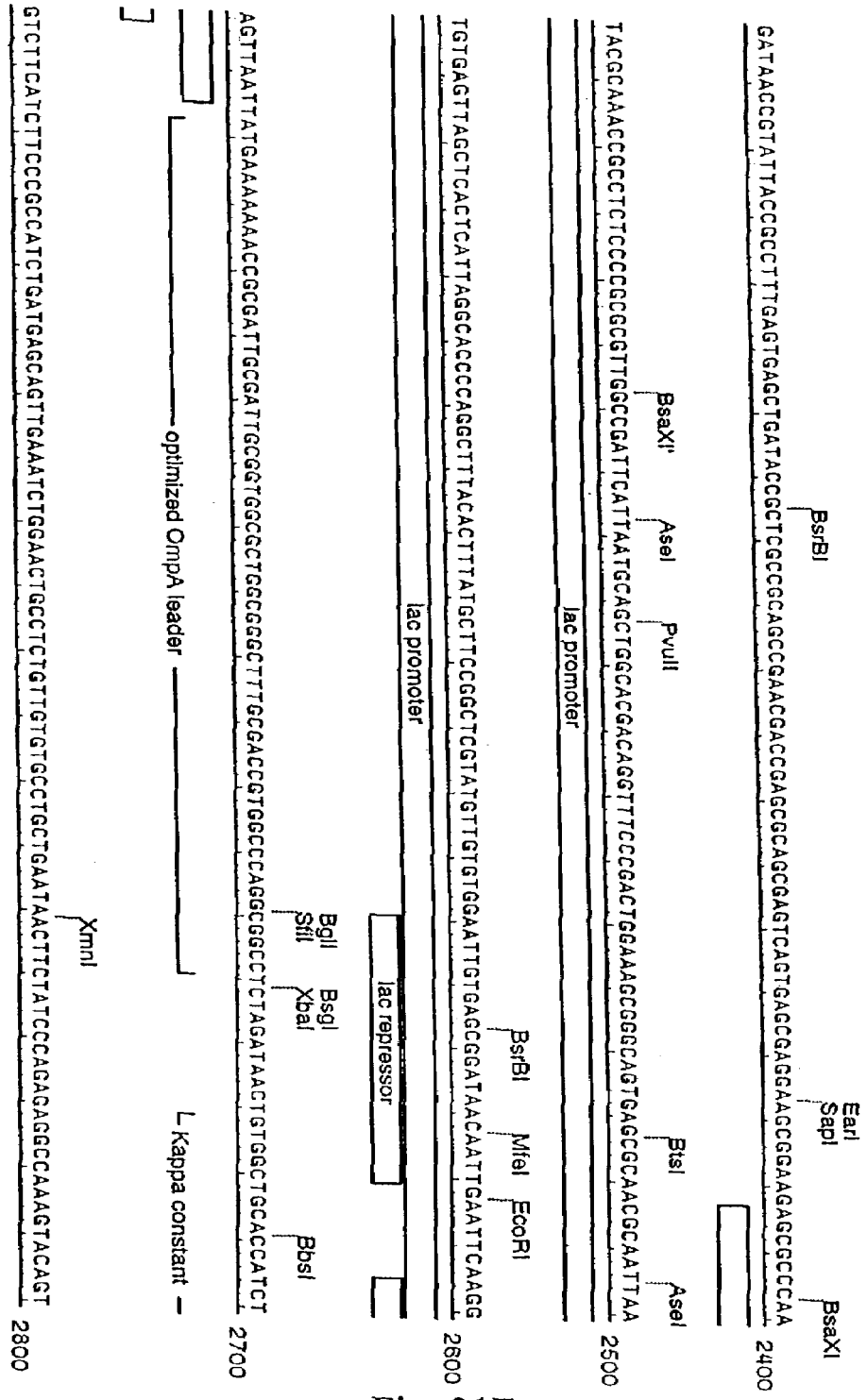
Figure 21G:
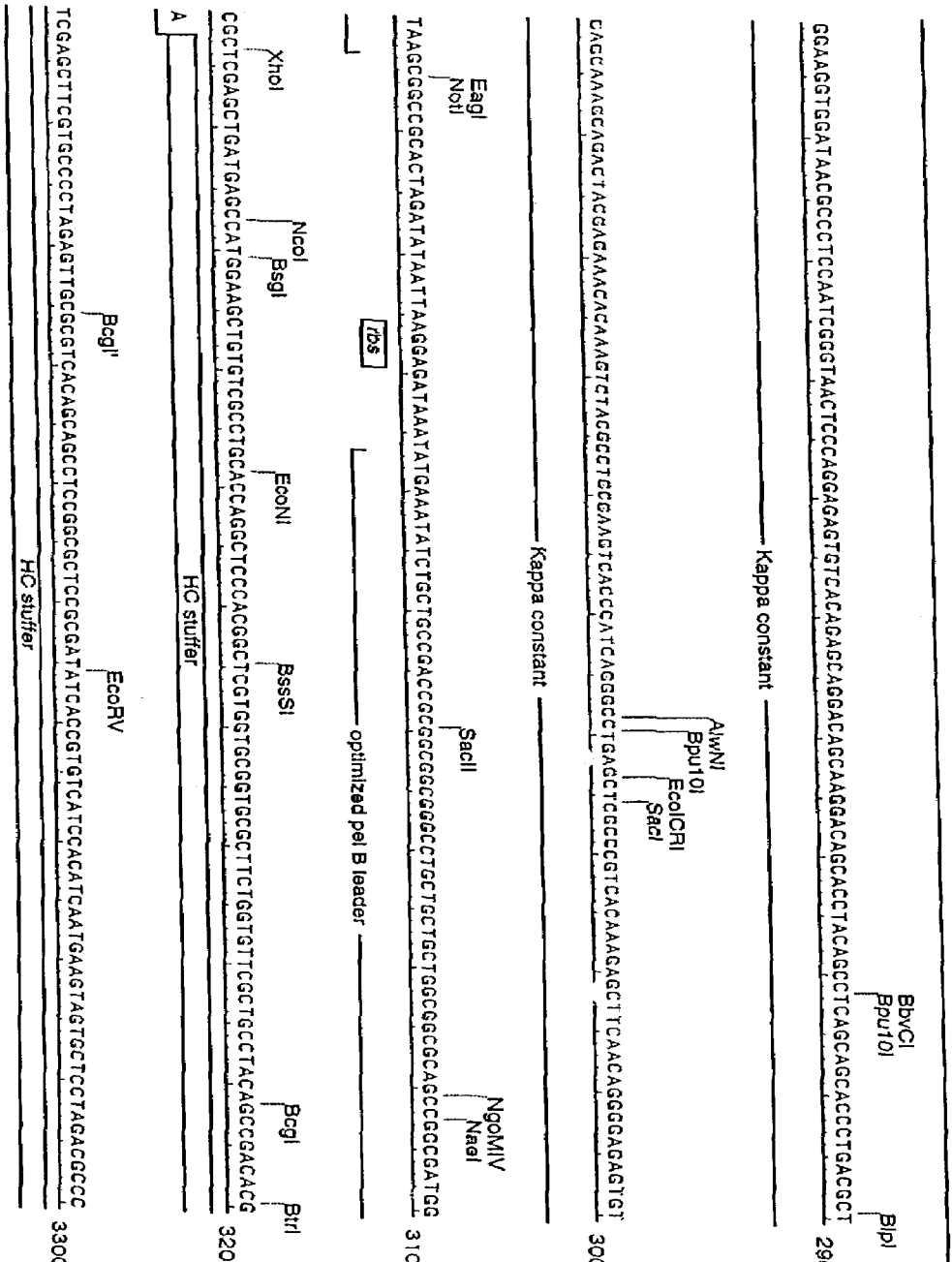
Figure 21H:
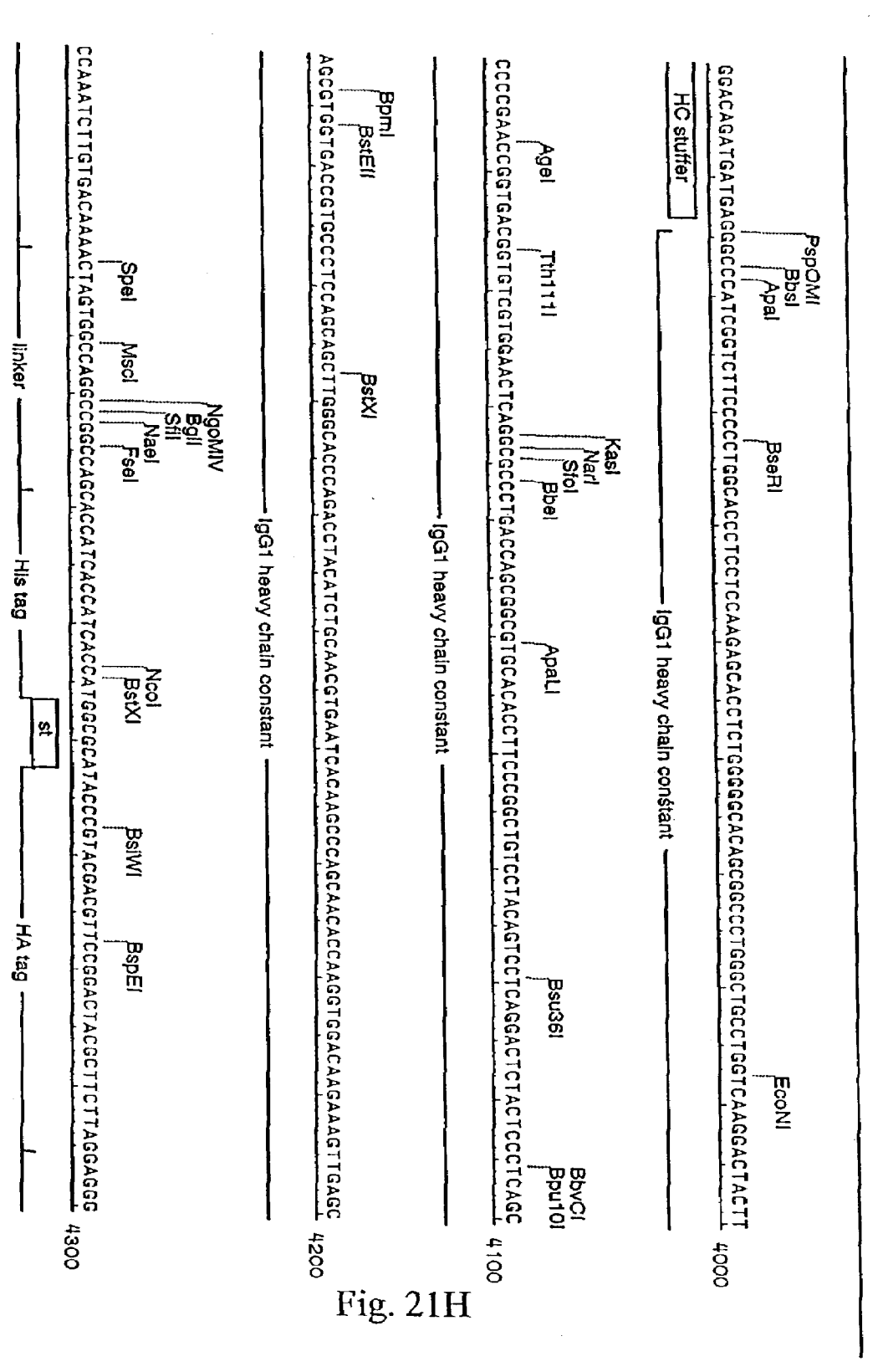
Figure 21I:
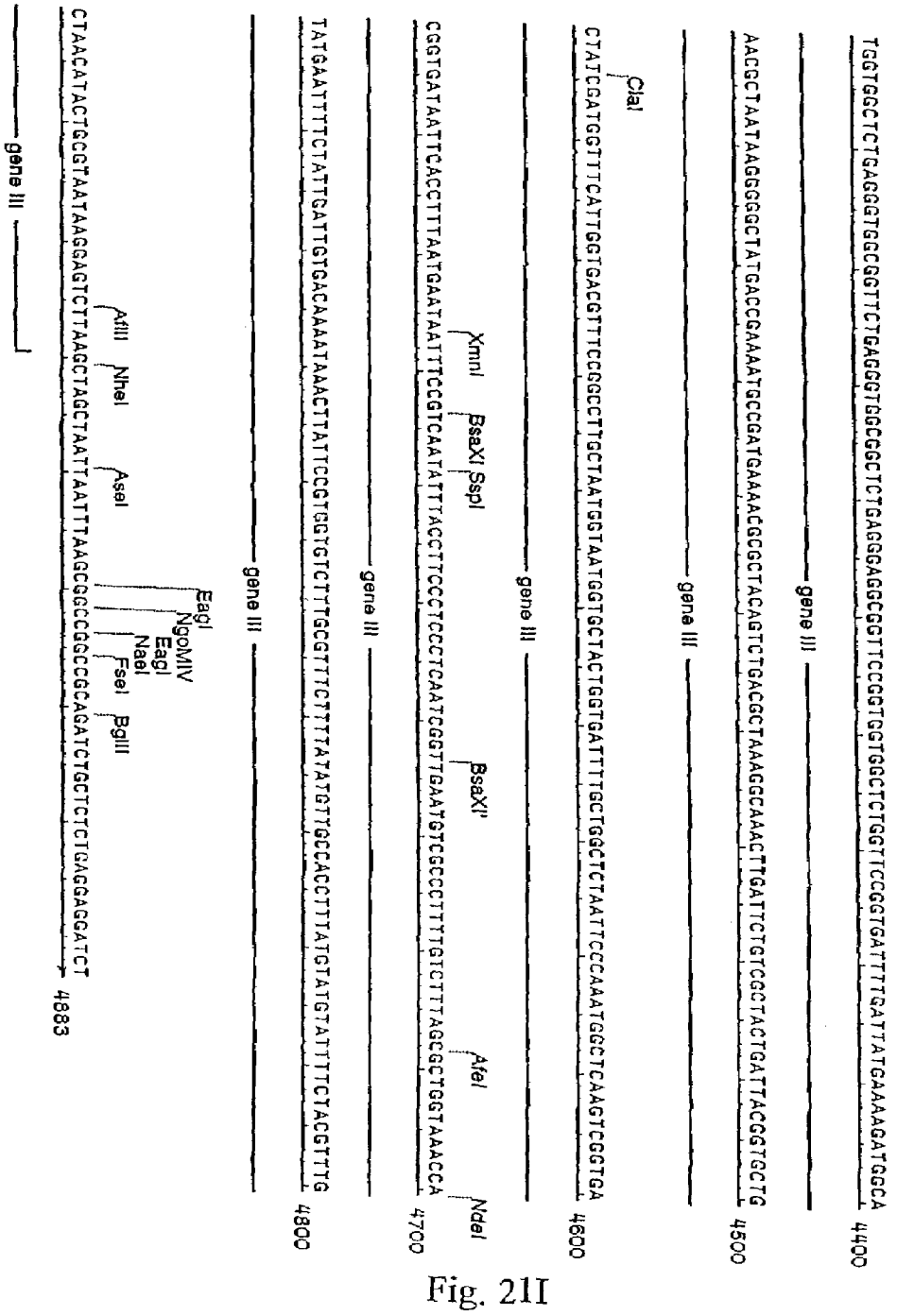

The light chain cloning modifications incorporated into pAX131-kappa were shuttled into the pRL5 vector (modified to have its Not I site removed as described above) by moving the EcoR I to Xho I fragment. See FIGS. 19 and 20. This vector was designated as pRL5-kappa. (See FIGS. 21A-I.)

Example 7

(Core H-CDR2 Library)

An additional HC CDR2 library was constructed where a core sequence of the TPO mimetic peptide (GPTLRQWL) (SEQ. ID. NO: 112) flanked by a single random amino acid on each side was inserted into the heavy chain partially replacing the CDR2 (GXGPTLRQWLXYAQKFQG) (SEQ. ID. NO: 113). The construction of the heavy chain partial CDR2 replacement library was also carried out as previously described for the heavy chain CDR2 library with the exception that the specific primer 8HCR2anti0 (5' CAGCCACTG-GCGCAGGGTTGGGCCMNNCCCTCCCATC-CACTCAAGCCC-3') (SEQ. ID. NO: 114) which annealed at the end of the heavy chain FR2 and the primer 8HCR2code (5'GGCCCAACCCTGCGCCAGTGGCTGNNK-TACGCACAGAAATTCCAG GGCAGAGTCACCATT-3') (SEQ. ID. NO: 115) which annealed to the beginning of the heavy chain FR3 were used in place of the previously described HR2 cMpl primers. The heavy chain partial CDR2 replacement library was panned four rounds on 293 EBNA cells transfected with the cMpl-R as described previously. These clones can now be screened for positive binding clones by FACs analysis as previously described.

Example 8

An individual clone was created by combining the heavy chain CDR3 clone X4b (See FIGS. 5 and 9), with the heavy chain CDR2 clone 19 (see FIG. 9) to create a new Fab clone containing two TPO mimetic peptides. This clone was further modified by codon optimization and conversion to germline sequences. This new clone, which was named 116 (FIG. 22) was purified to 95% homogeneity. The specific activity of the purified 116 Fab was then tested using the luciferase based assays as previously described. The specific activity of the purified 116 was found to be approximately 30 fold lower than TPO (FIG. 23).

Example 9

A third heavy chain CDR2 library was constructed replacing part of the tetanus toxoid (TT) heavy chain CDR2 with the TPO mimetic peptide flanked by two random amino acids on each side.

Computer modeling indicated that it might be beneficial to stability and folding of the heavy chain to retain four amino acids of the original TT HC CDR2. Specifically, the first three amino acids of the TT heavy chain CDR2 (GLY-ILE-PHE) and the last amino acid of the heavy chain CDR2 (GLY). Thus, the final product would contain these original four amino acids with the TPO mimetic peptide and random flanking amino acids positioned between the first three original amino acids and last original amino acid: GIFXXIEGPTLRQWLAARAXXG (SEQ. ID NO. 119).

The construction of the heavy chain partial CDR2 replacement library was also carried out as described for the previous 2 heavy chain CDR2 libraries with the exception that the specific primer HCR2+ANTI (5' AGCCAGCCACTGGCGCAGGGTTGGGCCTTCGATMNNMNNGAAGATCCCTCCC ATCCACTC-3') (SEQ. ID NO. 120) which annealed at the end of the heavy chain FR2 and the primer HCR2+CODE (5' CCAACCCTGCGCCAGTGGCTGGCTGCTCGCGCTNNKNNKGGCAGAGTCACCA TTACCGCG-3') (SEQ. ID NO. 121) which annealed to the beginning of the heavy chain FR3 were used in place of the previously described HR2 cMPL primers. The heavy chain partial CDR2 replacement library was panned four rounds on 293 EBNA cells transfected with the cMPL-R as described previously. A number of clones with strong binding characteristics were obtained and sequenced (FIG. 24).

The clones of the round four pool from panning are used as the starting point for insertion of a second TPO mimetic peptide. For example, this library has been combined with the clone X4b containing a TPO mimetic peptide in the heavy chain CDR3 by sub-cloning, to create clones, which contain two TPO mimetic peptides (one in heavy chain CDR2 and one in heavy chain CDR3). These new clones are screened for TPO mimetic activity. In addition, the second peptide may be placed in light chain CDR1, CDR2 or CDR3, or heavy chain CDR1.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended herein.

What is claimed is:

1. An immunoglobulin molecule or fragment thereof comprising atleast a first thrombopoietin (TPO) peptide mimetic and atleast a second TPO peptide mimetic, wherein the first TPO peptide mimetic replaces a single portion of a first complementarity determining region (CDR), said portion comprising one or more contiguous amino acid residues of the first CDR, and the second TPO peptide mimetic replaces a single portion of a second CDR, said portion comprising one or more contiguous amino acid residues of the second CDR, and wherein the immunoglobulin molecule or a fragment thereof binds to and agonizes a TPO receptor.

2. An immunoglobulin molecule or fragment thereof according to claim 1 further comprising at least one flanking sequence including at least one amino acid covalently linked to at least one end of at least one peptide mimetic.

3. An immunoglobulin molecule or fragment thereof according to claim 2 wherein the at least one flanking sequence includes a flanking sequence having a proline that is covalently linked to the peptide mimetic.

4. An immunoglobulin molecule or fragment thereof according to claim 1 wherein the immunoglobulin molecule fragment is selected from the group consisting of Fab fragment, F(ab')$_2$ fragment and scFv fragment.

5. An immunoglobulin molecule according to claim 1 wherein the immunoglobulin molecule is a full IgG molecule.

6. An immunoglobulin molecule or fragment thereof according to claim 1 wherein the two CDRs are both located on a heavy chain.

7. An immunoglobulin molecule or fragment thereof according to claim 1 wherein the TPO mimetic comprises SEQ. ID. NO. 1.

8. An immunoglobulin molecule or fragment thereof according to claim 1 wherein a heavy chain CDR3 and CDR2 are replaced with a peptide and the heavy chain comprises a variable region of SEQ. ID. NO. 125.

9. An immunoglobulin molecule or fragment thereof according to claim 1 wherein the immunoglobulin molecule or fragment thereof is human.

10. An immunoglobulin molecule or fragment thereof according to claim 1 wherein the immunoglobulin molecule or fragment thereof is anti-tetanus toxoid.

11. A composition comprising an immunoglobulin or fragment thereof according to claim 1 and a pharmaceutically acceptable carrier.

12. An immunoglobulin molecule or fragment thereof comprising a complementarity determining region (CDR) wherein a peptide mimetic comprising SEQ ID NO. 126 replaces a single portion of said CDR, said portion comprising one or more contiguous amino acid residues, wherein Xaa at each occurrence represents any amino acid, and wherein the immunoglobulin molecule or a fragment thereof binds to and agonizes a TPO receptor.

13. An immunoglobulin molecule or fragment thereof according to claim 12 wherein the immunoglobulin molecule or fragment thereof is human.

14. An immunoglobulin molecule or fragment thereof according to claim 12 wherein the immunoglobulin molecule or fragment thereof is anti-tetanus toxoid.

15. A composition comprising an immunoglobulin or fragment thereof according to claim 12 and a pharmaceutically acceptable carrier.

16. An immunoglobulin molecule or fragment thereof according to claim 1 wherein the CDRs are both located on a light chain.

17. An immunoglobulin molecule or fragment thereof according to claim 1 wherein one CDR is located on a heavy chain and one CDR is located on a light chain.

18. An immunoglobulin molecule or fragment thereof according to claim 1 wherein the CDRs are selected from the group consisting of CDR2 and CDR3.

19. An immunoglobulin molecule or fragment thereof according to claim 18 wherein at least one of the CDRs is located in a heavy chain.

20. An immunoglobulin molecule or fragment thereof according to claim 18 wherein at least one of the CDRs is located in a light chain.

21. An immunoglobulin molecule or fragment thereof according to claim 18 wherein one CDR is a CDR2 and one CDR is a CDR3.

22. An immunoglobulin molecule or fragment thereof according to claim 18 wherein the CDRs are selected from the group consisting of heavy chain CDR3-light chain CDR3, heavy chain CDR3-heavy chain CDR2, light chain CDR3-light chain CDR2, heavy chain CDR3-light chain CDR2, heavy chain CDR3-heavy chain CDR2-light chain CDR2, and heavy chain CDR2-light chain CDR2.

23. An immunoglobulin molecule or fragment thereof according to claim 17 wherein the CDRs are heavy chain CDR3 and light chain CDR1.

24. An immunoglobulin molecule or fragment thereof according to claim 1 wherein a heavy chain CDR3 is replaced with a peptide mimetic having SEQ ID NO. 39 and a light chain CDR2 is replaced with a peptide mimetic having SEQ ID NO. 61.

25. An immunoglobulin molecule or fragment thereof according to claim 24 wherein at least one mimetic is flanked with a proline at its carboxy terminus.

26. An immunoglobulin molecule or fragment thereof according to claim 3 wherein at least one peptide mimetic is flanked with a proline at the carboxy terminus.

27. An immunoglobulin molecule or fragment thereof according to claim 2 wherein the flanking sequence consists of two amino acids.

28. An immunoglobulin molecule or fragment thereof according to claim 3 wherein the flanking sequence consists of two amino acids.

29. An immunoglobulin molecule or fragment thereof according to claim 1 wherein the two peptide mimetics are identical.

30. An immunoglobulin molecule or fragment thereof comprising at least a first agonist peptide mimetic and at least a second agonist peptide mimetic, wherein the first agonist peptide mimetic replaces a single portion of a first complementarity determining region (CDR), said portion comprising one or more contiguous amino acid residues of the first CDR, and the second agonist peptide mimetic replaces a single portion of a second CDR, said portion comprising one or more continuous amino acid residues of the second CDR, and wherein the immunoglobulin molecule or a fragment thereof binds to and agonizes a receptor.

31. An immunoglobulin molecule or fragment thereof according to claim 30 further comprising at least one flanking sequence comprising at least one amino acid covalently linked to at least one end of at least one agonist peptide mimetic.

32. An immunoglobulin molecule or fragment thereof according to claim 31 wherein the at least one flanking sequence comprises a proline that is covalently linked to at least one peptide mimetic.

33. An immunoglobulin molecule or fragment thereof according to claim 31 wherein the flanking sequence consists of two amino acids.

34. An immunoglobulin molecule or fragment thereof according to claim 32 wherein the flanking sequence consists of two amino acids.

35. An immunoglobulin molecule or fragment thereof according to claim 30 wherein the immunoglobulin molecule fragment is selected from the group consisting of Fab fragment, $F(ab')_2$ fragment and scFv fragment.

36. An immunoglobulin molecule according to claim 30 wherein the immunoglobulin molecule is a full IgG molecule.

37. An immunoglobulin molecule or fragment thereof according to claim 30 wherein both CDRs are located on a heavy chain.

38. An immunoglobulin molecule or fragment thereof according to claim 30 wherein both CDRs are located on a light chain.

39. An immunoglobulin molecule or fragment thereof according to claim 30 wherein one CDR is located on a heavy chain and one CDR is located on a light chain.

40. An immunoglobulin molecule or fragment thereof according to claim 30 wherein the CDRs are a CDR2 and a CDR3.

41. An immunoglobulin molecule or fragment thereof according to claim 30 wherein the two peptide mimetics are identical.

42. An immunoglobulin molecule or fragment thereof according to claim 30 wherein the immunoglobulin molecule or fragment thereof is human.

43. An immunoglobulin molecule or fragment thereof according to claim 30 wherein the immunoglobulin molecule or fragment thereof is anti-tetanus toxoid.

44. A composition comprising an immunoglobulin or fragment thereof according to claim 30 and a pharmaceutically acceptable carrier.

45. An immunoglobulin molecule or fragment thereof comprising at least a first erythropoietin (EPO) peptide mimetic and at least a second EPO peptide mimetic, wherein the first EPO peptide mimetic replaces a single portion of a first complementarity determining region (CDR), said portion comprising one or more contiguous amino acid residues of the first CDR, and the second EPO peptide mimetic replaces a single portion of a second CDR, said portion comprising one or more contiguous amino acid residues of the second CDR, and wherein the immunoglobulin molecule or a fragment thereof binds to and agonizes an EPO receptor.

46. An immunoglobulin molecule or fragment thereof according to claim 45 further comprising at least one flanking sequence including at least one amino acid covalently linked to at least one end of at least one peptide mimetic.

47. An immunoglobulin molecule or fragment thereof according to claim 46 wherein the at least one flanking sequence includes a flanking sequence having a proline that is covalently linked to the peptide mimetic.

48. An immunoglobulin molecule or fragment thereof according to claim 45 wherein the immunoglobulin molecule fragment is selected from the group consisting of Fab fragment, F(ab')$_2$ fragment and scFv fragment.

49. An immunoglobulin molecule according to claim 45 wherein the immunoglobulin molecule is a full IgG molecule.

50. An immunoglobulin molecule or fragment thereof according to claim 45 wherein the two CDRs are both located on a heavy chain.

51. An immunoglobulin molecule or fragment thereof according to claim 45 wherein the immunoglobulin molecule or fragment thereof is human.

52. An immunoglobulin molecule or fragment thereof according to claim 45 wherein the immunoglobulin molecule or fragment thereof is anti-tetanus toxoid.

53. A composition comprising an immunoglobulin or fragment thereof according to claim 45 and a pharmaceutically acceptable carrier.

54. An immunoglobulin molecule or fragment thereof according to claim 45 wherein the CDRs are both located on a light chain.

55. An immunoglobulin molecule or fragment thereof according to claim 45 wherein one CDR is located on a heavy chain and one CDR is located on a light chain.

56. An immunoglobulin molecule or fragment thereof according to claim 45 wherein the CDRs are selected from the group consisting of CDR2 and CDR3.

57. An immunoglobulin molecule or fragment thereof according to claim 56 wherein at least one of the CDRs is located in a heavy chain.

58. An immunoglobulin molecule or fragment thereof according to claim 56 wherein at least one of the CDRs is located in a light chain.

59. An immunoglobulin molecule or fragment thereof according to claim 56 wherein one CDR is a CDR2 and one CDR is a CDR3.

60. An immunoglobulin molecule or fragment thereof according to claim 56 wherein the CDRs are selected from the group consisting of heavy chain CDR3-light chain CDR3, heavy chain CDR3-heavy chain CDR2, light chain CDR3-light chain CDR2, heavy chain CDR3-light chain CDR2, heavy chain CDR3-heavy chain CDR2-light chain CDR2, and heavy chain CDR2-light chain CDR2.

61. An immunoglobulin molecule or fragment thereof according to claim 45 wherein the CDRs are heavy chain CDR3 and light chain CDR1.

62. An immunoglobulin molecule or fragment thereof according to claim 47 wherein at least one peptide mimetic is flanked with a proline at the carboxy terminus.

63. An immunoglobulin molecule or fragment thereof according to claim 46 wherein the flanking sequence consists of two amino acids.

64. An immunoglobulin molecule or fragment thereof according to claim 47 wherein the flanking sequence consists of two amino acids.

65. An immunoglobulin molecule or fragment thereof according to claim 45 wherein the two peptide mimetics are identical.

* * * * *

UNITED STATES PATENT AND TRADEMARK OFFICE
CERTIFICATE OF CORRECTION

PATENT NO. : 7,396,917 B2
APPLICATION NO. : 10/307724
DATED : July 8, 2008
INVENTOR(S) : Bowdish et al.

Page 1 of 1

It is certified that error appears in the above-identified patent and that said Letters Patent is hereby corrected as shown below:

In the claims:

Claim 1, Column 113, line 49, change "atleast" to -- at least --.

Claim 1, Column 113, line 50, change "atleast" to -- at least --.

Claim 30, Column 116, line 15, change "continuous" to -- contiguous --.

Signed and Sealed this

Twenty-fifth Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,396,917 B2 | Page 1 of 1 |
| APPLICATION NO. | : 10/307724 | |
| DATED | : July 8, 2008 | |
| INVENTOR(S) | : Bowdish et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 653 days.

Signed and Sealed this
Twenty-first Day of August, 2012

David J. Kappos
*Director of the United States Patent and Trademark Office*